(12) United States Patent
Gilbert et al.

(10) Patent No.: US 9,422,277 B2
(45) Date of Patent: Aug. 23, 2016

(54) TRICYCLIC SUBSTITUTED THIADIAZINE DIOXIDE COMPOUNDS AS BACE INHIBITORS, COMPOSITIONS AND THEIR USE

(71) Applicant: Merck Sharp & Dohme Corp., Rahway, NJ (US)

(72) Inventors: Eric J. Gilbert, Scotch Plains, NJ (US); Jared N. Cumming, Garwood, NJ (US); Andrew W. Stamford, Chatham, NJ (US); Younong Yu, East Brunswick, NJ (US); Jack D. Scott, Scotch Plains, NJ (US); Ulrich Iserloh, Hoboken, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/433,296

(22) PCT Filed: Oct. 14, 2013

(86) PCT No.: PCT/US2013/064795
§ 371 (c)(1),
(2) Date: Apr. 2, 2015

(87) PCT Pub. No.: WO2014/062549
PCT Pub. Date: Apr. 24, 2014

(65) Prior Publication Data
US 2015/0274716 A1   Oct. 1, 2015

Related U.S. Application Data

(60) Provisional application No. 61/714,966, filed on Oct. 17, 2012.

(51) Int. Cl.
| | | |
|---|---|---|
| *C07D 417/14* | (2006.01) |
| *C07D 417/10* | (2006.01) |
| *C07D 417/04* | (2006.01) |
| *A61K 31/549* | (2006.01) |
| *A61K 45/06* | (2006.01) |
| *C07D 471/04* | (2006.01) |

(52) U.S. Cl.
CPC ............ *C07D 417/14* (2013.01); *A61K 31/549* (2013.01); *A61K 45/06* (2013.01); *C07D 417/10* (2013.01); *C07D 471/04* (2013.01)

(58) Field of Classification Search
CPC .. C07D 417/14; C07D 417/10; C07D 417/04; A61K 31/549; A61K 45/06
USPC ............................................. 544/8; 514/222.5
See application file for complete search history.

(56) References Cited

U.S. PATENT DOCUMENTS

| 3,423,408 A | 1/1969 | Pfirmann et al. |
| 5,534,520 A | 7/1996 | Fisher et al. |
| 5,889,002 A | 3/1999 | Nielsen et al. |
| 6,225,310 B1 | 5/2001 | Nielson et al. |
| 7,648,983 B2 | 1/2010 | Audia et al. |
| 2007/0287692 A1 | 12/2007 | Wu et al. |
| 2008/0200445 A1 | 8/2008 | Zhu et al. |
| 2010/0075957 A1 | 3/2010 | Tamura et al. |
| 2012/0183563 A1 | 7/2012 | Scott et al. |
| 2012/0189642 A1 | 7/2012 | Scott et al. |
| 2012/0258961 A1 | 10/2012 | Suzuki et al. |
| 2015/0274716 A1 | 10/2015 | Gilbert et al. |

(Continued)

FOREIGN PATENT DOCUMENTS

| EP | 1942105 | 7/2008 |
| WO | 2007049532 A1 | 5/2007 |

(Continued)

OTHER PUBLICATIONS

Esteban, Al, et al., New 1,2,6-Thizdiazine Dioxide Acyclonucleaosides: Synthesis and Antiviral Evaluation, Bioorganic & Medicinal Chemistry, 1995, 1527-1535, vol. 3, No. 1.

(Continued)

*Primary Examiner* — Kahsay Habte
(74) *Attorney, Agent, or Firm* — Keith D. MacMillan; John C. Todaro

(57) ABSTRACT

In its many embodiments, the present invention provides certain iminothiazine dioxide compounds, including compounds Formula (I): and tautomers and stereoisomers thereof, and pharmaceutically acceptable salts of said compounds, said tautomeros and said stereoisomers, wherein the middle ring (referred to herein as "ring B") of the tricyclic substituent is an optionally substituted 5-membered ring, and each of the remaining variables shown in the formula are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including Alzheimer's disease, are also disclosed.

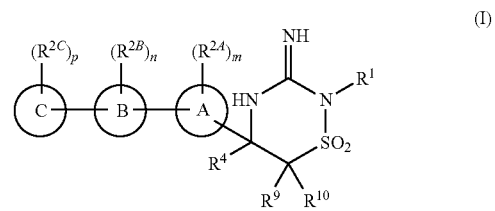

(I)

13 Claims, No Drawings

(56) References Cited

U.S. PATENT DOCUMENTS

| | | |
|---|---|---|
| 2015/0284379 A1 | 10/2015 | Gilbert et al. |
| 2015/0353516 A1 | 12/2015 | Cumming et al. |

FOREIGN PATENT DOCUMENTS

| | | |
|---|---|---|
| WO | 2008133274 | 6/2008 |
| WO | 2008103351 | 8/2008 |
| WO | 2011044181 | 4/2011 |
| WO | 2011044184 | 4/2011 |
| WO | 2011044185 | 4/2011 |
| WO | 2011044187 A1 | 4/2011 |
| WO | 2011154374 | 12/2011 |
| WO | 2011154431 | 12/2011 |
| WO | 2012138734 A1 | 10/2012 |
| WO | 2014099768 A1 | 6/2014 |
| WO | 2014150331 A1 | 9/2014 |
| WO | 2014150340 A1 | 9/2014 |
| WO | 2015094930 A1 | 6/2015 |

OTHER PUBLICATIONS

Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.

Guo, et al., Targeting Amyloid-B in Glaucoma Treatment, pp. 13444-13449, PNAS, Aug. 14, 2007, vol. 104, No. 33.

International Search Report dated Mar. 18, 2014 for PCT/US2013/064795.

Loane, et al., Amyloid Precursor Protein Secretases as Therapeutic Targets for Traumatic Brain Injury, Nature Medicine, Advance Online Publication, published online Mar. 15, 2009; doi:10.1038/nm.1940, pp. 1-3.

Luo, et al., Mice deficient in BACE1, the Alzheimer's B-secretase, have normal phenotype and abolished B-amyloid, Nature Neuroscience, vol. 4, No. 3, Mar. 2001.

McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.

Ohno, et al., BACE1 deficiency rescues memory deficits and Cholinergic function in a mouse model of Alzheimer's disease, Neuron, vol. 41, 27-33, Jan. 8, 2004.

Ohno, et al. BACE1 gene deletion prevents neuron loss and memory deficits in 5XFAD APP/PS1 transgenic mice, Neurobiology of disease 26 (2006), pp. 134-145.

Osherovich, L. AB's Dry (AMD) Humor, SciBX 4(26); doi:10.1038/scibx.2011.727, Published online Jun. 30, 2011.

Preliminary Examination Report dated Apr. 30, 2015 for PCT/US2013/064795.

Probst, et al., Small-molecule BACE1 inhibitors: a patent literature review, Expert Opinion on Therapeutic Patents, (2006-2011), 2012, 22(5):511-540.

Roberds, et al., BACE knockout mice are healthy despite lacking the primary B-secretase activity in the brain: Implications for Alzheimer's disease therapeutics, Human Mol. Genetics, vol. 10, No. 12, pp. 1317-1324. Apr. 3, 2004.

Salloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.

Scott, et al., "Novel Imino Pyrimidinone B-Secretase (BACE1) Inhibitors. P1 Thiophenes", Poster presentation, American Chemical Society, Sprint 2011.

Southan, BACE2 as a New Diabetes Target: a patent review 2010-2012, Expert Opinion on Therapeutic Patents, 2013, Informa UK, Ltd., ISSN 1354-3776, e-1744-7674.

Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.

Stamford, et al., Inhibitors of BACE for treating Alzheimer's disease: a fragment-based drug discovery story, Current Opinion in Chemical Biology; v:17 i:3 p. 320-328; Jun. 2013 Elsevier.

Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.

Weiner, Further insights into Alzheimer disease pathogenesis, Weiner, M. W. Nat. Rev. Neurol. 9, 65-66 (2013); published online Jan. 22, 2013.

Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

TRICYCLIC SUBSTITUTED THIADIAZINE DIOXIDE COMPOUNDS AS BACE INHIBITORS, COMPOSITIONS AND THEIR USE

FIELD OF THE INVENTION

This invention provides certain tricyclic substituted thiadiazine dioxide compounds in which the middle ring (referred to herein as "ring B") of the tricyclic substituent is an optionally substituted 5-membered ring, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE and to identify inhibitors of BACE-1 and/or BACE-2 and of other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, WO2010/047372, WO2011/044181, WO2011/044185, WO2011/044187, PCT/US10/51557, PCT/US12/31783, PCT/CN2012/000497, and PCT/US12/051687.

SUMMARY OF THE INVENTION

The present invention provides certain tricyclic substituted thiadiazine dioxide compounds in which the middle ring ("ring B") of the tricyclic substituent is an optionally substituted 5-membered ring, which are collectively or individually referred to herein as "compound(s) of the invention", as described herein. The compounds of the invention are useful as inhibitors of BACE-1 and/or BACE-2.

In one embodiment, the compounds of the invention have the structural Formula (I):

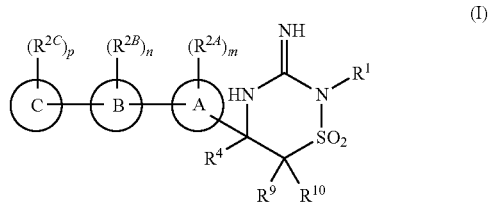

or a tautomer thereof having the structural Formula (I'):

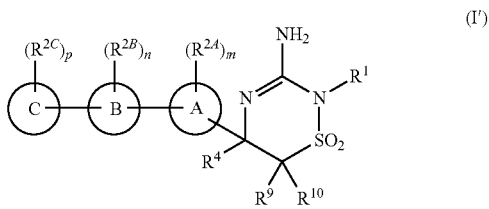

or pharmaceutically acceptable salt thereof, wherein:

$R^1$ is selected from the group consisting of H, lower alkyl, and cyclopropyl;

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2A}$ (when present) is independently selected from the group consisting of: halo, oxo, —OH, —CN, —SF$_5$, —OSF$_5$, —NO$_2$, —Si(R$^5$)$_3$, —N(R$^6$)$_2$, —OR$^6$, —SR$^6$, alkyl, haloalkyl, heteroalkyl, alkenyl, alkynyl, cycloalkyl, -alkyl-cycloalkyl, heterocycloalkyl, and -alkyl-heterocycloalkyl, wherein said alkyl, haloalkyl, heteroalkyl, alkenyl, alkynyl, cycloalkyl, -alkyl-cycloalkyl, heterocycloalkyl, and -alkyl-heterocycloalkyl of $R^{2A}$ are each optionally unsubstituted or substituted with one or more groups independently selected from $R^8$;

m is 0 or more;

ring B is selected from the group consisting of a 5-membered heteroaryl, a 5-membered heterocycloalkyl, a 5-membered heterocycloalkenyl ring, a 5-membered cycloalkyl ring, and a 5-membered cycloalkenyl ring, wherein each said ring comprises from 1 to 4 ring heteroatoms independently selected from the group consisting of N, N-oxide, O, S, S(O), and S(O)$_2$;

each $R^{2B}$ (when present) is independently selected from the group consisting of halo, —CN, alkyl, cycloalkyl, -alkyl-cycloalkyl, heterocycloalkyl, -alkyl-heterocycloalkyl, heteroalkyl, haloalkyl —O-alkyl, —O-cycloalkyl, —O-alkyl-cycloalkyl, —O-heteroalkyl, and —O-haloalkyl;

n is 0 or more;

ring C is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2C}$ (when present) is independently selected from the group consisting of: halo, oxo, —OH, —CN, —SF$_5$, —OSF$_5$, —Si(R$^5$)$_3$, —N(R$^6$)$_2$, —NR$^7$C(O)R$^6$, —NR$^7$S(O)$_2$R$^{12}$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^{12}$, —S(O)$_2$R$^{12}$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, -aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^{2C}$ are each optionally unsubstituted or substituted with one or more groups independently selected from $R^8$;

p is 0 or more;

$R^4$ is selected from the group consisting of lower alkyl and lower haloalkyl;

each $R^5$ (when present) is independently selected from the group consisting of alkyl, heteroalkyl, haloalkyl, cycloalkyl, and -alkyl-cycloalkyl;

each $R^6$ (when present) is independently selected from the group consisting of H, alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^6$ is unsubstituted or substituted with one or more groups independently selected from halo, —CN, —OH, lower alkyl, cycloalkyl, lower heteroalkyl, lower haloalkyl, lower —O-alkyl, lower —O-heteroalkyl, and lower —O-haloalkyl;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said cycloalkyl, -alkyl-cycloalkyl, aryl, -alkyl-aryl, heteroaryl, and -alkyl-heteroaryl of $R^7$ is unsubstituted or substituted with one or more groups independently selected from halo, —CN, lower alkyl, cycloalkyl, lower heteroalkyl, lower haloalkyl, lower —O-alkyl, lower —O-heteroalkyl, and lower —O-haloalkyl;

each $R^8$ (when present) is independently selected from the group consisting of halo, oxo, —OH, —CN, —SF$_5$, —OSF$_5$, alkyl, —O-alkyl, haloalkyl, haloalkoxy, —C(O)OR$^{11}$, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ is selected from the group consisting of H, halo, alkyl, cycloalkyl, haloalkyl, and heteroalkyl;

$R^{10}$ is selected from the group consisting of H, halo, alkyl, cycloalkyl, haloalkyl, and heteroalkyl;

$R^{11}$ (when present) is selected from the group consisting of H, lower alkyl, lower heteroalkyl, cycloalkyl, and -alkyl-cycloalkyl; and each $R^{12}$ (when present) is independently selected from the group consisting of alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^{12}$ is unsubstituted or substituted with one or more groups independently selected from halo, —CN, —OH, lower alkyl, cycloalkyl, lower heteroalkyl, lower haloalkyl, lower —O-alkyl, lower —O-heteroalkyl, and lower —O-haloalkyl.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA).

In one embodiment, the compounds of the invention have the structural Formula (I) or (I') as described above.

In one embodiment, the compounds of the invention have the structural Formula (IA):

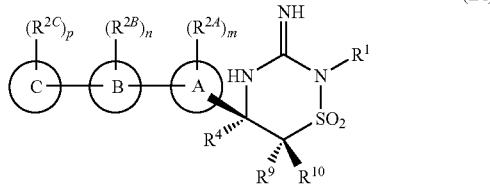

or a tautomer thereof having the structural Formula (IA'):

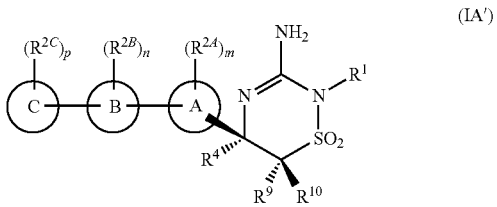

or a pharmaceutically acceptable salt thereof, wherein each variable is as described in Formula (I).

In one embodiment, in each of Formulas (I), (IA), and (IA'): $R^1$ is selected from the group consisting of H, methyl, ethyl, cyclopropyl, and cyclopropylmethyl.

In one embodiment, in each of Formulas (I), (IA), and (IA'): $R^1$ is selected from the group consisting of methyl and ethyl.

In one embodiment, in each of Formulas (I), (IA), and (IA'): $R^1$ is methyl.

In one embodiment, in each of Formulas (I), (IA), and (IA'), $R^9$ is selected from the group consisting of H, halo, lower alkyl, cycloalkyl, lower haloalkyl, and lower heteroalkyl.

In one embodiment, in each of Formulas (I), (IA), and (IA'), $R^9$ is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'), $R^9$ is H.

In one embodiment, in each of Formulas (I), (IA), and (IA'), $R^{10}$ is selected from the group consisting of H, halo, lower alkyl, lower haloalkyl, and lower heteroalkyl.

In one embodiment, in each of Formulas (I), (IA), and (IA'), $R^{10}$ is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'), $R^{10}$ is H.

In one embodiment, in each of Formulas (I), (IA), and (IA'), $R^9$ is selected from the group consisting of H, halo, lower alkyl, cycloalkyl, lower haloalkyl, and lower heteroalkyl; and $R^{10}$ is H.

In one embodiment, in each of Formulas (I), (IA), and (IA'), $R^9$ is selected from the group consisting of H, fluoro, methyl, ethyl, cyclopropyl, —CH$_2$F, —CHF$_2$, —CF$_3$, —CH$_2$OCH$_3$; and $R^{10}$ is H.

In one embodiment, in each of Formulas (I), (IA), and (IA'), $R^9$ is H; and $R^{10}$ is selected from the group consisting of H, halo, lower alkyl, cycloalkyl, lower haloalkyl, and lower heteroalkyl.

In one embodiment, in each of Formulas (I), (IA), and (IA'), $R^9$ is H; and $R^{10}$ is selected from the group consisting of H, fluoro, methyl, ethyl, cyclopropyl, —CHF$_2$, —CF$_3$, —CH$_2$OCH$_3$.

In one embodiment, in each of Formulas (I), (IA), and (IA'), $R^{10}$ is H and $R^9$ is H.

In one embodiment, in each of Formulas (I), (IA), and (IA'), $R^4$ is selected from the group consisting of —CH$_3$, —CH$_2$F, —CHF$_2$, and —CF$_3$.

In one embodiment, in each of Formulas (I), (IA), and (IA'), $R^4$ is selected from the group consisting of —CH$_3$, and —CHF$_2$.

In one embodiment, in each of Formulas (I), (IA), and (IA'):

$R^4$ is selected from the group consisting of —CH$_3$ and —CHF$_2$; and one of $R^9$ and $R^{10}$ is H and the other is selected from the group consisting of H, halo, lower alkyl, cycloalkyl, lower haloalkyl, and lower heteroalkyl.

In one embodiment, in each of Formulas (I), (IA), and (IA'):

$R^4$ is selected from the group consisting of —CH$_3$ and —CHF$_2$; and one of $R^9$ and $R^{10}$ is H and the other is selected from the group consisting of H, fluoro, methyl, ethyl, cyclopropyl, —CF$_3$, —CH$_2$OCH$_3$.

In one embodiment, in each of Formulas (I), (IA), and (IA'):

$R^4$ is selected from the group consisting of —CH$_3$ and —CHF$_2$;

$R^9$ is H; and $R^{10}$ is H.

In one embodiment, the compounds of the invention have the structural Formula (II):

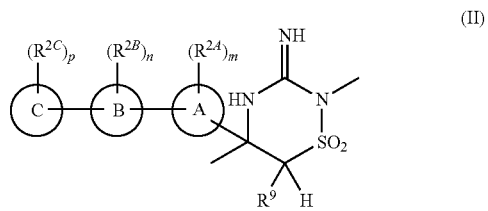

or a tautomer thereof having the structural Formula (II'):

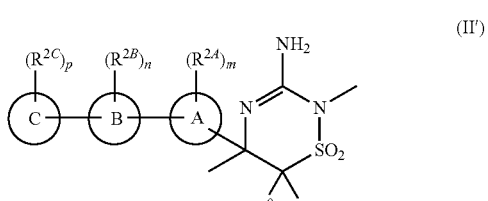

or pharmaceutically acceptable salt thereof, wherein each variable is as described in Formula (I).

In one embodiment, the compounds of the invention have the structural Formula (IIA):

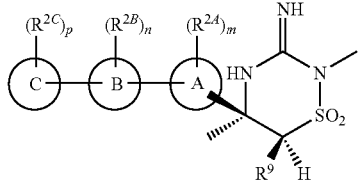

(IIA)

or a tautomer thereof having the structural Formula (IIA'):

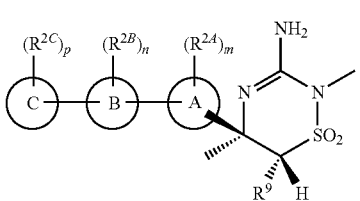

(IIA')

or pharmaceutically acceptable salt thereof, wherein each variable is as described in Formula (I).

In one embodiment, the compounds of the invention have the structural Formula (IIB):

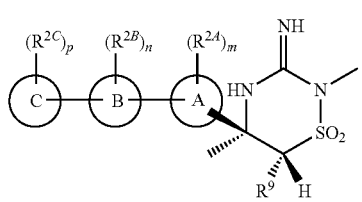

(IIB)

or a tautomer thereof having the structural Formula (IIB'):

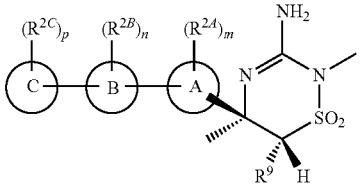

(IIB')

or pharmaceutically acceptable salt thereof, wherein each variable is as described in Formula (I).

In one embodiment, in each of Formulas (I), (IA), (IA'), (II), (II'), (IIA), (IIA'), (IIB), and (IIB'): m is 0 or more and ring A is selected from the group consisting of phenyl, pyridyl, pyrazinyl, furanyl, thienyl, pyrimidinyl, pyridazinyl, thiazolyl, thiadiazolyl, isothiazolyl, oxazolyl, oxadiazolyl, isoxazolyl, imidazolyl, pyrazolyl, pyrrolyl, quinazolinyl, benzofuranyl, benzimidazolyl, benzoxazolyl, benzoisoxazolyl, benzothiazolyl, benzoisothiazolyl, benzothienyl, naphthyl, quinolyl, isoquinolyl, indazolyl, indolyl, thienylpyridinyl, and thienylpyrazolyl.

In one embodiment, in each of Formulas (I), (IA), (IA'), (II), (II'), (IIA), (IIA'), (IIB), and (IIB'): m is 0 or more and ring A is selected from the group consisting of phenyl, pyridyl, thienyl, thiazolyl, pyrazolyl, naphthyl, quinolinyl, benzothienyl, benzimidazolyl, indazolyl, indolyl, and thienylpyridinyl.

In one embodiment, in each of Formulas (I), (IA), (IA'), (II), (II'), (IIA), (IIA'), (IIB), and (IIB'): m is 0 or more and ring A is selected from the group consisting of phenyl, pyridyl, thienyl, thienylpyridinyl, and benzothienyl.

It shall be understood that, in each of Formulas (I), (IA), (IA'), (II), (II'), (IIA), (IIA'), (IIB), and (IIB), when m (or n or p) is 0 or more, the maximum number of m (or of n or of p) is the maximum number of substitutable hydrogen atoms on the ring to which $R^{2A}$ (or $R^{2B}$ in the case of n $R^{2C}$ in the case of p) is shown attached.

Thus, in embodiments wherein ring A is a moiety having 4 substitutable hydrogen atoms, m is 0, 1, 2, 3, or 4. In an alternative of such embodiments wherein ring A is a moiety having 4 substitutable hydrogen atoms, m is 0, 1, 2, or 3. In an alternative of such embodiments wherein ring A is a moiety having 4 substitutable hydrogen atoms, m is 0, 1, or 2. In an alternative of such embodiments wherein ring A is a moiety having 4 substitutable hydrogen atoms, m is 0 or 1. In an alternative of such embodiments wherein ring A is a moiety having 4 substitutable hydrogen atoms, m is 0.

In embodiments wherein ring A is a moiety having 3 substitutable hydrogen atoms, m is 0, 1, 2, or 3. In an alternative of such embodiments wherein ring A is a moiety having 3 substitutable hydrogen atoms, m is 0, 1, or 2. In an alternative of such embodiments wherein ring A is a moiety having 3 substitutable hydrogen atoms, m is 0 or 1. In alternative of such embodiments wherein ring A is a moiety having 3 substitutable hydrogen atoms, m is 0.

In embodiments wherein ring A is a moiety having 2 substitutable hydrogen atoms, m is 0, 1, or 2. In an alternative of such embodiments wherein ring A is a moiety having 2 substitutable hydrogen atoms, m is 0 or 1. In alternative of such embodiments wherein ring A is a moiety having 2 substitutable hydrogen atoms, m is 0.

In one embodiment, in each of Formulas (I), (IA), (IA'), (II), (II'), (IIA), (IIA'), (IIB), and (IIB'): each $R^{2A}$ group (when present) is independently selected from the group consisting of halo, oxo, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, propyl, cyclopropyl, —CH$_2$-cyclopropyl, —C≡C—CH$_3$, —CF$_3$, —CHF$_2$, —OCF$_3$, and —OCHF$_2$.

In one embodiment, in each of Formulas (I), (IA), (IA'), (II), (II'), (IIA), (IIA'), (IIB), and (IIB'): each $R^{2A}$ group (when present) is independently selected from fluoro, chloro, bromo, —CN, —CF$_3$, —CHF$_2$, —CH$_2$F, cyclopropyl, —OCF$_3$, and —OCHF$_2$.

In one embodiment, in each of Formulas (I), (IA), (IA'), (II), (II'), (IIA), (IIA'), (IIB), and (IIB'): each $R^{2A}$ group (when present) is independently selected from the group consisting of fluoro, chloro, —CHF$_2$, and —CF$_3$.

In one embodiment, in each of Formulas (I), (IA), (IA'), (II), (II'), (IIA), (IIA'), (IIB), and (IIB'): each $R^{2A}$ group (when present) is independently selected from the group consisting of fluoro and chloro.

In one embodiment, in each of Formulas (I), (IA), (IA'), (II), (II'), (IIA), (IIA'), (IIB), and (IIB'):
ring B is selected from the group consisting of pyrrolyl, imidazolyl, oxadiazolyl, triazolyl, isoxazolyl, oxazolyl, thienyl, pyrazolyl, furanyl, tetrazolyl, thiazolyl, and isothiazolyl.

In one embodiment, in each of Formulas (I), (IA), (IA'), (II), (II'), (IIA), (IIA'), (IIB), and (IIB'):
 ring B is selected from the group consisting of pyrrolyl, imidazolyl, oxadiazolyl, triazolyl, and isoxazolyl.

In embodiments wherein ring B is a moiety having 3 substitutable hydrogen atoms, n is 0, 1, 2, or 3. In an alternative of such embodiments wherein ring B is a moiety having 3 substitutable hydrogen atoms, n is 0, 1, or 2. In an alternative of such embodiments wherein ring B is a moiety having 3 substitutable hydrogen atoms, n is 0 or 1. In alternative of such embodiments wherein ring B is a moiety having 3 substitutable hydrogen atoms, n is 0.

In embodiments wherein ring B is a moiety having 2 substitutable hydrogen atoms, n is 0, 1, or 2. In an alternative of such embodiments wherein ring B is a moiety having 2 substitutable hydrogen atoms, n is 0 or 1. In alternative of such embodiments wherein ring B is a moiety having 2 substitutable hydrogen atoms, n is 0.

In embodiments wherein ring B is a moiety having 1 substitutable hydrogen atom, n is 0 or 1. In an alternative of such embodiments wherein ring B is a moiety having 1 substitutable hydrogen atom, n is 1. In alternative of such embodiments wherein ring B is a moiety having 1 substitutable hydrogen atom, n is 0.

In one embodiment, in each of Formulas (I), (IA), (IA'), (II), (II'), (IIA), (IIA'), (IIB), and (IIB'):
 each $R^{2B}$ (when present) is independently selected from the group consisting of halo, —CN, methyl, ethyl, propyl, cyclopropyl, —CH$_2$-cyclopropyl, —OCH$_3$, —CH$_2$OCH$_3$, —CHF$_2$, —CH$_2$F, —CF$_3$, —OCF$_3$, and —OCHF$_2$.

In one embodiment, in each of Formulas (I), (IA), (IA'), (II), (II'), (IIA), (IIA'), (IIB), and (IIB'):
 each $R^{2B}$ (when present) is independently selected from the group consisting of fluoro, chloro, —CN, methyl, cyclopropyl, —CH$_2$OCH$_3$, —CHF$_2$, and —CF$_3$.

In one embodiment, in each of Formulas (I), (IA), (IA'), (II), (II'), (IIA), (IIA'), (IIB), and (IIB'):
 ring C is selected from the group consisting of azetidinyl, benzimidazolyl, benzothiazolyl, cyclopropyl, cyclobutyl, dihydroindenyl, dihydrooxazolyl, furanyl, imadazolyl, indenyl, indolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrazolopyridinyl, pyrrolyl, pyrrolopyridinyl, pyrrolopyrimidinyl, tetrazolyl, thiadiazolyl, thiazolyl, thienyl, thiomorpholinyl, thiomorpholinyl dioxide, triazolyl.

In one embodiment, in each of Formulas (I), (IA), (IA'), (II), (II'), (IIA), (IIA'), (IIB), and (IIB'):
 ring C is selected from the group consisting of azetidinyl, cyclopropyl, cyclobutyl, dihydrooxazolyl, imadazolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrrolyl, tetrazolyl, thiadiazolyl, thiazolyl, thienyl, thiomorpholinyl, thiomorpholinyl dioxide, triazolyl.

In one embodiment, in each of Formulas (I), (IA), (IA'), (II), (II'), (IIA), (IIA'), (IIB), and (IIB'): p is 0 and $R^{2C}$ is absent.

In one embodiment, in each of Formulas (I), (IA), (IA'), (II), (II'), (IIA), (IIA'), (IIB), and (IIB'): p is 1 or more and at least one $R^{2C}$ group is present.

In one embodiment, in each of Formulas (I), (IA), (IA'), (II), (II'), (IIA), (IIA'), (IIB), and (IIB'):
 each $R^2$ group (when present) is independently selected from the group consisting of halo, oxo, —CN, —SF$_5$, —OSF$_5$, —N(R$^6$)$_2$, —NR$^7$C(O)R$^6$, —NR$^7$S(O)$_2$R$^{12}$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^{12}$, —S(O)$_2$R$^{12}$, —S(O)$_2$N(R$^6$)$_2$, —OR$^6$, —SR$^6$, lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl,
 wherein each said lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl of $R^2$ (when present) is independently unsubstituted or substituted with one or more groups independently selected from the group consisting of $R^8$.

In one embodiment, in each of Formulas (I), (IA), (IA'), (II), (II'), (IIA), (IIA'), (IIB), and (IIB'):
 each $R^{2C}$ group (when present) is independently selected from the group consisting of halo, oxo, —CN, —OR$^6$, —SR$^6$, lower alkyl, lower haloalkyl, lower heteroalkyl, lower alkynyl, aryl, -alkyl-aryl, cycloalkyl, heteroaryl, -alkyl-heteroaryl, heterocycloalkyl, and heterocycloalkenyl,
 wherein each said lower alkyl, lower haloalkyl, lower heteroalkyl, lower alkynyl, aryl, -alkyl-aryl, cycloalkyl, heteroaryl, -alkyl-heteroaryl, heterocycloalkyl, and heterocycloalkenyl of $R^{2C}$ (when present) is independently unsubstituted or substituted with one or more groups independently selected from the group consisting of $R^8$.

An alternative embodiment of $R^6$ when at least one $R^{2C}$ is —OR$^6$, —N(R$^6$)$_2$, and/or —SR$^6$ includes H, lower alkyl, lower haloalkyl, cyclopropyl, phenyl, and benzyl.

An alternative embodiment of aryl when at least one $R^{2C}$ is aryl or -alkyl-aryl includes phenyl and benzyl. As stated above, each said aryl or -alkyl-aryl group is optionally unsubstituted or substituted with one or more $R^8$ groups.

An alternative embodiment of heteroaryl when at least one $R^{2C}$ is heteroaryl or -alkyl-heteroaryl includes pyridyl, pyrazinyl, pyrrolyl, furanyl, thienyl, pyrimidinyl, pyridazinyl, thiazolyl, thiadiazoyl, isothiazoyl, oxazolyl, oxadiazoyl, isoxazoyl, imidazolyl, pyrazolyl, tetrazoyl, triazoyl, or lower alkyl linked versions thereof. As stated above, each said heteroaryl or -alkyl-heteroaryl group is optionally unsubstituted or substituted with one or more $R^8$ groups.

An alternative embodiment of cycloalkyl when at least one $R^{2C}$ is cycloalkyl includes cyclopropyl, cyclobutyl, cyclopentyl and cyclohexyl. As stated above, each said cycloalkyl group is optionally unsubstituted or substituted with one or more $R^8$ groups.

An alternative embodiment of heterocycloalkyl or heterocycloalkenyl when at least one $R^{2C}$ is heterocycloalkyl or heterocycloalkenyl includes piperidyl, pyrrolidinyl, piperazinyl, morpholinyl, thiomorpholinyl, thiazolidinyl, 1,4-dioxanyl, oxetanyl, tetrahydrofuranyl, tetrahydrothiophenyl. As stated above, each said heterocycloalkyl or heterocycloalkenyl group is optionally unsubstituted or substituted with one or more $R^8$ groups.

In an alternative of each of the preceeding embodiments wherein one or more $R^8$ groups are optionally present, said $R^8$ group is selected from the group consisting of fluoro, chloro, oxo, —CN, methyl, ethyl, propyl, cyclopropyl, —CH$_2$-cyclopropyl, —C(O)OCH$_3$, —OCH$_3$, —CH$_2$OCH$_3$, —CHF$_2$, —CH$_2$F, —CF$_3$, —OCF$_3$, and —OCHF$_2$.

In embodiments wherein ring C is a moiety having a given number of substitutable hydrogen atoms, p is 0, 1, 2, 3, 4, . . . up to said given number of substitutable hydrogen atoms.

Thus, by way of non-limiting example, in embodiments wherein ring C is a moiety having 4 substitutable hydrogen atoms, p is 0, 1, 2, 3, or 4. In an alternative of such embodiments wherein ring C is a moiety having 4 substitutable hydrogen atoms, p is 0, 1, 2, or 3. In an alternative of such embodiments wherein ring C is a moiety having 4 substitutable hydrogen atoms, p is 0, 1, or 2. In an alternative of such embodiments wherein ring C is a moiety having 4 substitutable hydrogen atoms, p is 0 or 1. In an alternative of such embodiments wherein ring C is a moiety having 4 substitutable hydrogen atoms, p is 0.

In embodiments wherein ring C is a moiety having 3 substitutable hydrogen atoms, p is 0, 1, 2, or 3. In an alternative of such embodiments wherein ring C is a moiety having 3 substitutable hydrogen atoms, p is 0, 1, or 2. In an alternative of such embodiments wherein ring C is a moiety having 3 substitutable hydrogen atoms, p is 0 or 1. In alternative of such embodiments wherein ring C is a moiety having 3 substitutable hydrogen atoms, p is 0.

In embodiments wherein ring C is a moiety having 2 substitutable hydrogen atoms, p is 0, 1, or 2. In an alternative of such embodiments wherein ring C is a moiety having 2 substitutable hydrogen atoms, p is 0 or 1. In alternative of such embodiments wherein ring C is a moiety having 2 substitutable hydrogen atoms, p is 0.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aft Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer or stereoisomer thereof, or pharmaceutically acceptable salt or solvate of said compound, said stereoisomer, or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several yeards before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer or stereoisomer thereof, or pharmaceutically acceptable salt or solvate of said compound, said stereoisomer, or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament which may be useful in: the treatment, the delay of onset, and/or the prevention of one or more Aβ pathologies and/or in the treatment, the delay of onset, and/or the prevention of one or more symptoms of one or more Aβ pathologies.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen. "Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, hetercycloalkyl, etc. indicates a divalent moiety, e.g., —CH$_2$CH$_2$— is ethylene, and

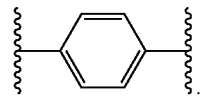

is para-phenylene.

"Alkynyl" means an aliphatic hydrocarbon group containing at least one carbon-carbon triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising about 3 to about 10 carbon atoms, preferably about 3 to about 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

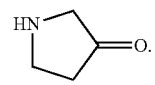

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and $S(O)_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

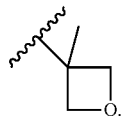

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

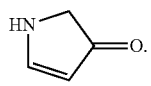

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocyloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof. It should be noted that in heteroatom containing ring systems of this invention, there are no hydroxyl groups on carbon atoms adjacent to a N, O or S, as well as there are no N or S groups on carbon adjacent to another heteroatom.

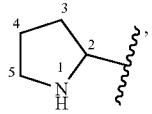

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl, as defined above. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic group includes bicyclic aromatic groups. Non-limiting examples of multicyclic groups which are bicyclic aromatic groups include:

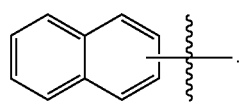

The term multicyclic group thus includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof. The term multicyclic group includes saturated bicyclic cycloalkyl groups. Non-limiting examples of multicyclic groups which are saturated bicyclic cycloalkyl groups include the following:

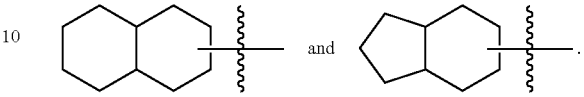

The term multicyclic group includes partially unsaturated bicyclic cycloalkyl groups. Non-limiting examples of multicyclic groups which comprise partially unsaturated bicyclic cycloalkyl groups include the following:

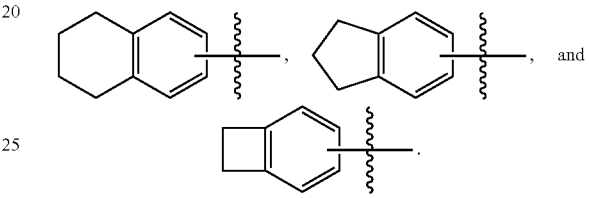

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S.

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S:

"Arylalkyl" (or "aralkyl") means an aryl-alkyl- group in which the aryl and alkyl are as previously described, except that in this context the "alkyl" portion of the "arylalkyl" (or "-alkyl-aryl") group refers to a straight or branched lower alkyl group. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" (or as "-alkyl-aryl") to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. As indicated above, the "alkyl" group in this context represents a lower alkyl group, which may be straight or branched, or unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^6$ in $-N(R^6)_2$, or a variable appears more than once in a structure presented herein, the variables can be the same or different.

The line ——, as a bond generally indicates a mixture of, or either of, the possible isomers, e.g., containing (R)- and (S)-stereochemistry. For example:

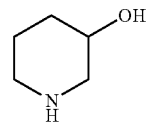

means containing both

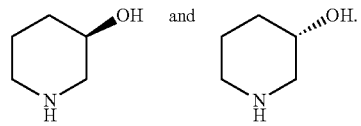

The wavy line ~~~, as used herein, indicates a point of attachment to the rest of the compound. Lines drawn into the ring systems, such as, for example:

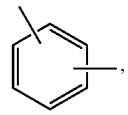

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

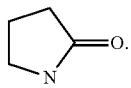

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

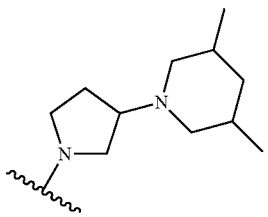

represents

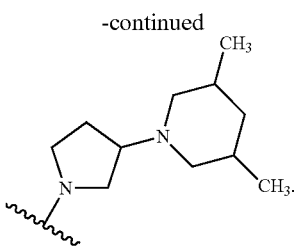

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{11}O$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation compring one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:

[1,1'-Bis(diphenylphosphino)ferrocene]-
dichloropalladium(II): PdCl$_2$dppf
1-(3-Dimethylaminopropyl)-3-
ethylcarbodiimide hydrochloride: EDCl
1,2-dimethoxyethane: DME
2-(Trimethylsilyl)ethanol: TMSethanol
2-(Trimethylsilyl)ethoxycarbonyl: Teoc
3-Chloroperoxybenzoic acid: mCPBA
Acetonitrile: MeCN
Allyl carbamate: Alloc
Aqueous: aq.
Atmosphere: atm
Benzyl: Bn
Bis(2-oxo-3-oxazolidinyl)phosphinic
chloride: BOPCl
n-Butyllithium: n-BuLi
Centimeters: cm
Ceric ammonium nitrate: CAN
Concentrated: conc.
Dichloromethane: DCM
2-Dicyclohexylphosphino-2',4',6'-
triisopropylbiphenyl: Xphos
Diisopropylamine: iPr$_2$NH
Diisopropylethylamine: DIEA or iPr$_2$NEt
Dimethylacetamide: DMA
Dimethylformamide: DMF
Dimethylsulfoxide: DMSO
Diphenylphosphoryl azide: DPPA
Ether or diethyl ether: Et$_2$O
Ethyl: Et
Ethyl acetate: AcOEt or EtOAc or EA
Ethyl alcohol: EtOH
Example: Ex. or ex.
Grams: g
Hexanes: hex
High performance liquid chromatography: HPLC
High resolution mass spectrometry: HRMS
Hours: hrs or h
Iron(III) acetylacetonate: Fe(acac)$_3$
Inhibition: Inh.
Liquid chromatography mass
Spectrometry: LCMS
Lithium diisopropylamide: LDA
Methanesulfonyl chloride: MeSO$_2$Cl
Methanol: MeOH
Methyl magnesium bromide: MeMgBr
methyl N-
(triethylammoniumsulfonyl)carbamate:
Burgess reagent
Micro liters: µl or µL
Milligrams: mg
Milliliters: mL
Millimoles: mmol
N-bromosuccinimide: NBS
n-Butyllithium: nBuLi or n-BuLi -continued Nuclear magnetic resonance spectroscopy: NMR
Palladium(II) acetate: Pd(OAc)$_2$
paramethoxy benzyl: PMB
Petroleum ether: PE
Preparative: prep
Retention time: $t_R$
Reverse Phase: RP
Room temperature (ambient, ~25° C.): rt or RT
Supercritical Fluid Chromatography: SFC
tert-Butoxycarbonyl: t-Boc or Boc
Tetrahydrofuran: THF
Thin layer chromatography: TLC
Triethylamine: Et$_3$N or TEA
Trifluoroacetic acid: TFA
2,4,6-Tripropyl-1,3,5,2,4,6-trioxatriphosphorinane-2,4-6-trioxide (1-propanephosphonic anhydride): T3P Method A

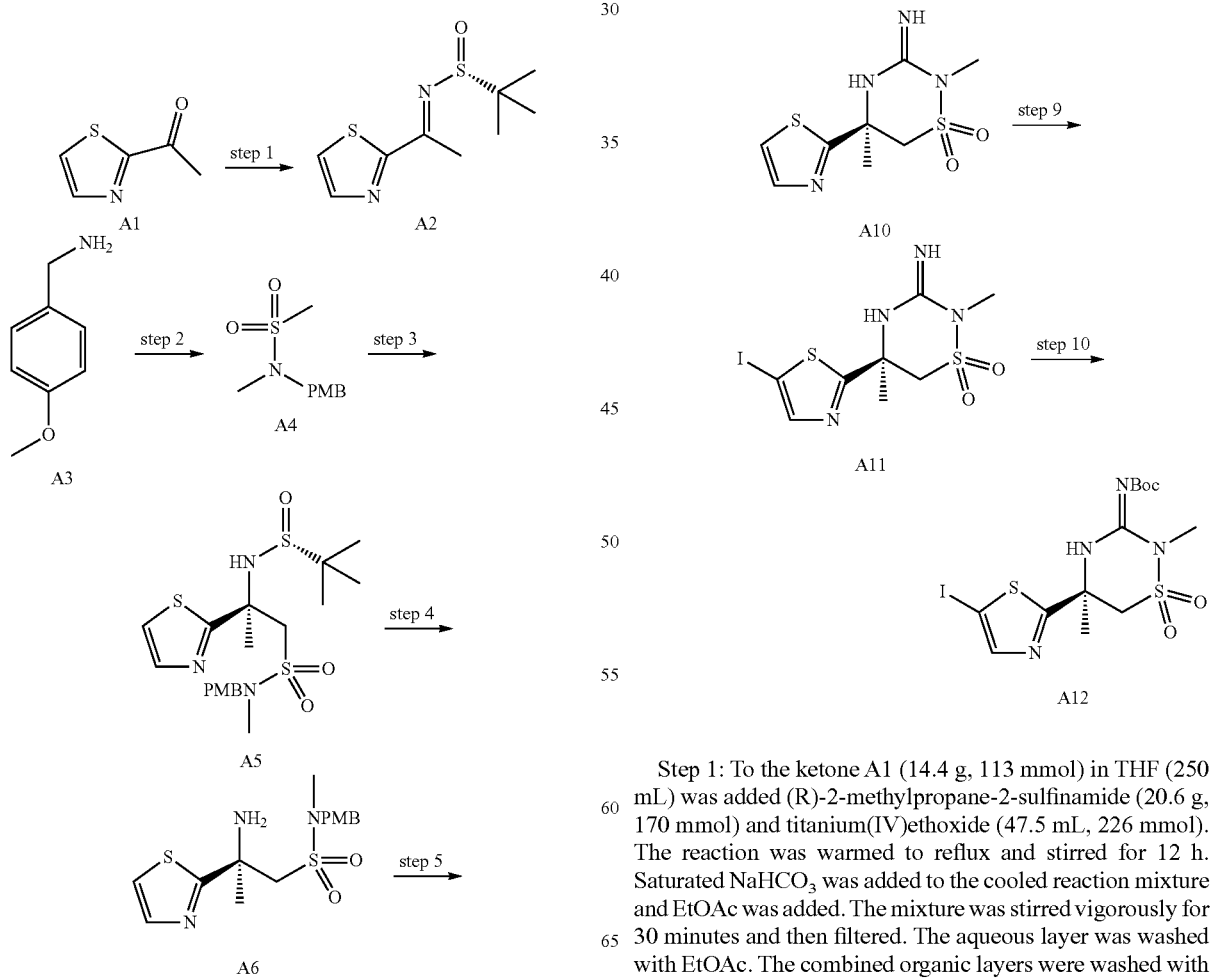

Step 1: To the ketone A1 (14.4 g, 113 mmol) in THF (250 mL) was added (R)-2-methylpropane-2-sulfinamide (20.6 g, 170 mmol) and titanium(IV)ethoxide (47.5 mL, 226 mmol). The reaction was warmed to reflux and stirred for 12 h. Saturated NaHCO$_3$ was added to the cooled reaction mixture and EtOAc was added. The mixture was stirred vigorously for 30 minutes and then filtered. The aqueous layer was washed with EtOAc. The combined organic layers were washed with water and brine, dried (MgSO$_4$), filtered, and concentrated in vacuo. The residue was purified by silica gel chromatography (0-30% EtOAc/hex) to provide A2.

Step 2: To a stirred solution of 4-methoxybenzyl amine A3 (198.9 g, 1.45 mol) in anhydrous pyridine (400 mL) at 0° C. was added drop wise via an addition funnel methanesulfonyl chloride (116 mL, 1.45 mol) over 45 min. After the addition was complete, the cooling bath was removed and the resultant solution was stirred at RT overnight. The reaction was concentrated in vacuo (water bath 60-65° C.) to remove most of the pyridine. The brown slurry was taken up in $CH_2Cl_2$ (1 L). The organic solution was washed with 1 N $HCl_{(aq.)}$ (2×1 L), sat. $NaHCO_3$ (2×1 L) and brine (1×500 mL). The organic layer was dried over $Na_2SO_4$, filtered and concentrated to afford a crude solid. This solid was dissolved in 95% EtOH (430 mL) using a steam bath to warm the solution. The solution was allowed to cool, causing the product to precipitate from solution. The product was removed by filtration and the solid was washed with cold EtOH (3×150 mL). A second crop was obtained after allowing the mother liquor to stir at RT overnight.

This product was dissolved in anhydrous DMF (3.0 L), cooled to 0° C. and placed under an atmosphere of $N_2$. To this solution was added in small portions sodium hydride (60% in mineral oil, 60.2 g, 1.51 mol, 1.3 eq.). After the addition was complete, the mixture was stirred for an additional 10 min. To this mixture was added drop wise via an addition funnel methyl iodide (250 g, 1.76 mol, 1.5 eq.). After the addition was complete, the cooling bath was removed and the mixture was allowed to stir at RT overnight. The mixture was then concentrated in vacuo (p=10 torr, bath temp=55-60° C.) to remove ca. 2.5 L of DMF. Some solids precipitated from the solution. The product was partitioned between 5 L ice water, 5 L $Et_2O$ and 500 mL of EtOAc. The organic layer was separated. The aqueous layer was extracted with $Et_2O$ (2×1 L). The combined organic layers were washed with brine (2×1 L), dried over $Na_2SO_4$, filtered and concentrated. The oily solid was stirred with hexanes using a wire stir blade to powderize the solid. The solid was removed by filtration and washed with hexanes (2×250 mL). The solid was dissolved in hexanes/EtOAc (1:1, 450 mL) using a steam bath to warm the mixture. An off white precipitate formed on cooling and was filtered off to provide A4. The remaining mother liquor was purified via flash chromatography ($SiO_2$: 1:1 hexanes:EtOAc) to afford additional A4.

Step 3: To a solution of A4 (12.4 g, 54 mmol) in THF (120 mL) at −78° C. was added n-BuLi (2.5 M in hexanes, 21.6 mL, 54 mmol). The reaction was stirred at −78° C. for 45 minutes after which time A2 (8.3 g, 36 mmol) in THF (30 mL) was added via cannula. The reaction was stirred at −78° C. for 1 hour. Saturated $NH_4Cl_{(aq)}$ (100 mL) was added and the reaction allowed to warm to room temperature. The mixture was extracted with EtOAc. The combined organic layers were washed with water and brine. The organic layer was dried ($NaSO_4$), filtered, and concentrated in vacuo. The residue was purified by silica gel chromatography (0-50% EtOAc/hex) to provide A5. The impure fractions were repurified by silica gel chromatography (30-50% EtOAc/hex) to provide additional A5.

Step 4: To A5 (6.8 g, 15 mmol) in DCM (50 mL) and MeOH (50 mL) was added HCl in dioxane (4.0 M, 17 mL), 69 mmol). The reaction was stirred at room temperature for 1 h and then concentrated in vacuo to provide A6 which was used without further purification.

Step 5: To A6 (6.7 g, 19 mmol) in DCM (50 mL) was added TFA (50 mL) and 2-mercaptoacetic acid (6.6 mL, 94 mmol). The reaction was stirred at room temperature for 14 h. The reaction was concentrated in vacuo and 1N $HCl_{(aq)}$ was added. The mixture was extracted with ether. The aqueous layer was then basified with solid potassium carbonate. The mixture was then extracted with EtOAc. The EtOAc layers were washed with water and brine, dried ($Na_2SO_4$), filtered, and concentrated in vacuo to provide A7. The residue was used without further purification.

Step 6: To A7 (4.4 g, 19 mmol) in DCM (200 mL) was added benzyl isothiocyanate (3.1 mL, 23 mmol). The reaction was stirred at room temperature for 1 hour and then concentrated in vacuo. The residue was purified by silica gel chromatography (0-50% EtOAc/hex) to provide A8.

Step 7: To A8 (5.0 g, 13 mmol) in MeOH (50 mL) was added sodium methoxide in methanol (25 wt %, 7.9 mL, 22 mmol). The reaction was stirred at room temperature for 1 hour after which 1N $HCl_{(aq)}$ (20 mL) was added. The mixture was concentrated in vacuo and water was added. The mixture was extracted with EtOAc. The combined organic layers were washed with water and brine, dried ($MgSO_4$), filtered, and concentrated in vacuo. The residue was purified by silica gel chromatography (30-80% EtOAc/hex) to provide A9.

Step 8: To A9 (3.7 g, 13 mmol) in EtOH (100 mL) was added potassium carbonate (1.9 g, 14 mmol) followed by methyl iodide (0.86 mL, 14 mmol) in EtOH (10 mL). The reaction was stirred at room temperature for 3 h. The reaction was filtered and the filtrate concentrated in vacuo. The residue was purified by silica gel chromatography (50-100%) to provide A10.

Step 9: To A10 (1.0 g, 4.2 mmol) in TFA (10 mL) was added N-iodosuccinimide (1.4 g, 6.2 mmol). The reaction was warmed to 60° C. and stirred for 1 h. The reaction mixture was poured into ice water and solid potassium carbonate was added to basify solution. The mixture was extracted with EtOAc. The combined organic layers were washed with water and brine, dried ($MgSO_4$), filtered, and concentrated in vacuo. The residue was purified by silica gel chromatography (50-100% EtOAc/hex) to provide A11.

Step 10: To A11 (0.55 g, 1.4 mmol) in DCM (20 mL) was added TEA (0.40 mL, 2.9 mmol) and $(Boc)_2O$ (0.62 g, 2.9 mmol). The reaction was stirred at room temperature for 18 h. The reaction was loaded directly onto a silica gel column and dried with nitrogen. The silica gel column was then eluted with 0-25% EtOAc/hex to provide A12.

TABLE 2

The following compounds were prepared using similar procedures to that described in Method A, steps 1-8 and 10, using the appropriate starting materials.

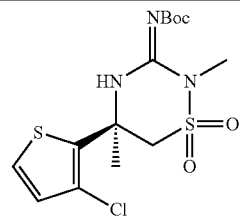

A13

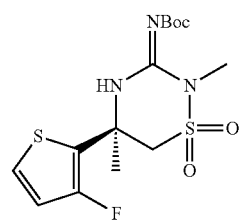

A14

TABLE 2-continued

The following compounds were prepared using similar procedures to that described in Method A, steps 1-8 and 10, using the appropriate starting materials.

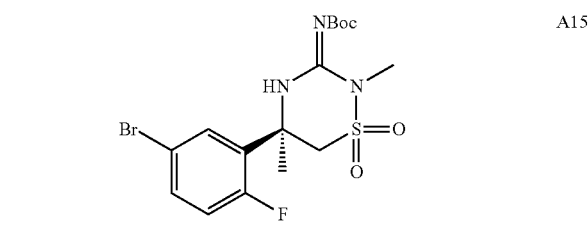

A15

Method B

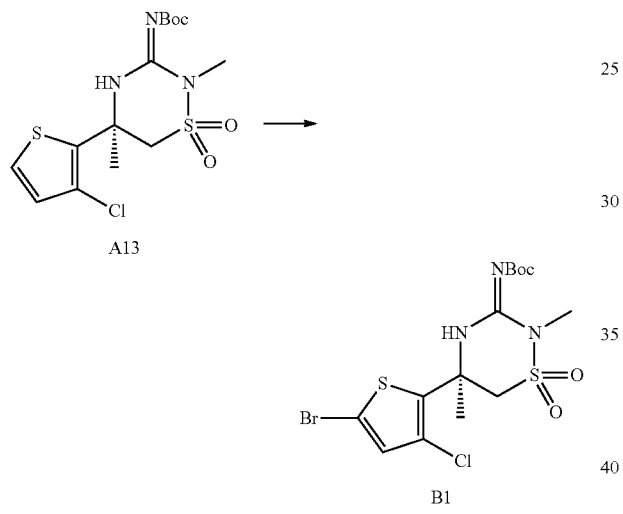

To a solution of the thiophene A13 (2.2 g, 5.6 mmol) in DMF under an atmosphere of $N_2$ was added NBS (2.7 g, 15 mmol). The resultant solution was heated to 50° C. with stirring for 8 hours. The solution was cooled to RT. To the solution was added an aqueous solution of $NaHCO_3$ and $Na_2S_2O_5$. The aqueous layer was extracted EtOAc. The organic layer was washed with sat $NaHCO_3$ $_{(aq.)}$ (2×). The organic layer was dried over $Na_2SO_4$, filtered and concentrated. The crude product was purified via flash chromatography ($SiO_2$: gradient elution 100:0 to 83:17 hexanes:EtOAc) to afford the bromothiophene B1.

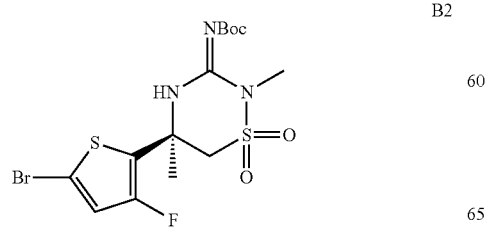

The bromothiophene B2 was prepared in a similar manner as B1 in Method B starting from the fluorothiophene A14.

Method C

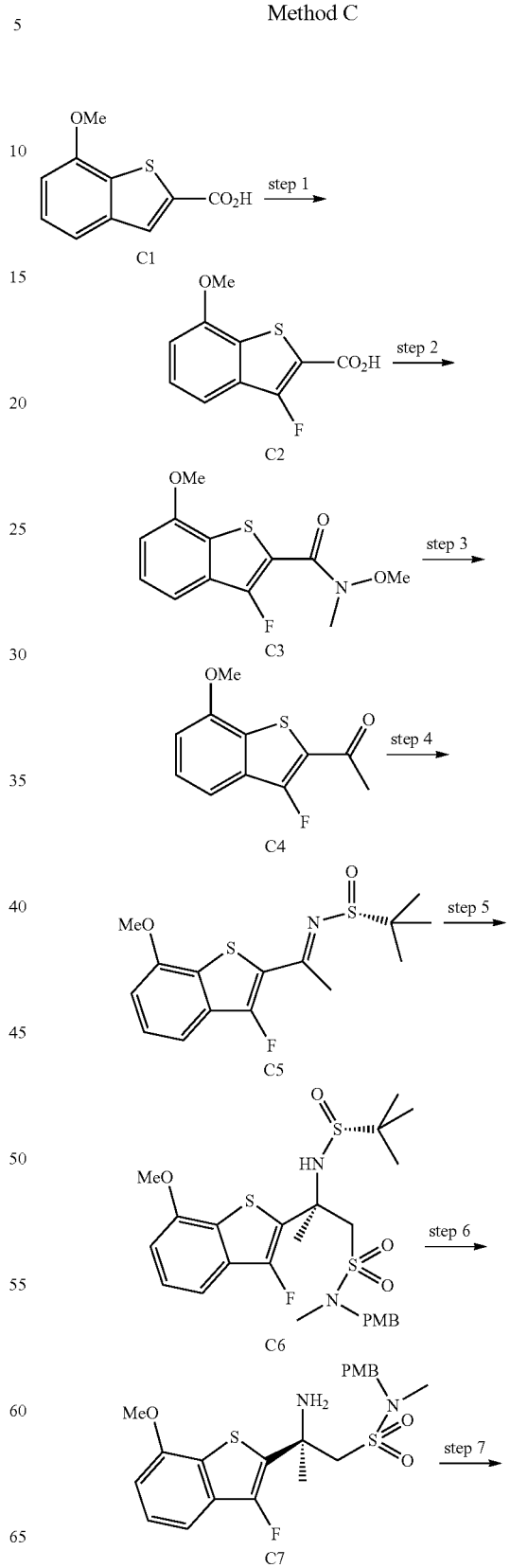

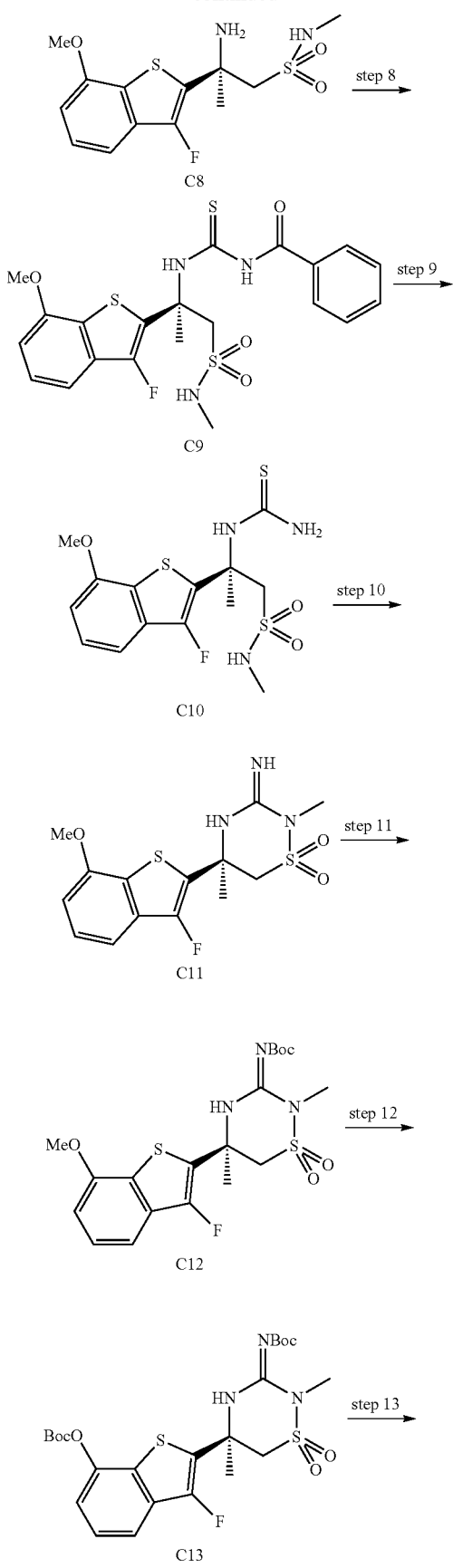

Step 1: To a solution of C1 (14.3 g, 69 mmol) in THF (450 mL) at −78° C. was slowly added t-BuLi (1.7 M, 81 mL, 137 mmol). The resultant mixture was stirred at −78° C. for 1 h. Then a solution of N-fluorobenzenesulfonimide (48 g, 151 mmol) in THF (150 mL) was added by cannula. The mixture was gradually warmed up to RT over 2 hrs. The mixture was stirred at RT for 1 hr. After that time, the mixture was quenched with 1N HCl to adjust to pH 3. The mixture was then diluted with EtOAc, and water. The layers were separated and the organic layer was dried and concentrated to provide a crude solid. The crude solid product was washed with DCM (3×) to provide C2.

Step 2: A solution of C2 (11.1 g, 49 mmol), EDCI (9.8 g, 51 mmol), N-methylmorpholine (5.2 g, 51 mmol), and N,O-dimethylhydroxylamine hydrochloride (5.0 g, 51 mmol) in DCM (150 mL) was stirred at RT for 2 days. The mixture was partitioned between 1N HCl and DCM. The organic layer was separated, dried and concentrated to afford the crude product C3 that was carried on without further purification.

Step 3: To a solution of C3 (16.5 g, 61.5 mmol) in THF (250 mL) at −78° C. was added MeMgBr (3 M, 37 mL, 111 mmol) slowly. The cold bath was removed after 1 hour and the mixture was stirred at RT for 3 h. Quenched the mixture with sat. NH$_4$Cl, and extracted with EtOAc. The organic layer was separated, dried, and concentrated. The crude was purified by flash chromatography (5% EtOAc/Hex) three times to afford C4.

Step 4: A mixture of C4 (11.3 g, 50.2 mmol), (R)-2-methylpropane-2-sulfinamide (6.69 g, 55.2 mmol) and titanium (IV)ethoxide (23.2 mL, 110 mmol) in THF was heated to reflux and stirred for 16 h. After that time, additional (R)-2-methylpropane-2-sulfinamide (1.2 g, 10 mmol) and titanium (IV)ethoxide (2.1 mL, 10 mmol) were added and the mixture was heated to reflux for an additional 8 hours. Water was added to the mixture followed by the addition of EtOAc. The resultant mixture was filtered through a pad of Celite and the organic layer was separated, dried and concentrated. The crude product was purified by flash chromatography (SiO$_2$; 15% EtOAc/hexanes) to afford C5.

Step 5: To a −78° C. solution of A4 (14.5 g, 63.2 mmol) in THF (250 mL) was added nBuLi (2.5 M in hexanes, 25.3 mL, 63.2 mmol). The mixture was stirred at −78° C. for an hour. To the resultant solution was added via cannula a precooled (−78° C.) solution of C5 (13.8 g, 42.1 mmol) in THF (50 mL). The resultant mixture was stirred at −78° C. for 4 hr. After that time, the reaction was quenched with water and the mixture was slowly warmed up to RT. The mixture was then extracted with EtOAc. The organic layer was dried and concentrated. The crude product was purified by flash chromatography (SiO$_2$; gradient elution 35-50% EtOAc/hexanes) to afford C6.

Step 6: To a solution of C6 (21.2 g, 38.1 mmol) in CH$_2$Cl$_2$ was added a solution of HCl (4 N in dioxane, 57.1 mL, 228 mmol). The resultant solution was stirred at RT for 2 h. After that time the solution was concentrated to afford C7 that was carried on to the next step.

Step 7: To C7 (17.2 g, 38 mmol) in CH$_2$Cl$_2$ (100 mL) was added TFA (100 mL) and 2-mercaptoacetic acid (20 mL, 288 mmol). The reaction was stirred at room temperature for 16 h. To the solution was added sat NaHCO$_3$, solid NaOH and K$_2$CO$_3$ to basify the aqueous layer. The mixture was then extracted with EtOAc. The EtOAc layers were washed with water and brine, dried (Na$_2$SO$_4$), filtered, and concentrated in vacuo to provide C8. The residue was used without further purification.

Step 8: To C8 (12.7 g, 38 mmol) in CH$_2$Cl$_2$ (200 mL) was added benzyl isothiocyanate (6.7 mL, 50 mmol). The reaction was stirred at room temperature for 16 hours and then concentrated in vacuo to afford C9 that was carried on without further purification.

Step 9: To C9 (19 g, 38 mmol) in MeOH (150 mL) was added sodium methoxide in methanol (25 wt %, 22 mL, 38 mmol). The reaction was stirred at room temperature for 2 hours. The mixture was concentrated in vacuo and sat. NaHCO$_3$ was added. The mixture was extracted with CH$_2$Cl$_2$. The organic layer was dried (MgSO$_4$), filtered, and concentrated in vacuo to afford C10 that was used without further purification.

Step 10: To C10 (15 g, 38 mmol) in EtOH (150 mL) was added methyl iodide (2.9 mL, 46 mmol). The reaction was stirred at room temperature overnight. The mixture was concentrated in vacuo and sat. NaHCO$_3$ was added. The mixture was extracted with EtOAc. The organic layer was dried, filtered, and concentrated in vacuo. The residue was taken up in EtOH (150 mL) and the resultant solution was heated to reflux for 2 hours. The mixture was concentrated in vacuo and sat. NaHCO$_3$ was added. The mixture was extracted with EtOAc. The organic layer was dried, filtered, and concentrated in vacuo to afford C11 that was used without further purification.

Step 11: Compound C11 was converted to C12 using a method similar to that described in Method A Step 10.

Step 12: To a 0° C. solution of C12 (6.0 g, 13 mmol) in toluene (100 mL) was added slowly a solution of BBr$_3$ (1M, 53 mL, 53 mmol). After 5 mins the cold bath was removed and the mixture was stirred at RT for 2 hrs. The mixture was quenched with water, extracted with EtOAc. The organic layer was separated. The aqueous layer was neutralized by sat. NaHCO$_3$, and solid K$_2$CO$_3$ followed by extraction with EtOAc. The combined organic layers were dried and concentrated. To the crude product was added DCM (100 mL), Boc$_2$O (5.8 g, 26 mmol) and iPr$_2$NEt (8.5 g, 66 mmol). The mixture was stirred at RT overnight. To the mixture was then added catalytic DMAP and stirred for an additional 1 hour. To the mixture was added 1 M HCl. The aqueous layer was extracted with DCM. The organic layer was dried and filtered. The crude product was purified by flash chromatography (20% EtOAc/hexanes) to afford C13.

Step 13: To a solution of C13 (5.7 g, 10 mmol) in DCM (50 mL) was added NaOMe (4.5 g, 21 mmol). The mixture was stirred at RT for 2 h. To the mixture was added 1 N HCl. The aqueous layer was extracted with DCM. The organic layer was dried and concentrated. To the residue was added pyridine (40 mL) and trifluoromethanesulfonic anhydride (3.5 g, 12 mmol). The mixture was stirred at RT for 2 h. The mixture was partitioned between 1 N HCl and DCM. The organic layer was separated, dried and concentrated. The crude product was purified by flash chromatography (20% EtOAc/hexanes) to afford C14.

Method D

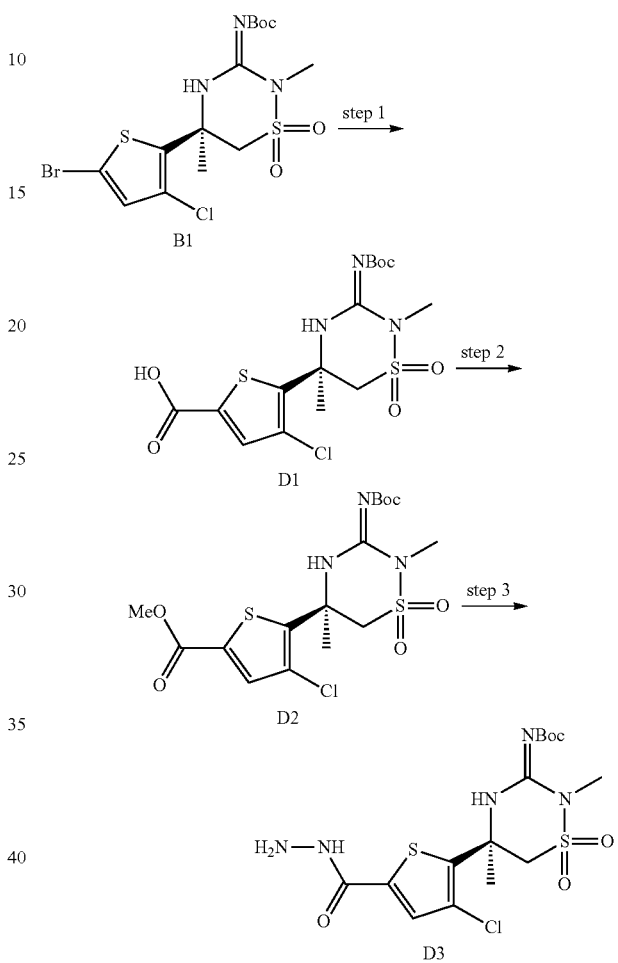

Step 1: To B1 (1.34 g, 2.83 mmol) in THF (9.2 mL) at 0° C. was added methylmagnesium chloride (3.0 M in THF, 1.18 mL, 3.54 mmol). The reaction was stirred for 30 minutes at 0° C. and then cooled to −78° C. n-butyllithium (2.5 M in hexanes, 2.55 mL, 6.38 mmol) was added over 10 minutes. The reaction was stirred for 1 hour at −78° C. and then CO$_2$ gas was bubbled through the reaction. The cold bath was taken away and the reaction allowed to warm to room temperature while continuing to bubble CO$_2$ gas through the mixture. To the mixture was added 1N HCl$_{(aq.)}$ and the mixture was extracted with EtOAc. The combined organic layers were washed with water and brine, dried (MgSO$_4$), filtered, and concentrated in vacuo. The residue was purified by silica gel chromatography (0-80% EtOAc/hex over 30 minutes) to provide the carboxylic acid D1.

Step 2: To D1 (3.0 g, 6.9 mmol) in DCM (19 mL) and methanol (5 mL) at 0° C. was added TMS-diazomethane (2.0 M, 3.6 mL, 7.3 mmol) [Gas Evolution]. The reaction was stirred at room temperature for 3.5 hours and then concentrated in vacuo. The residue was purified by silica gel chromatography (0-20% EtOAc/hex) over 30 minutes to provide the ester D2.

Step 3: To the ester D2 (2.8 g, 6.2 mmol) in ethanol (62 mL) was added hydrazine hydrate (64%/wt, 15 mL, 200 mmol). The reaction was stirred at room temperature for 20 minutes and then concentrated in vacuo to provide the hydrazide D3.

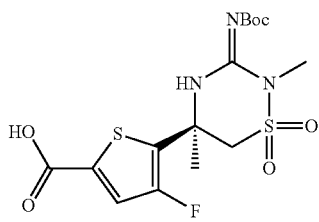

D4

The carboxylic acid D4 was prepared in a similar manner as D1 in Method D except that the bromide B2 was used instead of B1 in step 1.

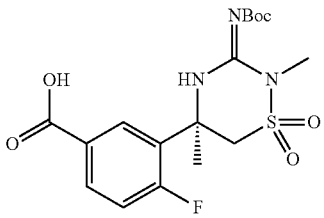

D5

The carboxylic acid D5 was prepared in a similar manner as D1 in Method D except that the bromide A15 was used instead of B1 in step 1.

Method E

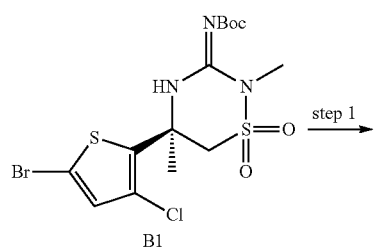

B1

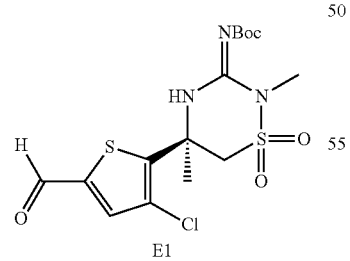

E1

The aldehyde E1 was formed in a similar manner as the carboxylic acid D1 in Method D except that DMF was added to the solution instead of bubbling $CO_2$ gas through the mixture in step 1. The aldehyde was purified by silica gel chromatography (0-25% EtOAc/hex over 20 minutes) to provide E1.

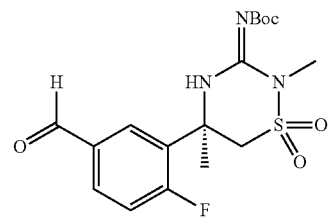

E2

The aldehyde E2 was prepared in a similar fashion as E1 in Method E except that the bromide A15 was used instead of the bromide B1.

Method F

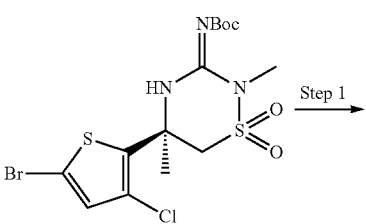

B1

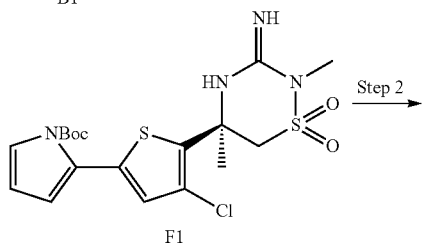

F1

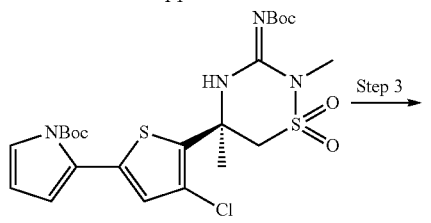

F2

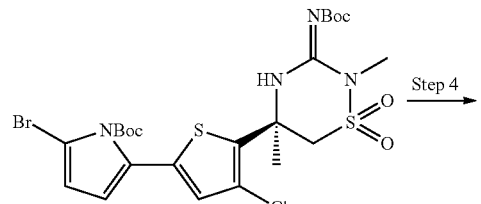

F3

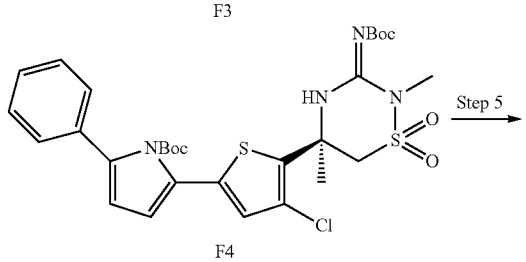

F4

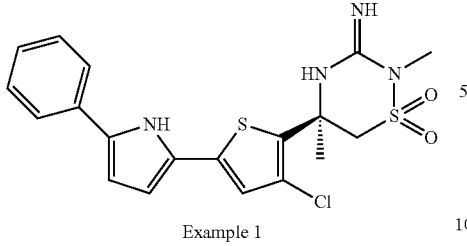

Example 1

Step 1: To B1 (1.0 g, 2.1 mmol) in dioxane (6.8 mL) and water (1.7 mL) was added (1-(tert-butoxycarbonyl)-1H-pyrrol-2-yl)boronic acid (0.67 g, 3.2 mmol) followed by cesium carbonate (1.3 g, 4.0 mmol). Nitrogen was bubbled through the reaction for 5 minutes. Tetrakis(triphenylphosphine)palladium(0) (0.24 g, 0.21 mmol) was added and nitrogen was bubbled through the mixture for ~1 minute. The reaction was warmed to 90° C. and stirred for 5.5 h. Water was added to the cooled reaction and the mixture was extracted with EtOAc. The combined organics were washed with water and brine, dried (MgSO$_4$), filtered, and concentrated in vacuo. The residue was purified by silica gel chromatography (0-85% EtOAc/hex over 30 minutes) to provide F1.

Step 2: To F1 (0.79 g, 1.7 mmol) in DCM (6 mL) was added (Boc)$_2$O (0.56 g, 2.6 mmol). The reaction was stirred at room temperature for 21 h and then concentrated in vacuo. The residue was purified by silica gel chromatography (0-15% EtOAc/hex over 30 minutes and then 15-25% over the next 15 minutes) to provide F2.

Step 3: To F2 (0.31 g, 0.55 mmol) in THF (2.7 mL) at 0° C. was added NBS (0.097 g, 0.55 mmol). The reaction was removed from the cold bath and stirred for 1 h. Water was added and the mixture was extracted with EtOAc. The combined organics were washed with water and brine, dried (MgSO$_4$), filtered, and concentrated in vacuo. The residue was purified by silica gel chromatography (0-20% EtOAc/hex over 30 minutes) to provide F3.

Step 4: To F3 (0.15 g, 0.23 mmol) in t-BuOH (0.78 mL) was added phenylboronic acid (0.052 g, 0.42 mmol) and aqueous potassium carbonate (2M, 0.17 mL, 0.35 mmol). Nitrogen was bubbled through the reaction mixture for 5 minutes. Tetrakis(triphenylphosphine)palladium(0) (0.054 g, 0.047 mmol) was added and nitrogen was bubbled through the reaction mixture for an additional 10 minutes. The reaction was warmed to 70° C. and stirred for 26 h. Water was added to the cooled reaction and the mixture was extracted with EtOAc. The combined organics were washed with water and brine, dried (MgSO$_4$), filtered, and concentrated in vacuo. The residue was taken up into DCM (1.5 mL) and (Boc)$_2$O (0.10 g, 0.47 mmol) was added. The reaction was stirred at room temperature for 15 h. The reaction was concentrated in vacuo and purified directly by silica gel chromatography (0-25% EtOAc/hex over 30 minutes) to provide F4.

Step 5: To F4 (0.084 g, 0.13 mmol) in DCM (1 mL) was added TFA (1 mL). The reaction was stirred at room temperature for 15 minutes. The reaction was diluted with DCM and saturated NaHCO$_3$ was added to adjust the pH to pH~8. The mixture was extracted with DCM. The combined organics were washed with water and brine, dried (MgSO$_4$), filtered, and concentrated in vacuo. The residue was purified by preparative silica gel TLC (1000 μM, 5% MeOH/DCM) followed by SFC purification (OJ-H column, 1:1 MeOH/CAN+ 0.2% diisopropyl amine) to provide Example 1.

Method G

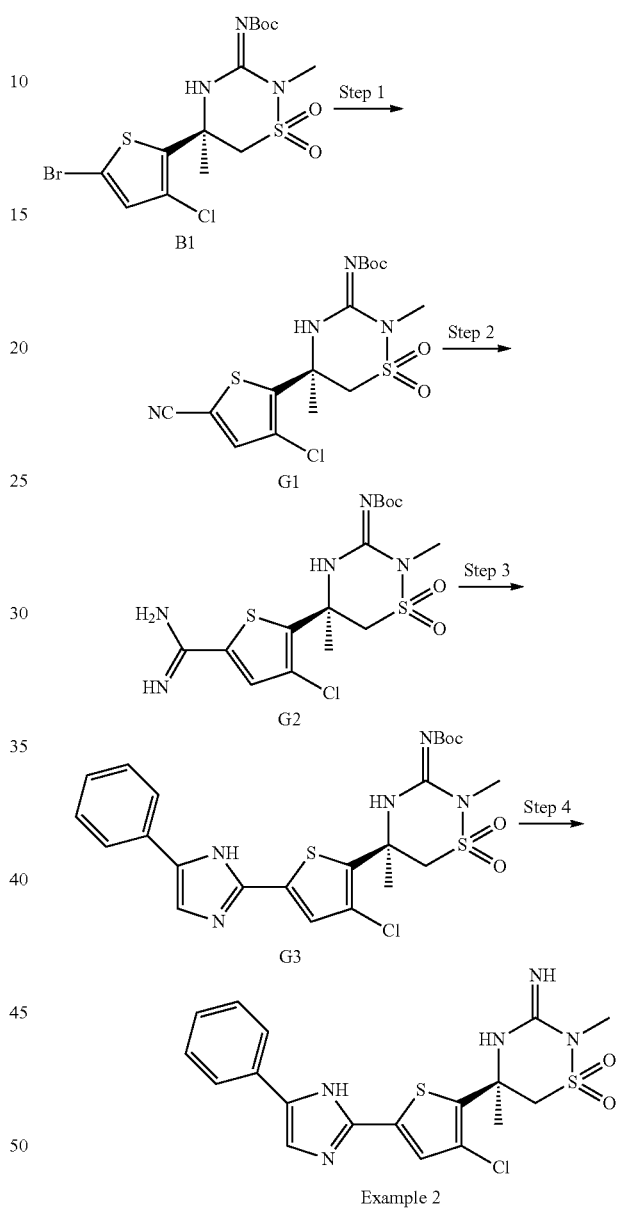

Example 2

Step 1: To the bromide B1 (1.0 g, 2.1 mmol) in dimethylacetamide (11 mL) was added zinc (0.15 g, 2.3 mmol) and zinc cyanide (0.15 g, 1.3 mmol). Nitrogen was bubbled through the reaction mixture for 10 minutes after which PdCl$_2$(dppf) (0.31 g, 0.42 mmol) was added. Nitrogen was bubbled through the reaction mixture for 5 additional minutes. The reaction placed in a preheated oil bath (80° C.) and stirred for 4.5 h. To the cooled reaction was added 1N HCl. The mixture was extracted with EtOAc. The combined organics were washed with water and brine, dried (MgSO$_4$), filtered, and concentrated in vacuo. The residue was purified by silica gel chromatography (0-40% EtOAc/hex over 30 minutes) to provide G1.

Step 2: To G1 (0.23 g, 0.55 mmol) in MeOH (0.5 mL) was added sodium methoxide (25% solution in MeOH, 0.013 mL, 0.055 mmol). The reaction was stirred at room temperature for 2.5 h. The reaction was diluted with additional MeOH (0.5 mL) and ammonium chloride (0.034 g, 0.64 mmol) was added. The reaction was stirred at room temperature for 16 h. The reaction was filtered and the filtrate was concentrated in vacuo to provide G2 (0.26 g) that was used directly without further purification.

Step 3: To G2 (0.13 g, 0.29 mmol) in DMF (1 mL) was added 2-bromo-1-phenylethanone (0.089 g, 0.45 mmol) and potassium carbonate (0.12 g, 0.89 mmol). Stirred at room temperature for 4 h. EtOAc was added and the mixture was washed with saturated NH$_4$Cl, water and brine. The organic layer was dried (MgSO$_4$), filtered, and concentrated in vacuo. The residue was purified by silica gel chromatography (0-40% EtOAc/hex over 30 minutes). The product was further purified by preparative silica gel TLC (2×1000 μM, 40% EtOAc/hex). The product was then further purified by preparative silica gel TLC (1000 μM, 15% EtOAc/DCM) to provide G3.

Step 4: To G3 (0.020 g, 0.037 mmol) in DCM (1 mL) was added TFA (0.3 mL). The reaction was stirred at room temperature for 1 h. The reaction was concentrated in vacuo to provide Example 2 as a TFA salt.

Example 3

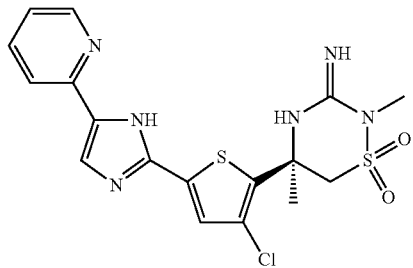

Example 3 was prepared in a similar manner as Example 2 in Method G except that 2-bromo-1-(pyridin-2-yl)ethanone was used instead of 2-bromo-1-phenylethanone in step 3.

Method H

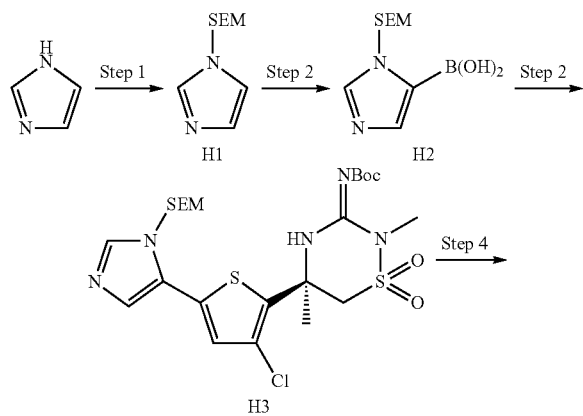

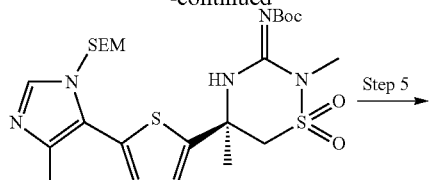

H4

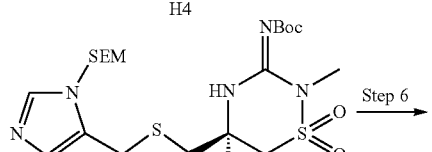

H5

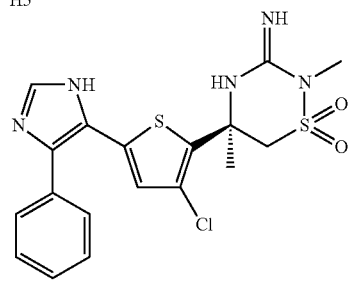

Example 4

Step 1: To imidazole (3.0 g, 44 mmol) in DMF (60 mL) was added NaH (60% dispersion in mineral oil, 1.7 g, 44 mmol) at room temperature. The reaction was stirred at room temperature for 1.5 h and then (2-(chloromethoxy)ethyl)trimethylsilane (7.8 g, 47 mmol) was added drop wise. The reaction was stirred at room temperature for 1 h. Water was added and the mixture was extracted with EtOAc. The combined organic layers were washed with water and brine, dried (MgSO$_4$), filtered, and concentrated in vacuo. The oil was purified by silica gel chromatography (0-100% EtOAc/hex over 45 minutes) to provide H1.

Step 2: To H1 (2.0 g, 10 mmol) in THF (20 mL) at −78° C. was added t-BuLi (1.7 M, 6.9 mL, 12 mmol). The reaction was stirred at −78° C. for 20 minutes after which trimethylsilyl chloride (1.5 mL, 11 mmol) was added. The reaction was removed from the cold bath and stirred for 2 h and then cooled to −78° C. again. t-BuLi (6.9 mL, 12 mmol) was added and the reaction was stirred for 30 minutes after which trimethyl borate (11.2 mL, 100 mmol) was added. The reaction was removed from the cold bath and stirred for 15 h. The reaction mixture was poured into EtOAc-water (4:1). The mixture was acidified to ~pH 7 using 1N HCl. The mixture was extracted with EtOAc. The combined organic layers were washed with brine, dried (MgSO$_4$), filtered, and concentrated in vacuo to provide H2.

Step 3: To the bromide B1 (0.20 g, 0.42 mmol) in t-BuOH (1.4 mL) was added H2 (0.15 g, 0.64 mmol) and aqueous potassium carbonate (2M, 0.32 mL, 0.64 mmol). Nitrogen was bubbled through the reaction mixture for 10 minutes. PdCl$_2$(dppf) (0.062 g, 0.085 mmol) was added and nitrogen was bubbled through the reaction mixture for 5 minutes. The reaction was warmed to 65° C. and stirred for 7 h. The cooled reaction mixture was poured into water and extracted with EtOAc. The combined organic layers were washed with water and brine, dried (MgSO$_4$), filtered, and concentrated in vacuo. The residue was taken up into DCM (1.5 mL) and (Boc)$_2$O (0.092 g, 0.42 mmol) was added. The reaction was stirred at room temperature for 15 h. The reaction was then concentrated in vacuo. The residue was purified by silica gel chromatography (0-50% EtOAc/hex over 30 minutes) to provide a residue that was purified by preparative silica gel TLC (2×1000 μM, 55% EtOAc/hex) to provide H3.

Step 4: To H3 (0.10 g, 0.17 mmol) in DMF (0.5 mL) was added NBS (0.036 g, 0.20 mmol). The reaction was warmed to 50° C. and stirred for 1 h. EtOAc was added to the cooled reaction and the mixture was washed with 10% sodium bisulfite, saturated NaHCO$_3$, water, and brine. The organic layer was dried (MgSO$_4$), filtered, and concentrated in vacuo. The residue was purified by preparative silica gel TCL (2000 μM, 35% EtOAc/hex) to provide H4.

Step 5: To H4 (0.072 g, 0.11 mmol) in dioxane (0.6 mL) and water (0.3 mL) was added phenylboronic acid (0.026 g, 0.22 mmol) and potassium carbonate (0.060 g, 0.43 mmol). Nitrogen was bubbled through the reaction for 5 minutes after which tetrakis(triphenylphosphine)palladium(0) (0.012 g, 0.011 mmol) was added. Nitrogen was bubbled through the reaction for another 5 minutes. The reaction was warmed to 90° C. and stirred for 2.5 h. Water was added to the cooled reaction and the mixture was extracted with EtOAc. The combined organic layers were washed with water and brine, dried (MgSO$_4$), filtered, and concentrated in vacuo. The residue was taken up into DCM (0.3 mL) and (Boc)$_2$O (0.042 g, 0.19 mmol) was added. The reaction was stirred at room temperature for 15 h. The reaction was concentrated in vacuo and the residue was purified by preparative silica gel TLC (1000 μM, 40% EtOAc/hex) to provide H5.

Step 6: To H5 (0.040 g, 0.06 mmol) was added HCl in dioxane (4M, 1 mL, 4 mmol). The reaction was warmed to reflux and stirred for 1 h. The reaction was concentrated in vacuo and the residue was triturated with ether to provide Example 4 as an HCl salt.

Method I

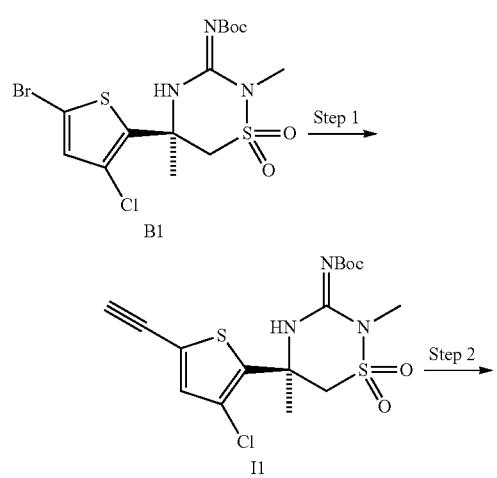

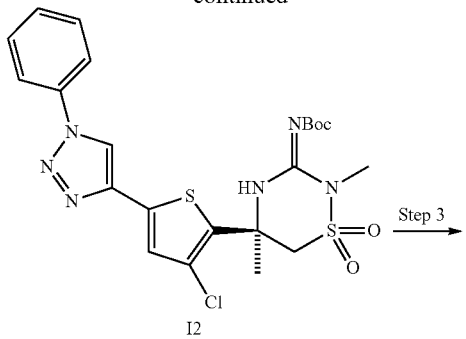

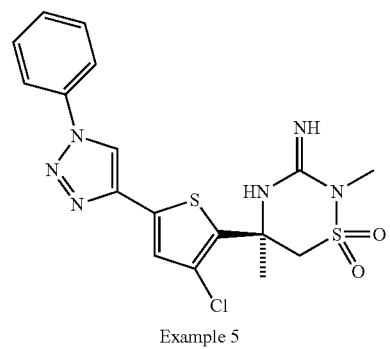

Example 5

Step 1: To B1 (5.0 g, 11 mmol) in THF (53 mL) at room temperature was added bis(triphenylphosphine)palladium (II)dichloride (0.74 g, 1.1 mmol), copper(I)iodide (0.020 g, 1.1 mmol), diisopropylethylamine (8.7 mL, 53 mmol), and trimethylsilylacetylene (3.0 mL, 21 mmol). The reaction was degassed with nitrogen three times. The reaction was then heated to 40° C. and stirred for 3 h. The cooled reaction was diluted with EtOAc and the mixture was washed with saturated NH$_4$Cl, 0.5 N HCl, water, and brine. The organic layer was dried (MgSO$_4$), filtered, and concentrated in vacuo. The residue was taken up into MeOH (50 mL) and 1 M K$_2$CO$_3$ (20 mL) and THF (40 mL) were added. The mixture was stirred at room temperature for 15 h. The organic solvents were removed in vacuo. The mixture was then diluted with EtOAc and washed with water and brine. The organic layer was dried (MgSO$_4$), filtered, and concentrated in vacuo. The residue was purified by silica gel chromatography (0-50% EtOAc) to provide I1.

Step 2: To aniline (0.05 g, 0.54 mmol) in acetonitrile (2 mL) at 0° C. was added tert-butyl nitrite (0.096 mL, 0.81 mmol) and trimethylsilyl azide. The cooling bath was removed and the reaction was stirred for 2.5 h. I1 (0.22 g, 0.52 mmol) was added as a solid followed by cupric sulfate (0.009 g, 0.06 mmol) in water (0.2 mL) and sodium ascorbate (0.030 g, 0.15 mmol). The reaction was stirred for 18 h at room temperature and then concentrated in vacuo. The residue was purified by silica gel chromatography (0-30% EtOAc/hex over 30 minutes) to provide I2.

Step 3: To I2 (0.09 g, 0.17 mmol) in DCM (4 mL) was added TFA (2 mL). The reaction was stirred at room temperature for 2 h and then concentrated in vacuo. The residue was purified by reverse phase chromatography (C18: gradient elution, 90:10:0.1 to 0:100:0.1 water:MeCN:TFA) to provide Example 5 as a TFA salt.

Method J

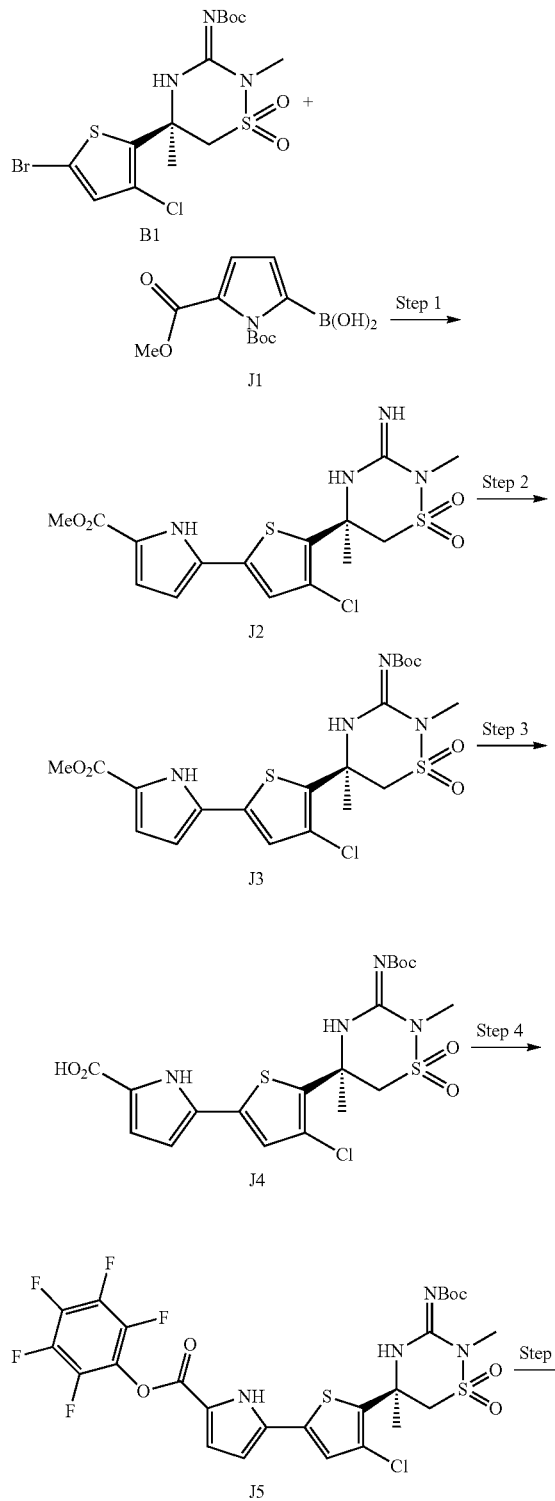

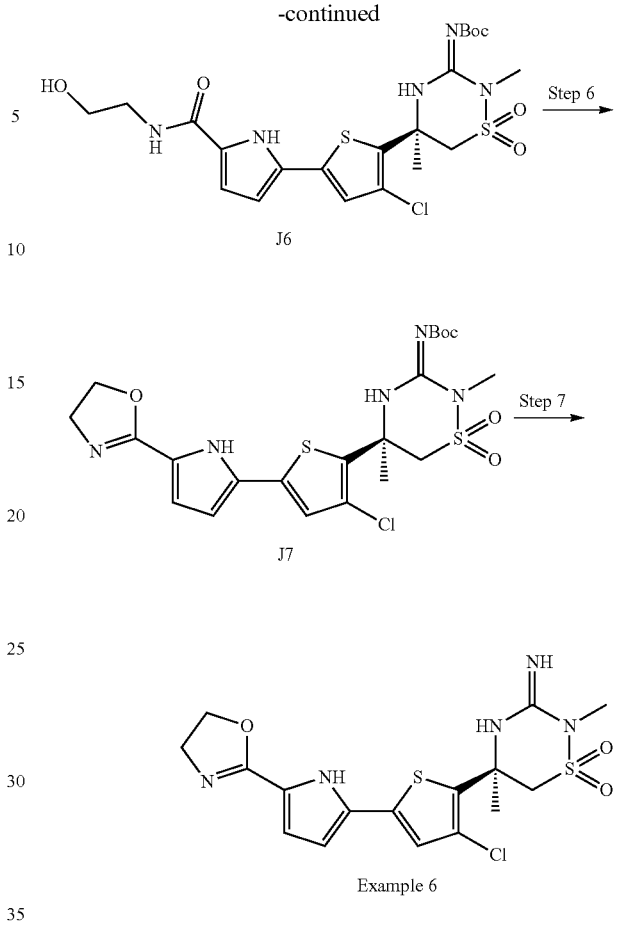

Example 6

Step 1: To B1 (2.5 g, 5.3 mmol) in dioxane (17 mL) was added water (4.2 mL), dicesium carbonate (5.2 g, 16 mmol) and (1-(tert-butoxycarbonyl)-5-(methoxycarbonyl)-1H-pyrrol-2-yl)boronic acid J1 (2.2 g, 8.0 mmol). Nitrogen was bubbled through the reaction for 10 minutes. Tetrakis(triphenylphosphine)palladium(0) (0.62 g, 0.53 mmol) was added and nitrogen was again bubbled through the reaction mixture for 5 minutes. The reaction was warmed to 90° C. and stirred for 2 h. The reaction was cooled to room temperature and water was added. The mixture was extracted with EtOAc. The organics were combined and washed with water and brine, dried (MgSO$_4$), filtered, and concentrated in vacuo. The residue was taken up into DCM (14 mL) and TFA (8 mL) was added. The reaction was stirred at room temperature for 1.5 h and then concentrated in vacuo. The residue was taken up into DCM and washed with saturated NaHCO$_3$, water, and brine. The organic layer was dried (MgSO$_4$), filtered, and concentrated in vacuo. The residue was purified by silica gel chromatography (0-100% EtOAc/hex) over 30 minutes to provide J2.

Step 2: To J2 (2.0 g, 4.8 mmol) in acetonitrile (15 mL) was added N,N-diisopropylethylamine (1.5 mL, 8.4 mmol) and (Boc)$_2$O (2.6 g, 12 mmol). The reaction was stirred at room temperature for 18 h. The reaction was concentrated in vacuo. The residue was taken up into DCM and washed with saturated NaHCO$_3$, water, and brine. The organic layer was dried (MgSO$_4$), filtered, and concentrated in vacuo. The residue was purified by silica gel chromatography (0-30% EtOAc/hex) over 30 minutes to provide J3.

Step 3: To J3 (0.88 g, 1.7 mmol) in THF (6 mL) was added aqueous 2N LiOH (5 mL, 10 mmol). The reaction was warmed to 65° C. and stirred for 7 h. The reaction was cooled and 1N HCl was added. The mixture was extracted with EtOAc. The combined organics were washed with water and brine, dried (MgSO₄), filtered, and concentrated in vacuo. The residue was purified by reverse phase chromatography (150 g C18 column: 5% (2 column volumes), 5-100% (15 column volumes) 0.1% formic acid/acetonitrile//0.1% formic acid/water to provide J4.

Step 4: To J4 (0.10 g, 0.20 mmol) in DMF (1.3 mL) was added pyridine (0.05 mL, 0.60 mmol) followed by perfluorophenyl 2,2,2-trifluoroacetate (0.05 mL, 0.30 mmol). The reaction was stirred at room temperature for 4 h and then additional perfluorophenyl 2,2,2-trifluoroacetate was added (0.10 mL, 0.60 mmol). After stirring for two additional hours EtOAc was added. The mixture was washed with water and brine. The organic layer was dried (MgSO₄), filtered, and concentrated in vacuo. The residue was purified by silica gel chromatography (0-20% EtOAc/hex over 30 minutes) to provide J5.

Step 5: To J5 (0.11 g, 0.16 mmol) in DMF (0.5 mL) was added hydroxyethyl amine (0.011 mL, 0.18 mmol) and TEA (0.046 mL, 0.33 mmol). The reaction was stirred at room temperature for 1.5 h. Saturated NaHCO₃ was added and the mixture was extracted with EtOAc. The combined organic layers were washed with water and brine, dried (MgSO₄), filtered, and concentrated in vacuo provide J6.

Step 6: To J6 (0.09 g, 0.17 mmol) in DCM (1.4 mL) at −20° C. was added deoxofluor (0.033 mL, 0.18 mmol). Stirred for 30 minutes and then added additional deoxofluor (0.010 mL, 0.06 mmol). After stirring for 1 hour, saturated NaHCO₃ was added and the reaction was allowed to warm to room temperature. The mixture was extracted with DCM. The combined organics were washed with water and brine, dried (MgSO₄), filtered, and concentrated in vacuo. The residue was purified by silica gel chromatography (0-70% EtOAc/hex over 30 minutes) to provide J7.

Step 7: To J7 (0.05 g, 0.09 mmol) in DCM (0.3 mL) was added TFA (0.14 g, 1.8 mmol). The reaction was stirred at room temperature for 2 h and then concentrated in vacuo. The residue was taken up into DCM and washed with saturated NaHCO₃, water, and brine. The organic layer was dried (MgSO₄), filtered, and concentrated in vacuo. The residue was purified by reverse phase chromatography (30 g C18 column: 5% (2 column volumes), 5-100% (15 column volumes) 0.1% formic acid/acetonitrile//0.1% formic acid/water to provide Example 6.

Example 7

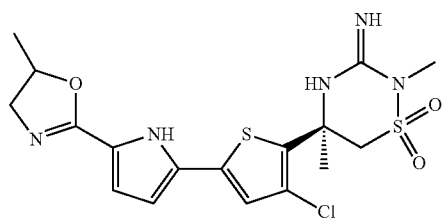 [SMILES: CC1CN=C(c2ccc(-c3cc(Cl)c([C@]4(C)CS(=O)(=O)N(C)C(=N)N4)s3)[nH]2)O1]

Example 7 was prepared in a similar manner as Example 6 in Method J except that 1-amino-2-propanol was used instead of hydroxyethyl amine in Step 5.

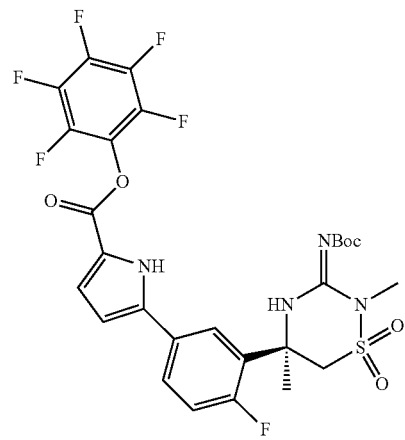

J8 was prepared in a similar manner as J5 in Method J except that the bromide A15 was used instead of the bromide B1 in step 1.

Method K

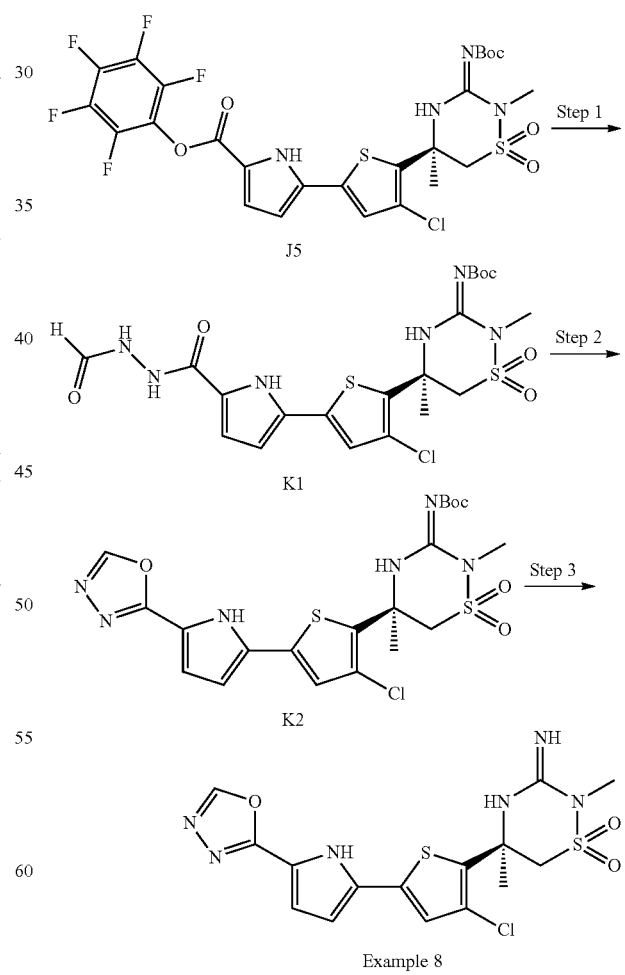

Step 1: To J5 (0.22 g, 0.33 mmol) in DMF (1.1 mL) was added formic hydrazide (0.022 g, 1.1 mmol) and TEA (0.09 mL, 0.66 mmol). The reaction was heated to 50° C. and stirred for 4 h. Another equivalent of formic hydrazide and TEA were added and the reaction was stirred at 50° C. for an additional 18 h. To the cooled reaction mixture was added NaHCO₃. The mixture was extracted with EtOAc. The combined organic layers were washed with water and brine, dried (MgSO₄), filtered, and concentrated in vacuo. The residue was purified by silica gel chromatography (0-5% MeOH/EtOAc over 20 minutes) to provide K1.

Step 2: To K1 (0.085 g, 0.16 mmol) in THF (0.78 mL) was added Burgess reagent (0.11 g, 0.47 mmol). The reaction was warmed to 75° C. and stirred for 1 h. DCM was added to the cooled reaction and the mixture was washed with water and brine, dried (MgSO₄), filtered, and concentrated in vacuo. The residue was purified by silica gel chromatography (0-50% EtOAc/hex over 25 minutes) to provide K2.

Step 3: To K2 (0.015 g, 0.028 mmol) in DCM (0.25 mL) was added TFA (0.044 mL, 0.57 mmol). The reaction was stirred at room temperature for 15 minutes and then concentrated in vacuo to provide Example 8 as a TFA salt.

Example 9

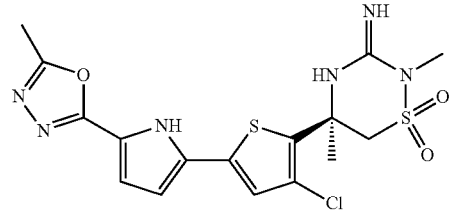 [SMILES: Cc1nnc(-c2ccc(-c3cc(Cl)c([C@]4(C)CS(=O)(=O)N(C)C(=N)N4)s3)[nH]2)o1]

Example 9 was prepared in a similar manner as Example 8 in Method K except that acetohydrazide was used instead of formic hydrazide in step 1.

Example 10

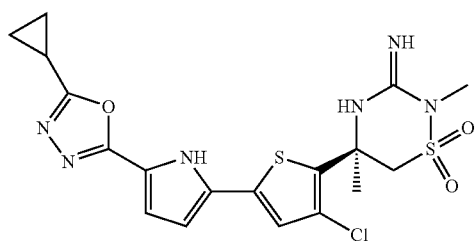 [SMILES: CN1C(=N)N[C@](C)(c2sc(-c3ccc(-c4nnc(C5CC5)o4)[nH]3)cc2Cl)CS1(=O)=O]

Example 10 was prepared in a similar manner as Example 8 in Method K except that cyclopropanecarbohydrazide was used instead of formic hydrazide in step 1.

Example 11

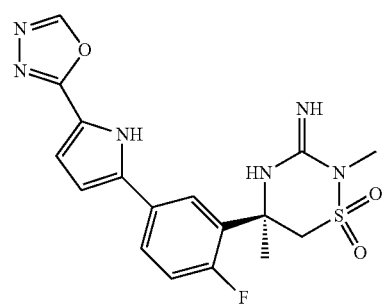

Example 11 was prepared in a similar manner as Example 8 in Method K except that J8 was used instead of J5 in step 1.

Method L

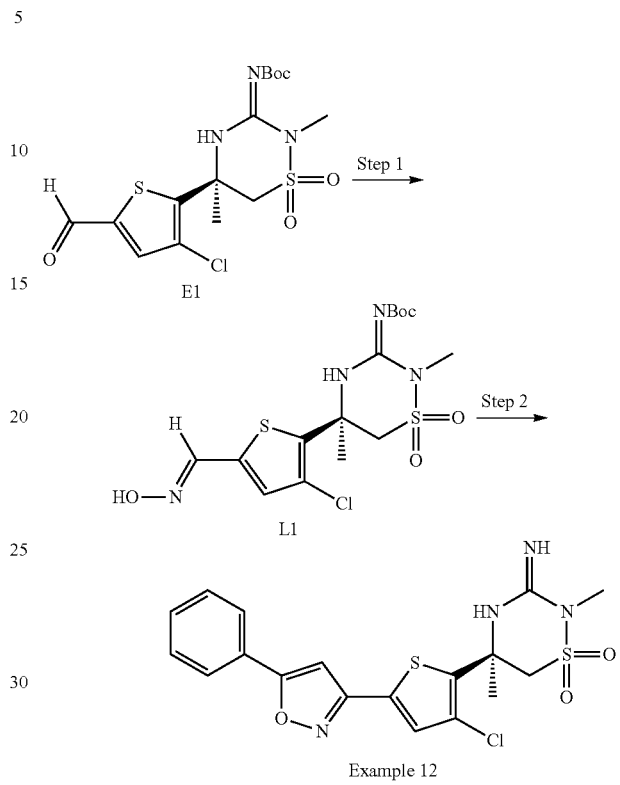

Step 1: To E1 (0.20 g, 0.47 mmol) in ethanol (4.5 mL) was added pyridine (90.0 mL, 0.52 mmol) followed by hydroxyl amine hydrochloride (0.036 g, 0.52 mmol) in water (0.5 mL). The reaction was stirred at 45° C. for 45 minutes. The solvent was removed in vacuo. The residue was taken up into EtOAc and washed with saturated NaHCO₃. The organic layer was dried (MgSO₄), filtered, and concentrated in vacuo to provide L1.

Step 2: To phenylacetylene (0.016 g, 0.15 mmol), iodobenzene diacetate (0.050 g, 0.15 mmol, and TFA (0.002 mL, 0.03 mmol) in MeOH (2 mL) was added L1 (0.061 g, 0.14 mmol). The reaction was stirred at room temperature for 2 h. The reaction was poured into water and extracted with DCM. The combined organics were washed with water and brine, dried (MgSO₄), filtered, and concentrated in vacuo. The residue was purified by reverse phase HPLC (C18: gradient elution, 90:10:0.1 to 0:100:0.1 water:MeCN:TFA) to provide Example 12.

Example 13

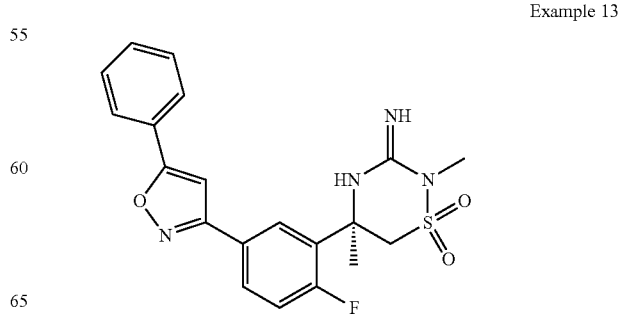

Example 13 was prepared in a similar manner as Example 12 in Method L except that the aldehyde E2 was used instead of aldehyde E1 in step 1.

Method M

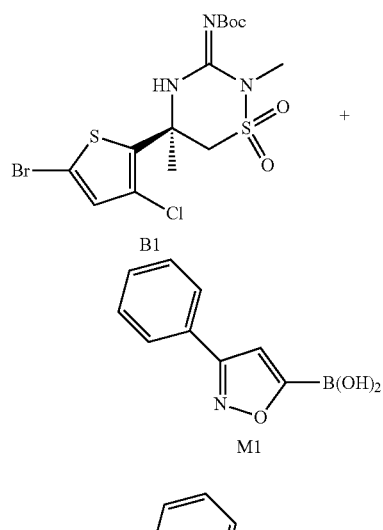

To B1 (0.10 g, 0.21 mmol) in dioxane (1 mL) was added M1 (0.08 g, 0.42 mmol) [J&W Pharmalab, LLC], $PdCl_2(dppf)$ (0.014 g, 0.021 mmol), and $K_3PO_4$ (2.0 M, 0.31 mL, 0.64 mmol). Nitrogen was bubbled through the reaction mixture for 5 minutes. The mixture was heated to 60° C. and stirred for 18 h. The cooled reaction was poured into saturated $NaHCO_3$ and the mixture was extracted with EtOAc. The combined organics were washed with water and brine, dried ($MgSO_4$), filtered, and concentrated in vacuo. The residue was purified by reverse phase chromatography [C18: gradient elution, 90:10:0.1 to 0:100:0.1 water:MeCN:TFA] to provide a mixture of unprotected product and Boc-protected product. The Boc-protected product was taken up into DCM (1 mL) containing TFA. After 1 hour, the reaction was concentrated in vacuo. The residue was combined with previously isolated unprotected product. The mixture was purified by reverse phase chromatography [C18: gradient elution, 90:10:0.1 to 0:100:0.1 water:MeCN:TFA] to provide Example 14.

Example 15

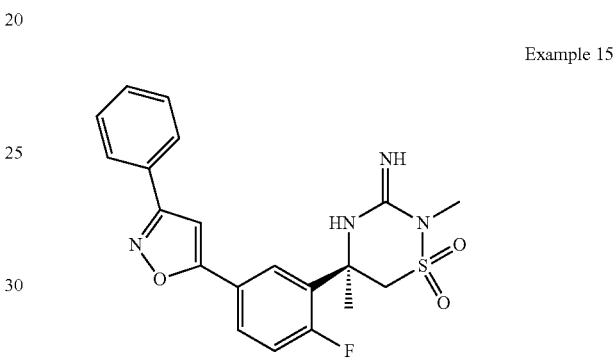

Example 15 was prepared in the same manner as Example 14 in Method M except that A15 was used instead of B1.

TABLE 3

| Ex. number | Example | M + H: Obs. (Exp.) | LCMS Cond. ($t_R$ min) | LCMS method | BACE1 Ki (nM) |
|---|---|---|---|---|---|
| 1 | (structure) | 435 (435) | 2.14 | A | 2.1 |
| 2 | (structure) | 436 (436) | 1.60 | B | 112 |

TABLE 3-continued

| Ex. number | Example | M + H: Obs. (Exp.) | LCMS Cond. (t_R min) | LCMS method | BACE1 Ki (nM) |
|---|---|---|---|---|---|
| 3 | | 437 (437) | 1.41 | B | 470 |
| 4 | | 436 (436) | 1.37 | B | 9034 |
| 5 | | 437 (437) | 1.60 | B | 1985 |
| 6 | | 428 (428) | 1.76 | A | 270 |
| 7 | | 442 (442) | 1.82 | A | 87 |
| 8 | | 427 (427) | 1.87 | A | 2.8 |

TABLE 3-continued

| Ex. number | Example | M + H: Obs. (Exp.) | LCMS Cond. ($t_R$ min) | LCMS method | BACE1 Ki (nM) |
|---|---|---|---|---|---|
| 9 | | 441 (441) | 1.67 | B | 8.1 |
| 10 | | 467 (467) | 1.75 | B | 87 |
| 11 | | 405 (405) | 1.66 | B | 45 |
| 12 | | 437 (437) | 1.65 | B | 1171 |
| 13 | | 415 (415) | 2.41 | B | 910 |

TABLE 3-continued

| Ex. number | Example | M + H: Obs. (Exp.) | LCMS Cond. ($t_R$ min) | LCMS method | BACE1 Ki (nM) |
|---|---|---|---|---|---|
| 14 | 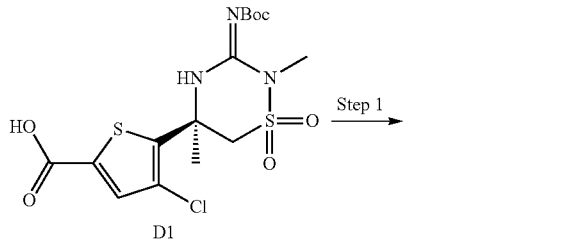 | 437 (437) | 1.67 | B | 943 |
| 15 | 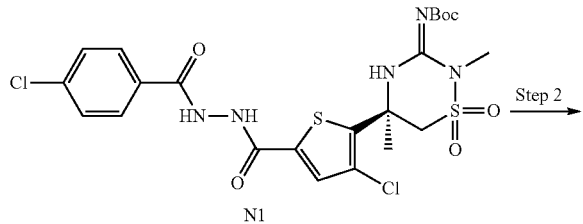 | 415 (415) | 1.61 | B | 326 |

Method N

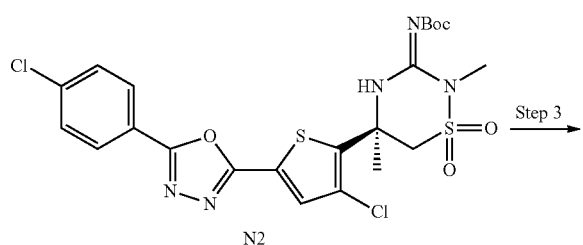

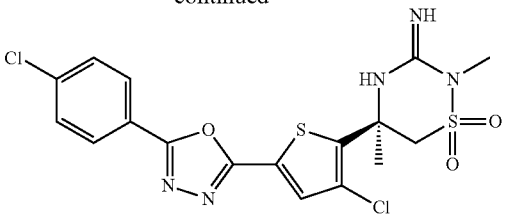

Example 16

Step 1: To the acid D1 (0.17 g, 0.38 mmol) in EtOAc (1.3 mL) was added 4-chlorobenzohydrazide (0.07 g, 0.42 mmol), TEA (0.16 mL, 1.1 mmol), and T3P (50% solution in EtOAc, 0.46 mL, 0.77 mmol). The reaction was stirred at room temperature for 20 h. Water was added and the mixture was stirred vigorously for 30 minutes. The mixture was then extracted with EtOAc. The combined organics were washed with saturated NaHCO$_3$, water, and brine. The organic layer was dried (MgSO$_4$), filtered, and concentrated in vacuo to provide N1 that was used directly in the next step without further purification.

Step 2: To N1 (0.22 g, 0.37 mmol) in THF (1.5 mL) was added Burgess reagent (0.31 g, 1.3 mmol). The reaction was warmed to 65° C. and stirred for 8 h. The cooled reaction was purified directly by silica gel chromatography (0-30% EtOAc/hex over 30 minutes) to provide N2.

Step 3: To N2 (0.033 g, 0.058 mmol) in DCM (0.20 mL) was added TFA (0.067 mL, 0.86 mmol). The reaction was stirred for 1 h at room temperature and then concentrated in vacuo. The residue was Purified by reverse phase chromatography: 5% (2 column volumes), 5-100% (10 column volumes) 0.1% TFA/acetonitrile//0.1% TFA/water) to provide Example 16 as a TFA salt.

The examples in Table 4 were prepared using the procedures described in Method N starting form the carboxylic acid and using the appropriate acyl hydrazide.

TABLE 4

| Ex. number | Carboxylic Acid | Example | M + H: Obs. (Exp.) | LCMS Method; $t_R$ (min) | BACE1 Ki (nM) |
| --- | --- | --- | --- | --- | --- |
| 16 | D1 | | 472 (472) | B 1.69 | 28.82 |
| 17 | D1 | | 468 (468) | B 1.60 | 38.62 |
| 18 | D1 | | 506 (506) | B 1.75 | 58.93 |
| 19 | D4 | | 456 (456) | B 2.10 | 31.95 |
| 20 | D1 | | 438 (438) | B 1.79 | 105.8 |
| 21 | D1 | | 439 (439) | B 1.60 | 554.6 |

TABLE 4-continued

| Ex. number | Carboxylic Acid | Example | M + H: Obs. (Exp.) | LCMS Method; $t_R$ (min) | BACE1 Ki (nM) |
|---|---|---|---|---|---|
| 22 | D1 | | 456 (456) | B 1.83 | 65.54 |
| 23 | D1 | | 463 (463) | B 1.77 | 34.58 |
| 24 | D5 | | 416 (416) | B 1.78 | 9868 |
| 25 | D5 | | 450 (450) | B 1.88 | 2592 |
| 26 | D5 | | 407 (407) | B 1.54 | 1245 |

Method O

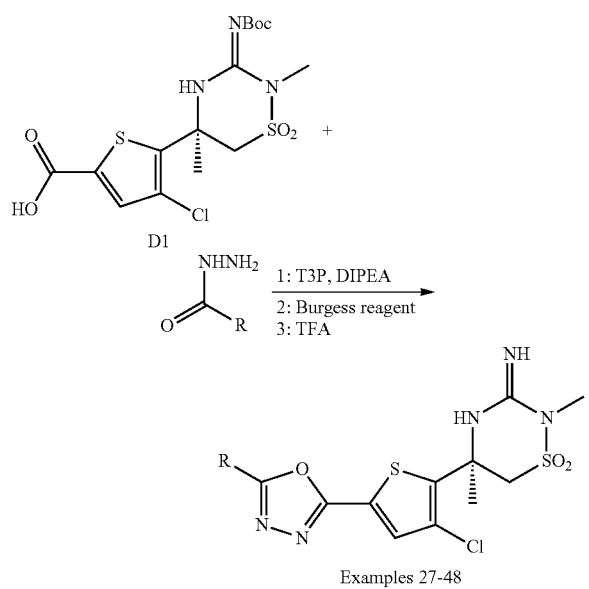

Parallel preparation of Examples 27-48

Step 1 To a set of vials containing a solution of D1 (35 mg, 0.080 mmol) in $CH_2Cl_2$ (1 mL) was added the appropriate acyl hydrazide (1.1 equiv.) and DIEA (31.0 mg, 0.240 mmol). The mixtures were stirred for 5 minutes after which T3P (33.1 mg, 0.104 mmol) (50% solution in EtOAc) was added. The reaction mixtures were stirred at room temperature for 18 h.

Step 2 Water (2 mL) and $CH_2Cl_2$ (2 mL) were added to each reaction and stirring was continued for 5 minutes. The organic layers were separated and concentrated in vacuo.

Step 3 The residues from step 2 were redissolved in $CH_2Cl_2$ (1 mL) and Burgess reagent (28.6 mg, 0.120 mmol) followed by DIEA (31.0 mg, 0.240 mmol) were added. The mixtures were heated at 65° C. for one hour.

Step 4 The reaction mixtures from step 3 were cooled to room temperature and treated with TFA (0.3 mL). After 30 minutes, the reaction mixtures were concentrated in vacuo. Each crude product was redissolved in 1 mL of DMSO and filtered.

Step 5 The DMSO solutions from step 4 were purified by mass triggered HPLC (Waters XBridge C18 column, 5 μm, 30×100 mm, using gradient ranges from 10% initial to 45-70% final [MeCN (0.1% $NH_4OH$)/water (0.1% $NH_4OH$)]) to provide Examples 27-48.

TABLE 5

| Example no. | Structure | Expected M + H (observed) | LCMS Method; $t_R$ (min) | BACE1 Ki (nM) |
| --- | --- | --- | --- | --- |
| 27 | 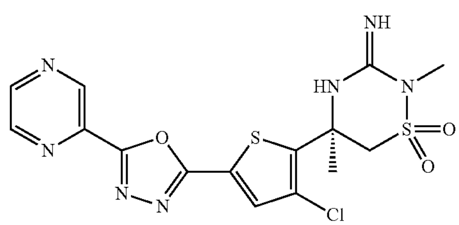 [SMILES: CN1C(=N)N[C@](C)(c2sc(-c3nnc(-c4cnccn4)o3)cc2Cl)CS1(=O)=O] | 440 (440) | C 0.74 | 682.9 |
| 28 | 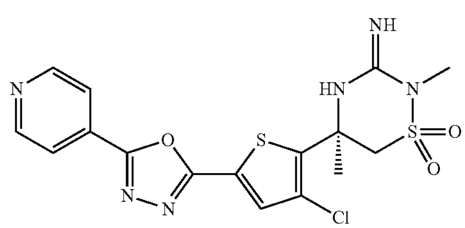 [SMILES: CN1C(=N)N[C@](C)(c2sc(-c3nnc(-c4ccncc4)o3)cc2Cl)CS1(=O)=O] | 439 (439) | C 0.78 | 558.3 |
| 29 | 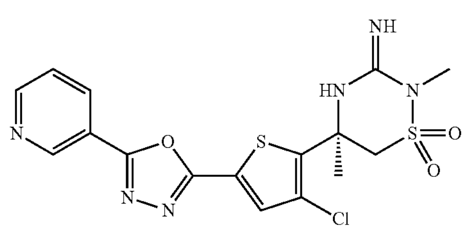 [SMILES: CN1C(=N)N[C@](C)(c2sc(-c3nnc(-c4cccnc4)o3)cc2Cl)CS1(=O)=O] | 439 (439) | C 0.78 | 1046 |

TABLE 5-continued

| Example no. | Structure | Expected M + H (observed) | LCMS Method; $t_R$ (min) | BACE1 Ki (nM) |
|---|---|---|---|---|
| 30 | 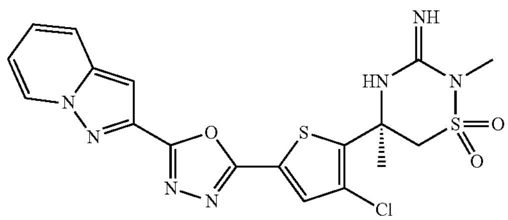 [SMILES: CN1C(=N)N[C@](C)(c2sc(-c3nnc(-c4cc5ccccn5n4)o3)cc2Cl)CS1(=O)=O] | 478 (478) | C 0.89 | 260 |
| 31 | 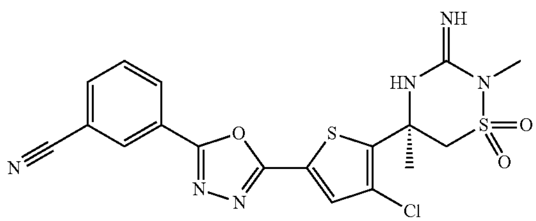 [SMILES: CN1C(=N)N[C@](C)(c2sc(-c3nnc(-c4cccc(C#N)c4)o3)cc2Cl)CS1(=O)=O] | 463 (463) | C 0.92 | 1209 |
| 32 | 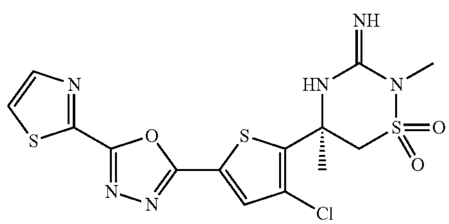 [SMILES: CN1C(=N)N[C@](C)(c2sc(-c3nnc(-c4nccs4)o3)cc2Cl)CS1(=O)=O] | 445 (445) | C 0.81 | 401.9 |
| 33 | 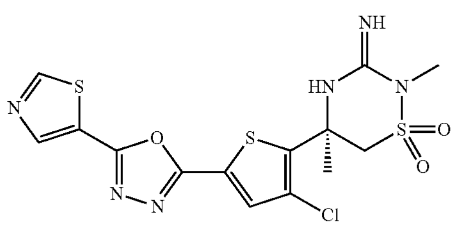 | 445 (445) | C 0.78 | 863.3 |
| 34 | 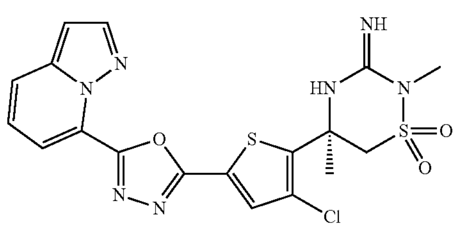 [SMILES: CN1C(=N)N[C@](C)(c2sc(-c3nnc(-c4cccc5ccnn45)o3)cc2Cl)CS1(=O)=O] | 478 (478) | C 0.87 | 561.4 |
| 35 | 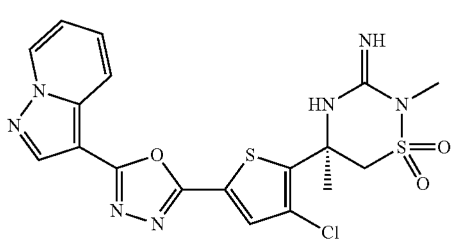 [SMILES: CN1C(=N)N[C@](C)(c2sc(-c3nnc(-c4cnn5ccccc45)o3)cc2Cl)CS1(=O)=O] | 478 (478) | C 0.87 | 2374 |

TABLE 5-continued

| Example no. | Structure | Expected M + H (observed) | LCMS Method; t_R (min) | BACE1 Ki (nM) |
|---|---|---|---|---|
| 36 | 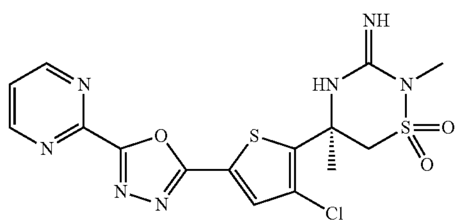 [SMILES: CN1C(=N)N[C@](C)(c2sc(-c3nnc(-c4ncccn4)o3)cc2Cl)CS1(=O)=O] | 440 (440) | C 0.70 | 778.2 |
| 37 | 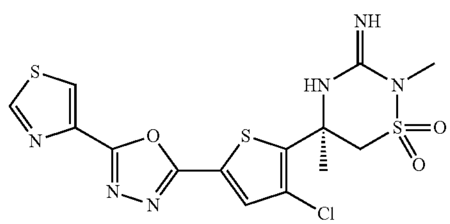 [SMILES: CN1C(=N)N[C@](C)(c2sc(-c3nnc(-c4cscn4)o3)cc2Cl)CS1(=O)=O] | 445 (445) | C 0.76 | 662.1 |
| 38 | 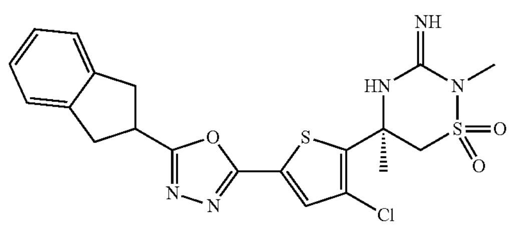 [SMILES: CN1C(=N)N[C@](C)(c2sc(-c3nnc(C4Cc5ccccc5C4)o3)cc2Cl)CS1(=O)=O] | 478 (478) | C 1.05 | 254.6 |
| 39 | 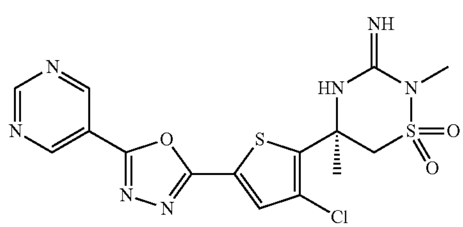 [SMILES: CN1C(=N)N[C@](C)(c2sc(-c3nnc(-c4cncnc4)o3)cc2Cl)CS1(=O)=O] | 440 (440) | C 0.73 | 5400 |
| 40 | 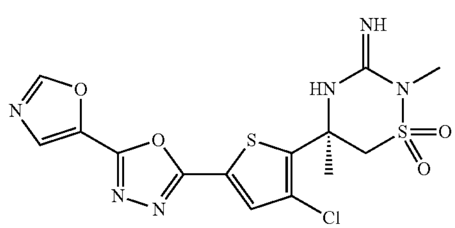 [SMILES: CN1C(=N)N[C@](C)(c2sc(-c3nnc(-c4cnco4)o3)cc2Cl)CS1(=O)=O] | 429 (429) | C 0.74 | 250.3 |
| 41 | 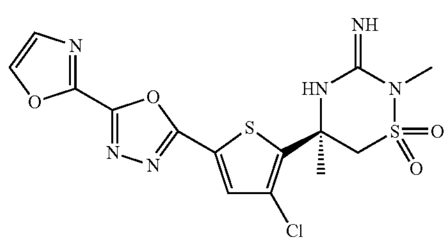 [SMILES: CN1C(=N)N[C@](C)(c2sc(-c3nnc(-c4ncco4)o3)cc2Cl)CS1(=O)=O] | 429 (429) | C 0.77 | 440.8 |

TABLE 5-continued

| Example no. | Structure | Expected M + H (observed) | LCMS Method; $t_R$ (min) | BACE1 Ki (nM) |
|---|---|---|---|---|
| 42 | 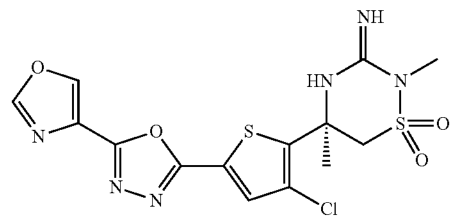 | 429 (429) | C 0.73 | 924.7 |
| 43 | 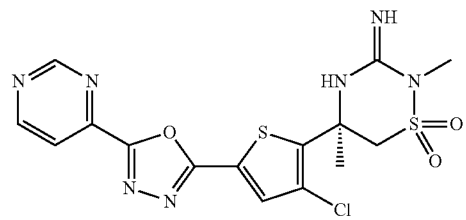 [SMILES: CN1C(=N)N[C@](C)(c2sc(-c3nnc(-c4ccncn4)o3)cc2Cl)CS1(=O)=O] | 440 (440) | C 0.72 | 822.5 |
| 44 | 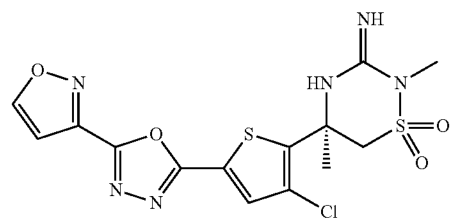 [SMILES: CN1C(=N)N[C@](C)(c2sc(-c3nnc(-c4ccon4)o3)cc2Cl)CS1(=O)=O] | 429 (429) | C 0.81 | 1336 |
| 45 | 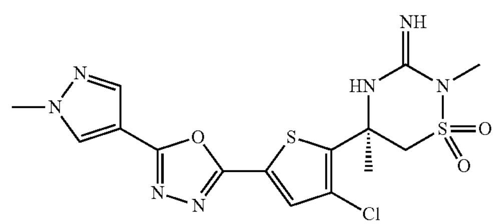 [SMILES: CN1C(=N)N[C@](C)(c2sc(-c3nnc(-c4cnn(C)c4)o3)cc2Cl)CS1(=O)=O] | 442 (442) | C 0.75 | 406.6 |
| 46 | 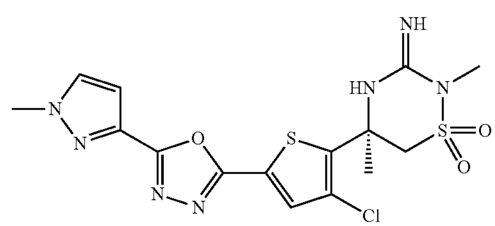 [SMILES: CN1C(=N)N[C@](C)(c2sc(-c3nnc(-c4ccn(C)n4)o3)cc2Cl)CS1(=O)=O] | 442 (442) | C 0.76 | 1139 |
| 47 | 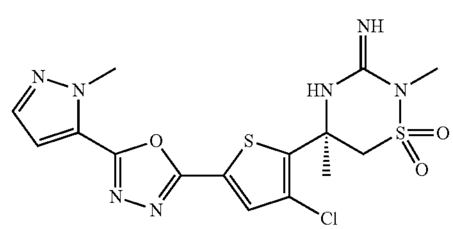 [SMILES: CN1C(=N)N[C@](C)(c2sc(-c3nnc(-c4ccnn4C)o3)cc2Cl)CS1(=O)=O] | 442 (442) | C 0.83 | 1525 |
| 48 | 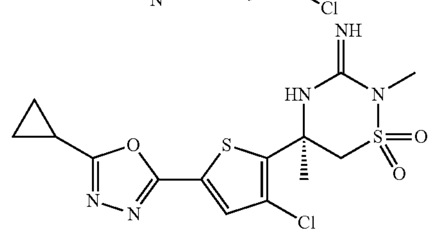 | 402 (402) | C 0.82 | 882.4 |

Method P

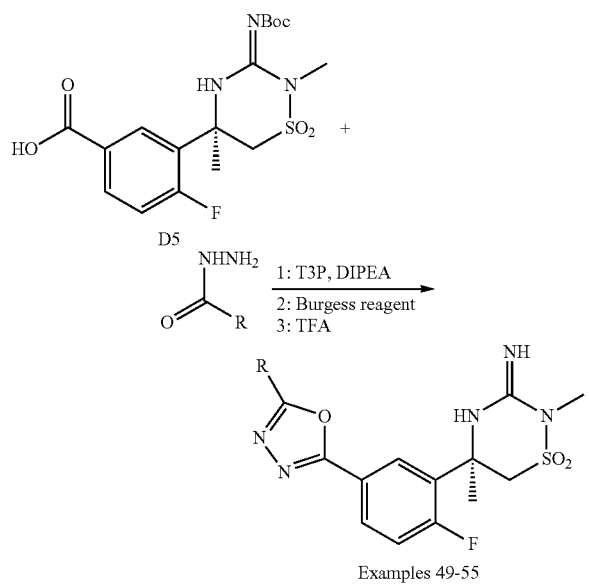

Parallel preparation of Examples 49-55

Step 1 To a set of vials containing a solution of D5 (30 mg, 0.072 mmol) in $CH_2Cl_2$ (1 mL) was added the appropriate acyl hydrazide (1.1 equiv.) and DIEA (28.0 mg, 0.217 mmol). The mixture was stirred for 5 minutes after which T3P (29.9 mg, 0.094 mmol) (50% solution in EtOAc) was added. The reaction mixtures were stirred at room temperature for 18 h.

Step 2 Water (2 mL) and $CH_2Cl_2$ (2 mL) were added to each reaction. After stirring for 5 minutes, the organic layers were separated and concentrated in vacuo.

Step 3 The residues from step 2 were redissolved in $CH_2Cl_2$ (1 mL). Burgess reagent (25.8 mg, 0.108 mmol) and DIEA (28.0 mg, 0.217 mmol) were added and the mixtures were heated at 65° C. for one hour.

Step 4 The reaction mixtures from step 3 were cooled to room temperature and treated with TFA (0.3 mL). After 30 minutes, the mixtures were concentrated in vacuo.

Step 5 Each crude product from step 4 was redissolved in 1 mL of DMSO and filtered. The crude products were purified by mass triggered HPLC (Waters Sunfire C18 column, 5 μm, 19×100 mm, using gradient ranges from 5-10% initial to 20-40% final [MeCN (0.1% Formic acid)/water (0.1% Formic acid)]) to provide Examples 49-55.

TABLE 6

| Example no. | Structure | Expected M + H (Observed) | LCMS Method; $t_R$ (min) | BACE1 Ki (nM) |
|---|---|---|---|---|
| 49 | 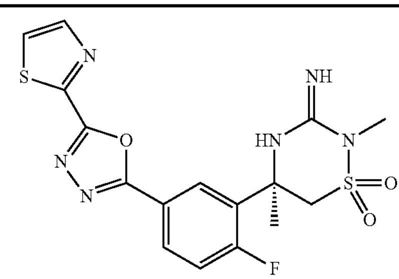 | 423 (423) | C 0.73 | 4002 |
| 50 | 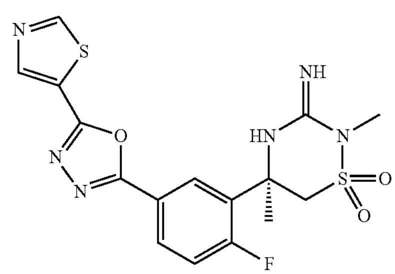 [SMILES: CN1C(=N)N[C@](C)(c2cc(-c3nnc(-c4cncs4)o3)ccc2F)CS1(=O)=O] | 423 (423) | C 0.70 | 9923 |
| 51 | 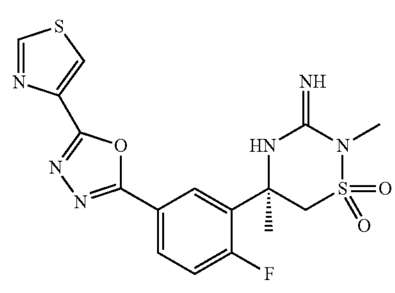 [SMILES: CN1C(=N)N[C@](C)(c2cc(-c3nnc(-c4cscn4)o3)ccc2F)CS1(=O)=O] | 423 (423) | C 0.69 | 8598 |

TABLE 6-continued
| Example no. | Structure | Expected M + H (Observed) | LCMS Method; $t_R$ (min) | BACE1 Ki (nM) |
|---|---|---|---|---|
| 52 | 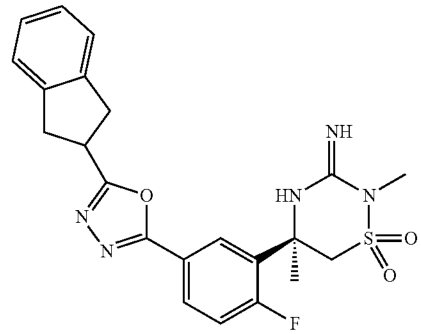 [SMILES: CN1C(=N)N[C@](C)(c2cc(-c3nnc(C4Cc5ccccc5C4)o3)ccc2F)CS1(=O)=O] | 456 (456) | C 0.95 | 7694 |
| 53 | 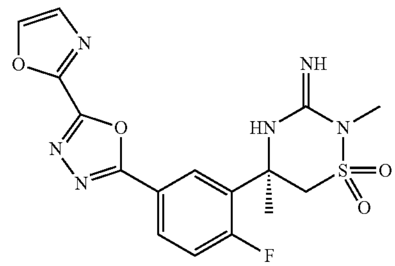 [SMILES: CN1C(=N)N[C@](C)(c2cc(-c3nnc(-c4ncco4)o3)ccc2F)CS1(=O)=O] | 407 (407) | C 0.69 | 3419 |
| 54 | 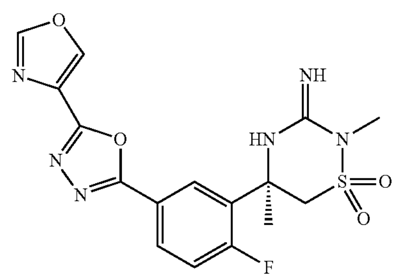 | 407 (407) | C 0.66 | 7548 |
| 55 | 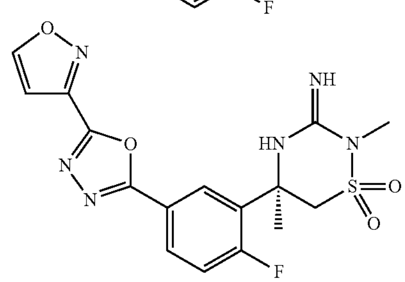 | 407 (407) | C 0.73 | 4940 |
Method Q
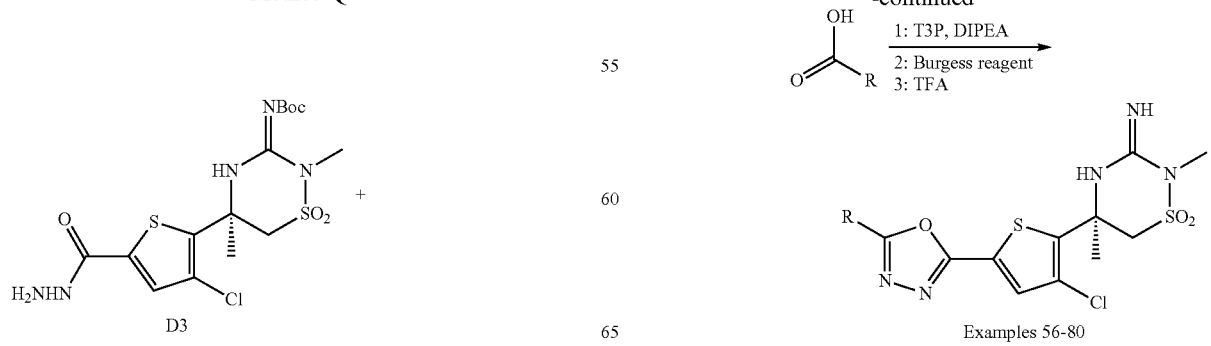

Parallel preparation of Examples 56-80

Step 1 To a set of vials containing D3 (30 mg, 0.066 mmol) in CH$_2$Cl$_2$ (1 mL) was added the requisite carboxylic acid monomer (1.1 equiv.) and DIEA (25.7 mg, 0.199 mmol). The reaction mixtures were stirred for 5 min after which T3P (27.5 mg, 0.086 mmol) (50% solution in EtOAc) was added. The reaction mixtures were stirred at room temperature for 18 h.

Step 2 Water (2 mL) and CH$_2$Cl$_2$ (2 mL) were added to each reaction and the mixtures were stirred for 5 minutes. The organic layers were separated and concentrated in vacuo.

Step 3 The residues from step 2 were redissolved in CH$_2$Cl$_2$ (1 mL). Burgess reagent (23.73 mg, 0.100 mmol) and DIEA (25.7 mg, 0.199 mmol) were added and the reaction mixtures were heated at 65° C. for one hour.

Step 4 The reaction mixtures were cooled to room temperature and treated with TFA (0.3 mL). After 30 minutes, the mixtures were concentrated in vacuo.

Step 5 Each crude product was redissolved in 1 mL of DMSO and filtered. The crude products were purified by mass triggered HPLC (Waters XBridge C18 column, 5 μm, 19×100 mm, using gradient ranges from 10-40% initial to 38-80% final [MeCN (0.1% NH$_4$OH)/water (0.1% NH$_4$OH)]) to provide the Examples 56-80.

TABLE 7

| Example no. | Structure | Expected M + H (Observed) | LCMS Method; $t_R$ (min) | BACE1 Ki (nM) |
|---|---|---|---|---|
| 56 | 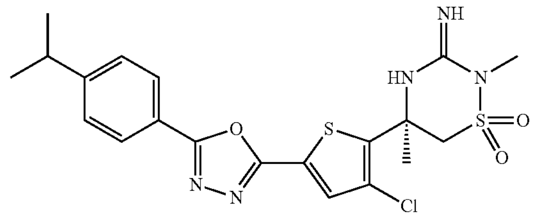 [SMILES: CC(C)c1ccc(-c2nnc(-c3cc(Cl)c([C@]4(C)CS(=O)(=O)N(C)C(=N)N4)s3)o2)cc1] | 480 (480) | C 1.17 | 358.6 |
| 57 | 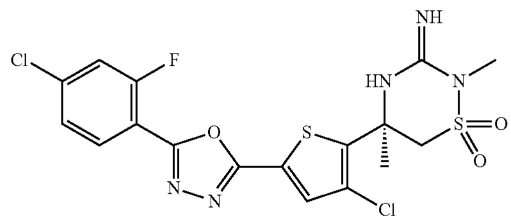 [SMILES: CN1C(=N)N[C@](C)(c2sc(-c3nnc(-c4ccc(Cl)cc4F)o3)cc2Cl)CS1(=O)=O] | 490 (490) | C 1.06 | 50.71 |
| 58 | 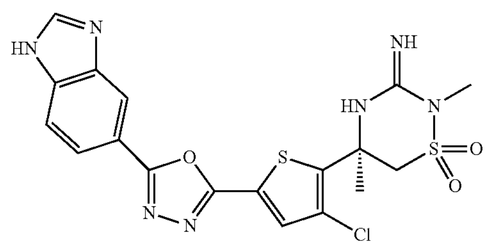 [SMILES: CN1C(=N)N[C@](C)(c2sc(-c3nnc(-c4ccc5[nH]cnc5c4)o3)cc2Cl)CS1(=O)=O] | 478 (478) | D 0.72 | 964.3 |
| 59 | 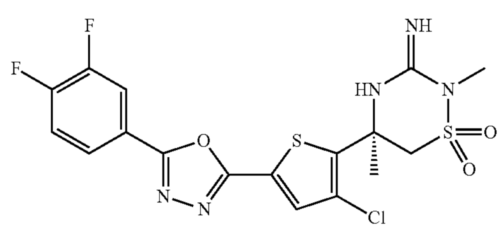 [SMILES: CN1C(=N)N[C@](C)(c2sc(-c3nnc(-c4ccc(F)c(F)c4)o3)cc2Cl)CS1(=O)=O] | 474 (474) | C 1.01 | 117.7 |
| 60 | 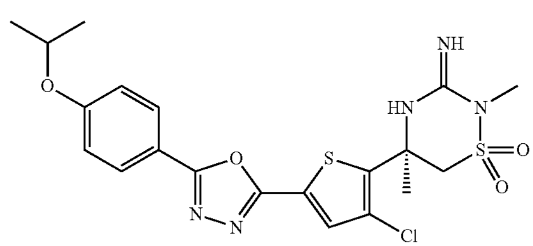 [SMILES: CC(C)Oc1ccc(-c2nnc(-c3cc(Cl)c([C@]4(C)CS(=O)(=O)N(C)C(=N)N4)s3)o2)cc1] | 496 (496) | C 1.10 | 204.9 |

TABLE 7-continued

| Example no. | Structure | Expected M + H (Observed) | LCMS Method; $t_R$ (min) | BACE1 Ki (nM) |
|---|---|---|---|---|
| 61 | 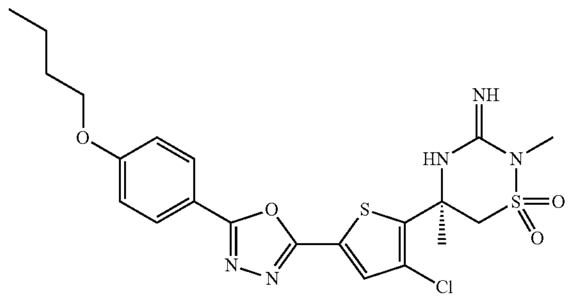 [SMILES: CCCCOc1ccc(-c2nnc(-c3cc(Cl)c([C@]4(C)CS(=O)(=O)N(C)C(=N)N4)s3)o2)cc1] | 510 (510) | C 1.20 | 100.2 |
| 62 | 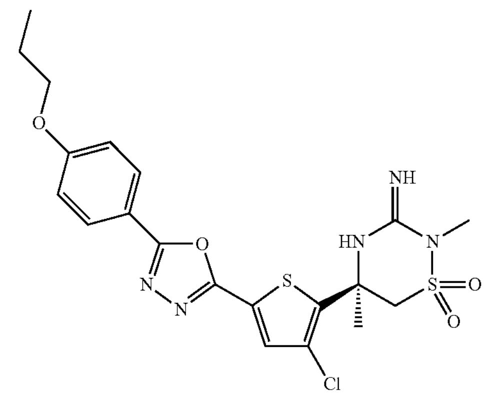 [SMILES: CCCOc1ccc(-c2nnc(-c3cc(Cl)c([C@]4(C)CS(=O)(=O)N(C)C(=N)N4)s3)o2)cc1] | 496 (496) | C 1.13 | 84.19 |
| 63 | 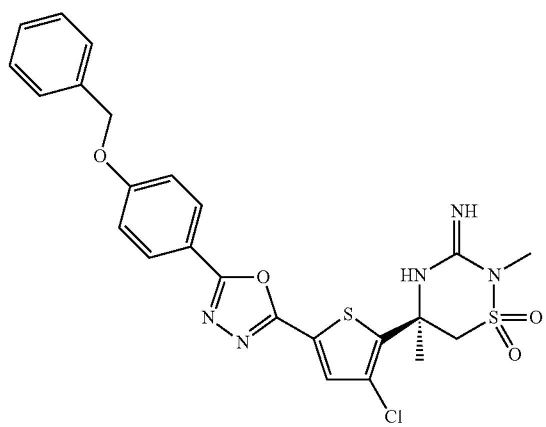 [SMILES: CN1C(=N)N[C@](C)(c2sc(-c3nnc(-c4ccc(OCc5ccccc5)cc4)o3)cc2Cl)CS1(=O)=O] | 544 (544) | C 1.15 | 226.9 |
| 64 | 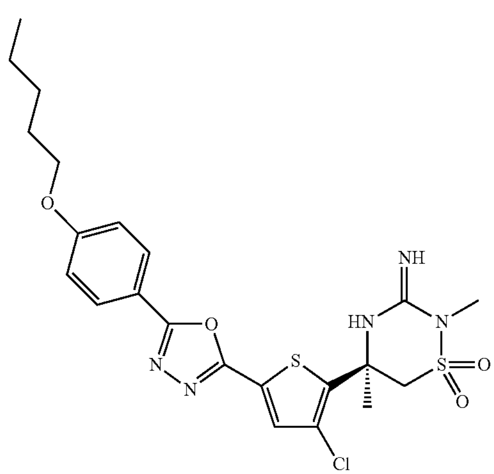 [SMILES: CCCCCOc1ccc(-c2nnc(-c3cc(Cl)c([C@]4(C)CS(=O)(=O)N(C)C(=N)N4)s3)o2)cc1] | 524 (524) | C 1.26 | 160.1 |

TABLE 7-continued

| Example no. | Structure | | Expected M + H (Observed) | LCMS Method; $t_R$ (min) | BACE1 Ki (nM) |
|---|---|---|---|---|---|
| 65 | 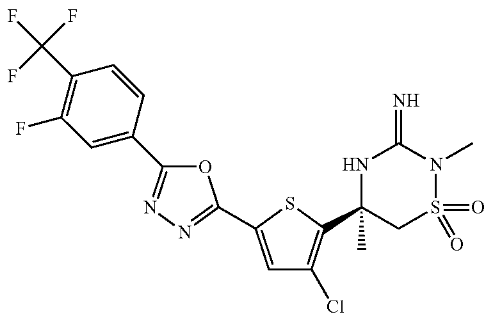 [SMILES: CN1C(=N)N[C@](C)(c2sc(-c3nnc(-c4ccc(C(F)(F)F)c(F)c4)o3)cc2Cl)CS1(=O)=O] | | 524 (524) | C 1.11 | 155.9 |
| 66 | 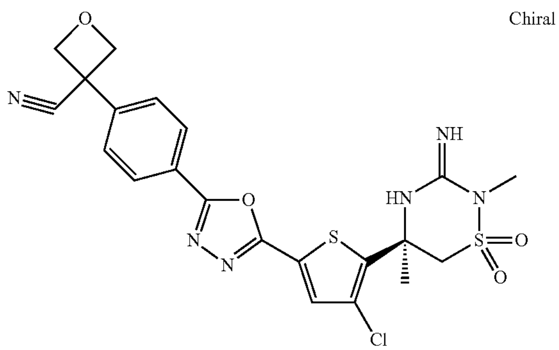 [SMILES: CN1C(=N)N[C@](C)(c2sc(-c3nnc(-c4ccc(C5(C#N)COC5)cc4)o3)cc2Cl)CS1(=O)=O] | Chiral | 519 (519) | C 0.89 | 1361 |
| 67 | 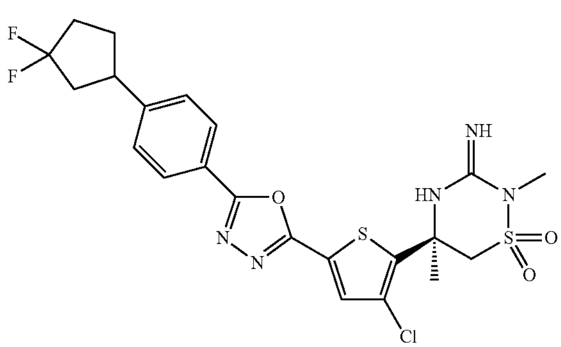 [SMILES: CN1C(=N)N[C@](C)(c2sc(-c3nnc(-c4ccc(C5CCC(F)(F)C5)cc4)o3)cc2Cl)CS1(=O)=O] | | 542 (542) | C 1.12 | 1114 |
| 68 | 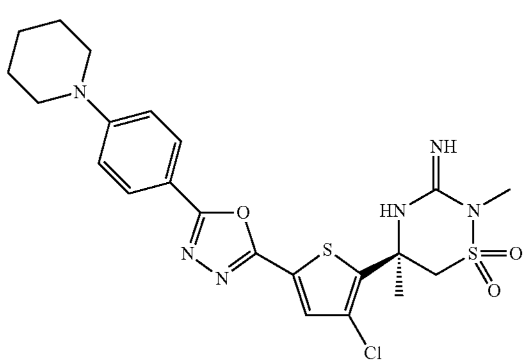 [SMILES: CN1C(=N)N[C@](C)(c2sc(-c3nnc(-c4ccc(N5CCCCC5)cc4)o3)cc2Cl)CS1(=O)=O] | | 521 (521) | C 1.17 | 5362 |

TABLE 7-continued

| Example no. | Structure | Expected M + H (Observed) | LCMS Method; $t_R$ (min) | BACE1 Ki (nM) |
|---|---|---|---|---|
| 69 | 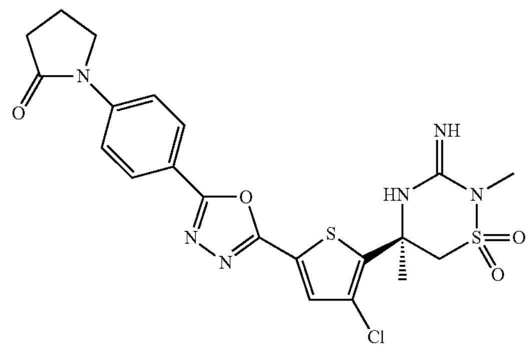 [SMILES: CN1C(=N)N[C@](C)(c2sc(-c3nnc(-c4ccc(N5CCCC5=O)cc4)o3)cc2Cl)CS1(=O)=O] | 521 (521) | C 0.87 | 1026 |
| 70 | 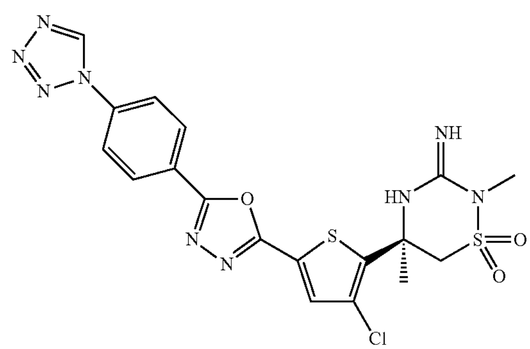 [SMILES: CN1C(=N)N[C@](C)(c2sc(-c3nnc(-c4ccc(-n5cnnn5)cc4)o3)cc2Cl)CS1(=O)=O] | 506 (506) | C 0.83 | 179.5 |
| 71 | 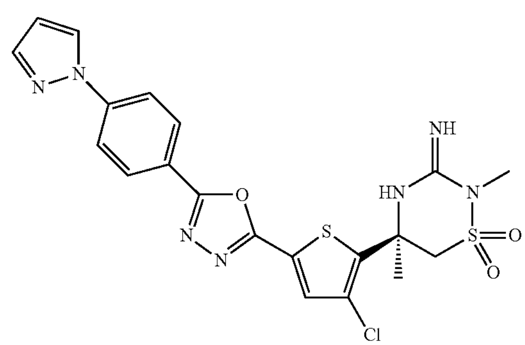 [SMILES: CN1C(=N)N[C@](C)(c2sc(-c3nnc(-c4ccc(-n5cccn5)cc4)o3)cc2Cl)CS1(=O)=O] | 504 (504) | C 0.96 | 155.3 |
| 72 | 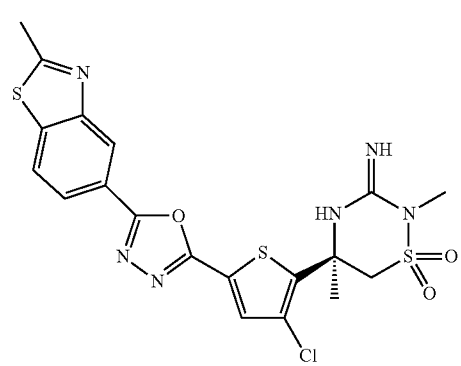 [SMILES: Cc1nc2cc(-c3nnc(-c4cc(Cl)c([C@]5(C)CS(=O)(=O)N(C)C(=N)N5)s4)o3)ccc2s1] | 509 (509) | C 0.97 | 421.8 |

TABLE 7-continued
| Example no. | Structure | Expected M + H (Observed) | LCMS Method; $t_R$ (min) | BACE1 Ki (nM) |
|---|---|---|---|---|
| 73 | 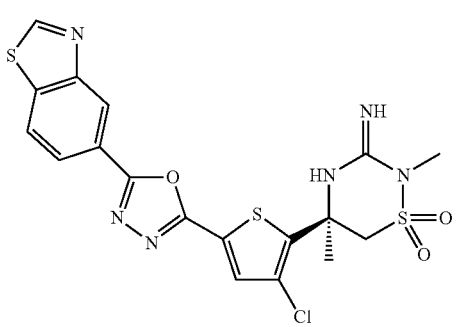 [SMILES: CN1C(=N)N[C@](C)(c2sc(-c3nnc(-c4ccc5scnc5c4)o3)cc2Cl)CS1(=O)=O] | 495 (495) | C 0.91 | 170.7 |
| 74 | 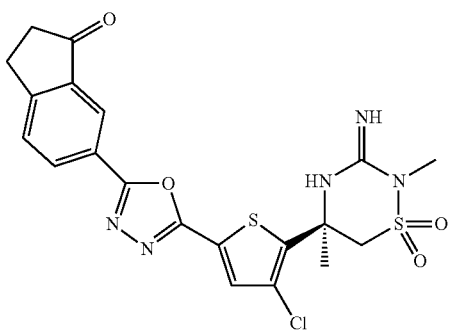 [SMILES: CN1C(=N)N[C@](C)(c2sc(-c3nnc(-c4ccc5c(c4)C(=O)CC5)o3)cc2Cl)CS1(=O)=O] | 492 (492) | C 0.89 | 887.1 |
| 75 | 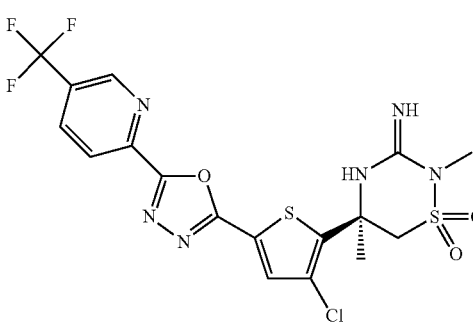 | 507 (507) | C 0.97 | 164.5 |
| 76 | 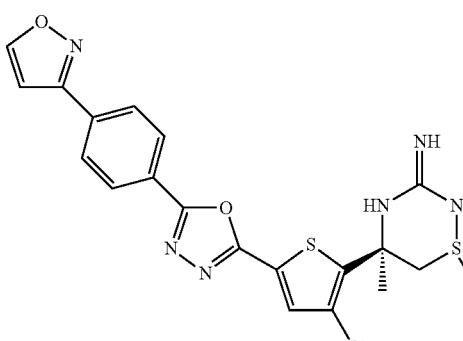 | 505 (505) | C 0.96 | 108.5 |

TABLE 7-continued

| Example no. | Structure | Expected M + H (Observed) | LCMS Method; $t_R$ (min) | BACE1 Ki (nM) |
|---|---|---|---|---|
| 77 | 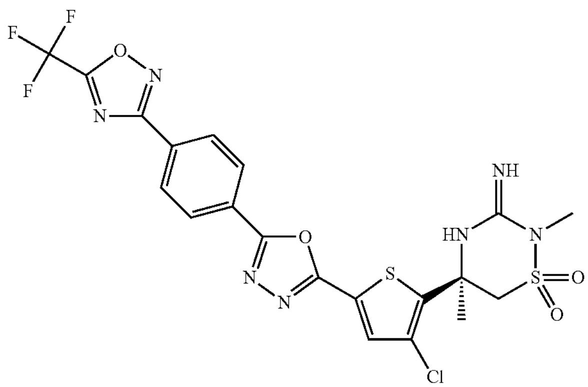 [SMILES: CN1C(=N)N[C@](C)(c2sc(-c3nnc(-c4ccc(-c5noc(C(F)(F)F)n5)cc4)o3)cc2Cl)CS1(=O)=O] | 574 (574) | C 1.16 | 257.9 |
| 78 | 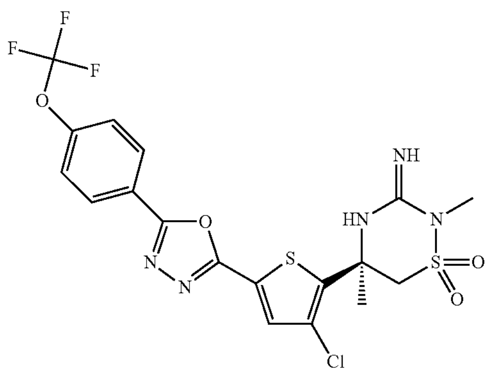 [SMILES: CN1C(=N)N[C@](C)(c2sc(-c3nnc(-c4ccc(OC(F)(F)F)cc4)o3)cc2Cl)CS1(=O)=O] | 522 (522) | C 1.10 | 55.99 |
| 79 | 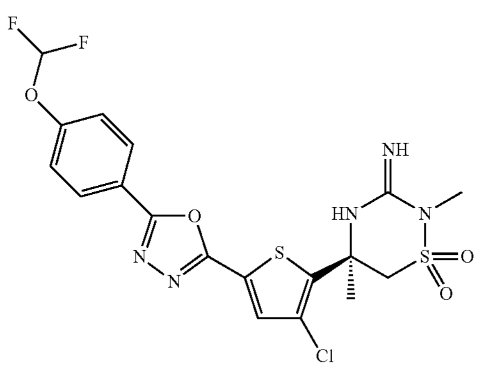 [SMILES: CN1C(=N)N[C@](C)(c2sc(-c3nnc(-c4ccc(OC(F)F)cc4)o3)cc2Cl)CS1(=O)=O] | 504 (504) | C 1.00 | 51.64 |
| 80 | 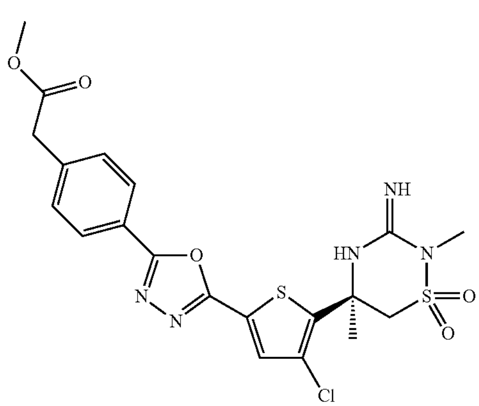 [SMILES: COC(=O)Cc1ccc(-c2nnc(-c3cc(Cl)c([C@]4(C)CS(=O)(=O)N(C)C(=N)N4)s3)o2)cc1] | 510 (510) | C 0.94 | 137.9 |

Method R

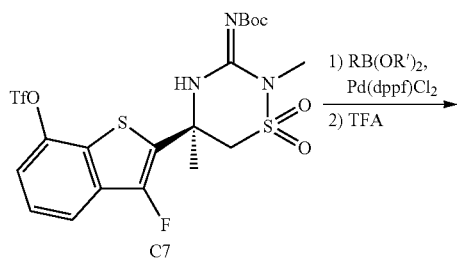

C7

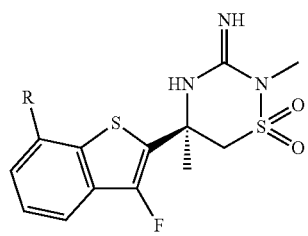

Examples 81-83

Parallel preparation of Examples 81-83

Step 1 To a set of 2-dram vials containing a stir bar was individually added the appropriate boronic acid/pinacol ester. To each vial was then added $PdCl_2(dppf)\text{-}CH_2Cl_2$ adduct (6.78 mg, 8.30 μmol). The vials were transferred to a glove box under an atmosphere of nitrogen. To each vial was then added a solution of the triflate C14 (29 mg, 0.055 mmol) in dioxane (1 mL) followed by $K_2CO_3$ (1M, 0.166 mL, 0.166 mmol). The vials were capped and then removed from the glove bag and placed into a preheated aluminum block at 65° C. The mixtures were stirred at that temperature for 4 hours.

Step 2 To each vial was added water (2 mL) followed by DCM (2 mL). The mixtures were transferred to a Varian Bond Elute reservoir and the organic layer was drained into a set of 2-dram vials. To each of the aqueous layers was added additional DCM (1 mL). The organic layer was again drained into the set of 2-dram vials. The combined organic layers were concentrated in vacuo.

Step 3 Each crude product was redissolved in 1 mL of DMSO and filtered. The crude products were purified by mass triggered HPLC using the following conditions: [Waters Sunfire C18 column, 5 μm, 19×100 mm, gradient elution from 15% initial to 55% final MeCN (0.1% TFA)/water (0.1% TFA), 50 mL/min, 8 min run time.]

Using the procedure described in Method R, the examples in Table 8 were prepared utilizing the appropriate boronic acid/pinacol ester.

TABLE 8

| Ex. number | Example | M + H: Obs. (Exp.) | LCMS Cond. ($t_R$ min) | BACE1 Ki (nM) |
|---|---|---|---|---|
| 81 | | 470.10 (470) | C (1.08) | 1462 |
| 82 | | 489.08 (489) | C (1.16) | 4887 |

TABLE 8-continued

| Ex. number | Example | M + H: Obs. (Exp.) | LCMS Cond. ($t_R$ min) | BACE1 Ki (nM) |
|---|---|---|---|---|
| 83 | 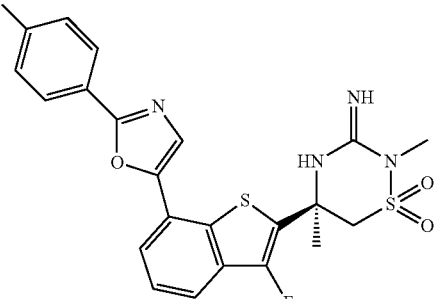 | 489.08 (489) | C (1.12) | 3177 |

Using the procedure described in Method R, B1 was converted to Examples 84-86 by coupling with appropriate boronic acid.

TABLE 9

| Ex. number | Example | M + H: Obs. (Exp.) | LCMS Cond. ($t_R$ min) | BACE1 Ki (nM) |
|---|---|---|---|---|
| 84 | 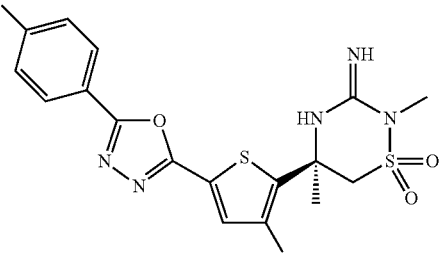 | 455 (455) | C (1.05) | 102 |
| 85 | 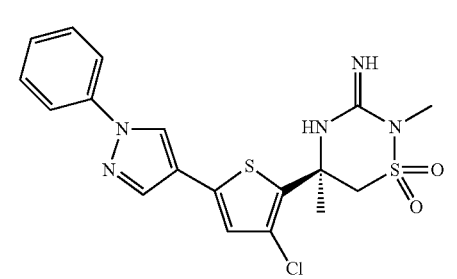 [SMILES: CN1C(=N)N[C@](C)(c2sc(-c3cnn(-c4ccccc4)c3)cc2Cl)CS1(=O)=O] | 436 (436) | C (1.01) | 265 |

LCMS Conditions
Method A
Column: Agilent Zorbax SB-C18 (3.0×50 mm) 1.8 uM
Mobile phase: A: 0.05% Trifluoroacetic acid in water
B: 0.05% Trifluoroacetic acid in acetonitrile
Gradient: 90:10 (A:B) for 0.3 min, 90:10 to 5:95 (A:B) over 5.1 min, 5:95 (A:B) for 1.2 min.
Flow rate: 1.0 mL/min
UV detection: 254 and 220 nm
Column Temp.=50° C.
Mass spectrometer: Agilent 6140 quadrupole.
Method B
Column: Agilent Zorbax SB-C18 (3.0×50 mm) 1.8 uM
Mobile phase: A: H$_2$O/0.05% TFA/0.5% AcOH
B: Acetonitrile/0.05% TFA/0.5% AcOH
Gradient: 90:10 to 5:95 (A:B) over 1.5 min, 5:95 (A:B) for 1.2 min.
Flow rate: 1.0 mL/min
UV detection: 254 and 220 nm
Column Temp.=50° C.
Mass spectrometer: Agilent 6140 quadrupole.
Method C
Acquity UPLC BEH-C18, 1.7 um, 2.1×50 mm
1 mL/min flow
5%-100% MeCN in 1.4 min
0.1% NH3
Assays
Protocols that used to determine the recited potency values for the compounds of the invention are described below.

BACE1 HTRF FRET Assay
Reagents

Na+-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window Inhibitor $IC_{50}$ values are derived from non-linear regression analysis of concentration response curves. $K_i$ values are then calculated from $IC_{50}$ values using the Cheng-Prusoff equation using a previously determined μm value of 8 μM for the QSY7-APP$^{swe}$-Eu substrate at BACE1.

BACE-2 Assay

Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 μM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation. BACE2 Ki values for the non-limiting example compounds of the invention are are shown in Table 10 below.

TABLE 10

| Ex. No | BACE2 Ki (nM) |
|---|---|
| 1 | 0.69 |
| 2 | 14.76 |
| 3 | 87.92 |
| 4 | 3119 |
| 5 | 281.4 |
| 6 | 69 |
| 7 | 35 |
| 8 | 10.91 |
| 9 | 8.243 |
| 10 | 11.29 |
| 11 | 171.7 |
| 12 | 364.5 |
| 13 | 206.9 |
| 14 | 143.6 |
| 15 | 52.64 |
| 16 | 13.79 |
| 17 | 34.61 |
| 18 | 154.7 |
| 19 | 13.6 |
| 20 | 7.762 |
| 21 | 58.41 |
| 22 | 13.04 |
| 23 | 44.92 |
| 24 | 1492 |
| 25 | 595.3 |
| 26 | 801.5 |
| 27 | 283.5 |
| 28 | 332.1 |
| 29 | 697.8 |
| 30 | 96.78 |
| 31 | 1235 |
| 32 | 44.29 |
| 33 | 346.9 |
| 34 | 217 |
| 35 | 449.7 |
| 36 | 104.5 |
| 37 | 69.07 |
| 38 | 124.3 |
| 39 | 1659 |
| 40 | 141.5 |
| 41 | 31.68 |
| 42 | 142.5 |
| 43 | 305.2 |
| 44 | 156.5 |
| 45 | 226 |
| 46 | 129.5 |
| 47 | 712.4 |
| 48 | 115.8 |
| 49 | 489.8 |
| 50 | 4220 |
| 51 | 1535 |
| 52 | 2676 |
| 53 | 185.8 |
| 54 | 1686 |
| 55 | 736.6 |
| 56 | 889.4 |
| 57 | 16.77 |
| 58 | 1299 |
| 59 | 81.32 |
| 60 | 532.8 |
| 61 | 257.6 |
| 62 | 312.7 |
| 63 | 527.3 |
| 64 | 355.8 |
| 65 | 366.2 |
| 66 | 1070 |
| 67 | 1866 |
| 68 | 2992 |
| 69 | 1070 |
| 70 | 1353 |
| 71 | 181.2 |
| 72 | 1154 |
| 73 | 336 |

TABLE 10-continued

| Ex. No | BACE2 Ki (nM) |
|---|---|
| 74 | 1994 |
| 75 | 303.4 |
| 76 | 242.7 |
| 77 | 1279 |
| 78 | 143.2 |
| 79 | 131.8 |
| 80 | 671.2 |
| 81 | 337 |
| 82 | 2943 |
| 83 | 3315 |
| 84 | 10.64 |
| 85 | 27.87 |

The compounds of the invention, surprisingly and advantageously, inhibit BACE, as shown by the BACE inhibitory data reported herein. Some of the compounds of the invention, suprisingly and advantageously, demonstrate low susceptibility to efflux by human P-glycoprotein, as evidenced by a low efflux ratio (Pgp Mdr1 ER), as shown in Table 11 below.

TABLE 11

| Ex | Structure | Pgp Mdr1 ER |
|---|---|---|
| 16 | 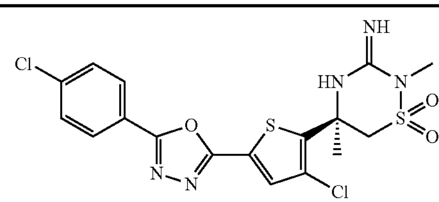 | 1.1 |
| 17 | 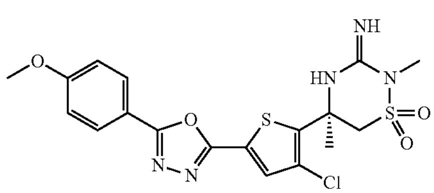 [SMILES: COc1ccc(-c2nnc(-c3cc(Cl)c([C@]4(C)CS(=O)(=O)N(C)C(=N)N4)s3)o2)cc1] | 1.0 |
| 18 | 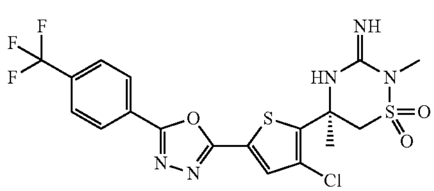 [SMILES: CN1C(=N)N[C@](C)(c2sc(-c3nnc(-c4ccc(C(F)(F)F)cc4)o3)cc2Cl)CS1(=O)=O] | 0.7 |
| 19 | 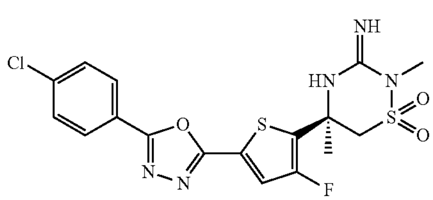 | 1.0 |
| 20 | 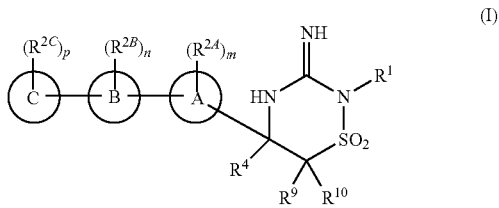 | 1.3 |
| 22 | 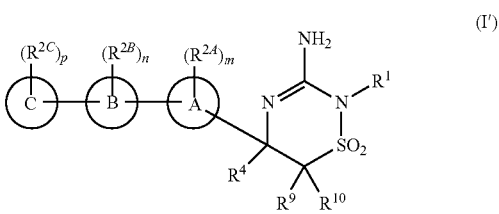 | 1.4 |

We claim:

1. A compound, or a stereoisomer of said compound, or a pharmaceutically acceptable salt of said compound or said stereoisomer, said compound having the structural Formula (I):

(I)

or a tautomer thereof having the structural Formula (I'):

(I')

or pharmaceutically acceptable salt thereof, wherein:
$R^1$ is selected from the group consisting of H, lower alkyl, and cyclopropyl;
ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;
each $R^{2A}$ (when present) is independently selected from the group consisting of: halo, oxo, —OH, —CN, —SF$_5$, —$OSF_5$, —$NO_2$, —$Si(R^5)_3$, —$N(R^6)_2$, —$OR^6$, —$SR^6$, alkyl, haloalkyl, heteroalkyl, alkenyl, alkynyl, cycloalkyl, -alkyl-cycloalkyl, heterocycloalkyl, and -alkyl-heterocycloalkyl, wherein said alkyl, haloalkyl, heteroalkyl, alkenyl, alkynyl, cycloalkyl, -alkyl-cycloalkyl, heterocycloalkyl, and -alkyl-heterocycloalkyl of $R^{2A}$ are each optionally unsubstituted or substituted with one or more groups independently selected from $R^8$;

m is 0 or more;

ring B is selected from the group consisting of a 5-membered heteroaryl, a 5-membered heterocycloalkyl, a 5-membered heterocycloalkenyl ring, a 5-membered cycloalkyl ring, and a 5-membered cycloalkenyl ring, wherein each said ring comprises from 1 to 4 ring heteroatoms independently selected from the group consisting of N, N-oxide, O, S, S(O), and $S(O)_2$;

each $R^{2B}$ (when present) is independently selected from the group consisting of halo, —CN, alkyl, cycloalkyl, -alkyl-cycloalkyl, heterocycloalkyl, -alkyl-heterocycloalkyl, heteroalkyl, haloalkyl —O-alkyl, —O-cycloalkyl, —O-alkyl-cycloalkyl, —O-heteroalkyl, and —O-haloalkyl;

n is 0 or more;

ring C is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2C}$ (when present) is independently selected from the group consisting of: halo, oxo, —OH, —CN, —$SF_5$, —$OSF_5$, —$Si(R^5)_3$, —$N(R^6)_2$, —$NR^7C(O)R^6$, —$NR^7S(O)_2R^{12}$, —$NR^7S(O)_2N(R^6)_2$, —$NR^7C(O)N(R^6)_2$, —$NR^7C(O)OR^6$, —$C(O)R^6$, —$C(O)_2R^6$, —$C(O)N(R^6)_2$, —$S(O)R^{12}$, —$S(O)_2R^{12}$, —$S(O)_2N(R^6)_2$, —$OR^6$, —$SR^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^{2C}$ are each optionally unsubstituted or substituted with one or more groups independently selected from $R^8$;

p is 0 or more;

$R^4$ is selected from the group consisting of lower alkyl and lower haloalkyl;

each $R^5$ (when present) is independently selected from the group consisting of alkyl, heteroalkyl, haloalkyl, cycloalkyl, and -alkyl-cycloalkyl;

each $R^6$ (when present) is independently selected from the group consisting of H, alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^6$ is unsubstituted or substituted with one or more groups independently selected from halo, —CN, —OH, lower alkyl, cycloalkyl, lower heteroalkyl, lower haloalkyl, lower —O-alkyl, lower —O-heteroalkyl, and lower —O-haloalkyl;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said cycloalkyl, -alkyl-cycloalkyl, aryl, -alkyl-aryl, heteroaryl, and -alkyl-heteroaryl of $R^7$ is unsubstituted or substituted with one or more groups independently selected from halo, —CN, lower alkyl, cycloalkyl, lower heteroalkyl, lower haloalkyl, lower —O-alkyl, lower —O-heteroalkyl, and lower —O-haloalkyl;

each $R^8$ (when present) is independently selected from the group consisting of halo, oxo, —OH, —CN, —$SF_5$, —$OSF_5$, alkyl, —O-alkyl, haloalkyl, haloalkoxy, —$C(O)OR^{11}$, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ is selected from the group consisting of H, halo, alkyl, cycloalkyl, haloalkyl, and heteroalkyl;

$R^{10}$ is selected from the group consisting of H, halo, alkyl, cycloalkyl, haloalkyl, and heteroalkyl;

$R^{11}$ (when present) is selected from the group consisting of H, lower alkyl, lower heteroalkyl, cycloalkyl, and -alkyl-cycloalkyl; and each $R^{12}$ (when present) is independently selected from the group consisting of alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^{12}$ is unsubstituted or substituted with one or more groups independently selected from halo, —CN, —OH, lower alkyl, cycloalkyl, lower heteroalkyl, lower haloalkyl, lower —O-alkyl, lower —O-heteroalkyl, and lower —O-haloalkyl.

2. A compound of claim 1, or a tautomer thereof, or a stereoisomer of said compound or said tautomer, or a pharmaceutically acceptable salt of said compound, said tautomer, or said stereoisomer, wherein:

$R^4$ is selected from the group consisting of —$CH_3$ and —$CHF_2$; and one of $R^9$ and $R^{10}$ is H and the other is selected from the group consisting of H, halo, lower alkyl, cycloalkyl, lower haloalkyl, and lower heteroalkyl.

3. A compound of claim 2, or a tautomer thereof, or a stereoisomer of said compound or said tautomer, or a pharmaceutically acceptable salt of said compound, said tautomer, or said stereoisomer, wherein:

ring B is selected from the group consisting of pyrrolyl, imidazolyl, oxadiazolyl, triazolyl, isoxazolyl, oxazolyl, thienyl, pyrazolyl, furanyl, tetrazolyl, thiazolyl, and isothiazolyl.

4. A compound of claim 3, or a tautomer thereof, or a stereoisomer of said compound or said tautomer, or a pharmaceutically acceptable salt of said compound, said tautomer, or said stereoisomer, wherein:

n is 0 or more; and each $R^{2B}$ (when present) is independently selected from the group consisting of halo, —CN, methyl, ethyl, propyl, cyclopropyl, —$CH_2$-cyclopropyl, —$OCH_3$, —$CH_2OCH_3$, —$CHF_2$, —$CH_2F$, —$CF_3$, —$OCF_3$, and —$OCHF_2$.

5. A compound of claim 4, or a tautomer thereof, or a stereoisomer of said compound or said tautomer, or a pharmaceutically acceptable salt of said compound, said tautomer, or said stereoisomer, wherein:

ring A is selected from the group consisting of phenyl, pyridyl, pyrazinyl, furanyl, thienyl, pyrimidinyl, pyridazinyl, thiazolyl, thiadiazolyl, isothiazolyl, oxazolyl, oxadiazolyl, isoxazolyl, imidazolyl, pyrazolyl, pyrrolyl, quinazolinyl, benzofuranyl, benzimidazolyl, benzoxazolyl, benzoisoxazolyl, benzothiazolyl, benzoisothiazolyl, benzothienyl, naphthyl, quinolyl, isoquinolyl, indazolyl, indolyl, thienylpyridinyl, and thienylpyrazolyl.

6. A compound of claim 5, or a tautomer thereof, or a stereoisomer of said compound or said tautomer, or a pharmaceutically acceptable salt of said compound, said tautomer, or said stereoisomer, wherein:

m is 0 or more; and each $R^{2A}$ group (when present) is independently selected from the group consisting of halo, oxo, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, propyl, cyclopropyl, —CH$_2$-cyclopropyl, —C≡C—CH$_3$, —CF$_3$, —CHF$_2$, —OCF$_3$, and —OCHF$_2$.

7. A compound according to claim 6, or a tautomer thereof, or a stereoisomer of said compound or said tautomer, or a pharmaceutically acceptable salt of said compound, said tautomer, or said stereoisomer, wherein:

ring C is selected from the group consisting of benzimidazolyl, benzothiazolyl, cyclopropyl, dihydroindenyl, dihydrooxazolyl, furanyl, indenyl, indolyl, isothiazolyl, isoxazolyl, oxadiazolyl, oxazolyl, phenyl, pyrazinyl, pyrazolyl, pyridazinyl, pyridyl, pyrimidinyl, pyrazolopyridinyl, pyrrolopyridinyl, pyrrolopyrimidinyl, thiazolyl, and thienyl.

8. A compound according to claim 7, or a tautomer thereof, or a stereoisomer of said compound or said tautomer, or a pharmaceutically acceptable salt of said compound, said tautomer, or said stereoisomer, wherein:

p is 0 or more; and each $R^{2C}$ group (when present) is independently selected from the group consisting of halo, oxo, —CN, —SF$_5$, —OSF$_5$, —N(R$^6$)$_2$, —NR$^7$C(O)R$^6$, —NR$^7$S(O)$_2$R$^{12}$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^{12}$, —S(O)$_2$R$^{12}$, —S(O)$_2$N(R$^6$)$_2$, —OR$^6$, —SR$^6$, lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl, wherein each said lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl of R$^2$ (when present) is independently unsubstituted or substituted with one or more groups independently selected from the group consisting of R$^8$.

9. A compound of claim 1, or a tautomer thereof, or a stereoisomer of said compound or said tautomer, or a pharmaceutically acceptable salt of said compound, said tautomer, or said stereoisomer, said compound selected from the group consisting of:

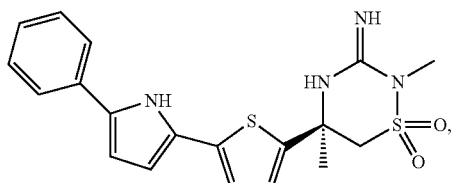

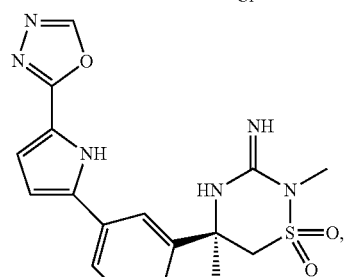

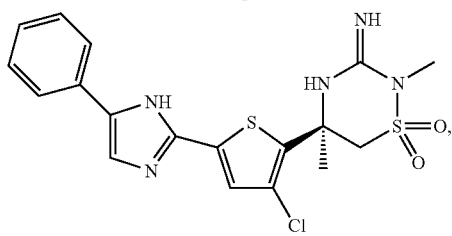

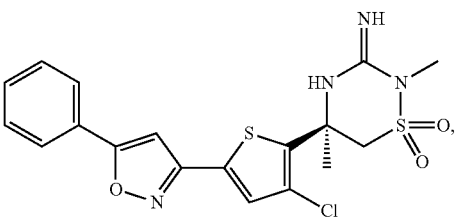

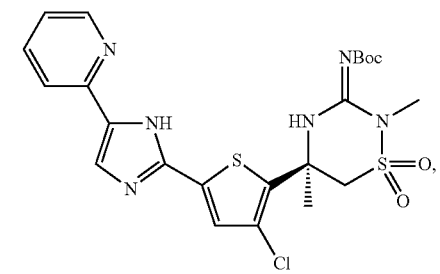

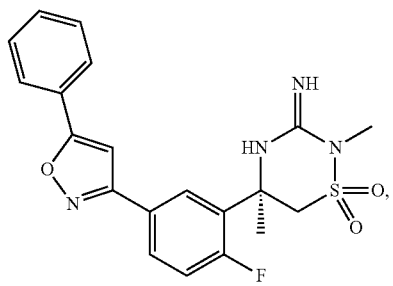

103
-continued
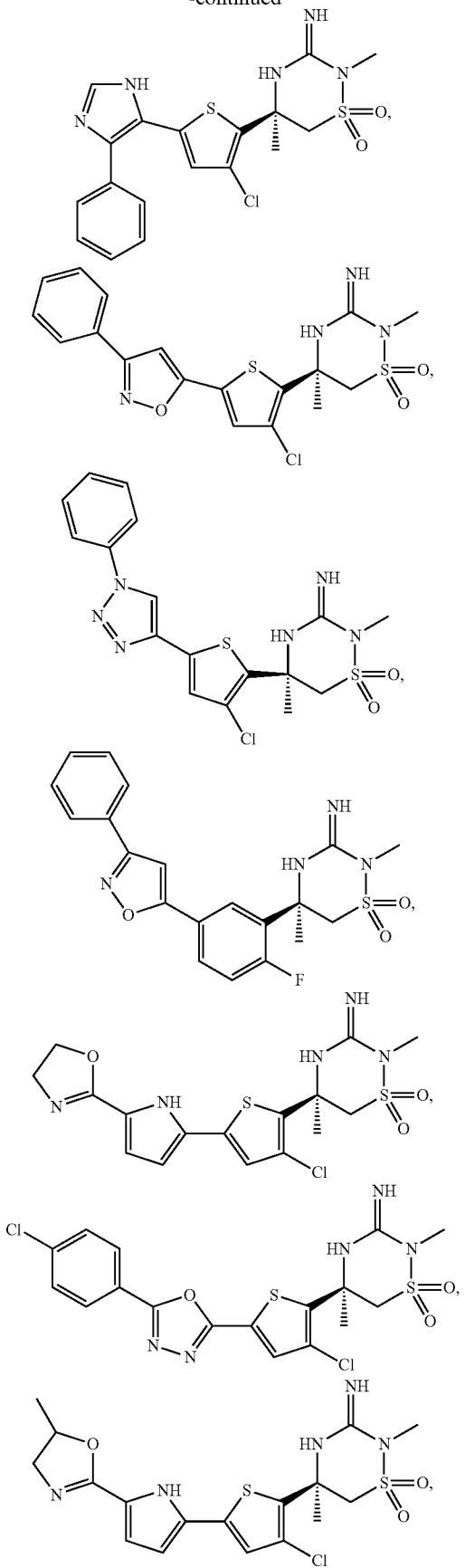
104
-continued
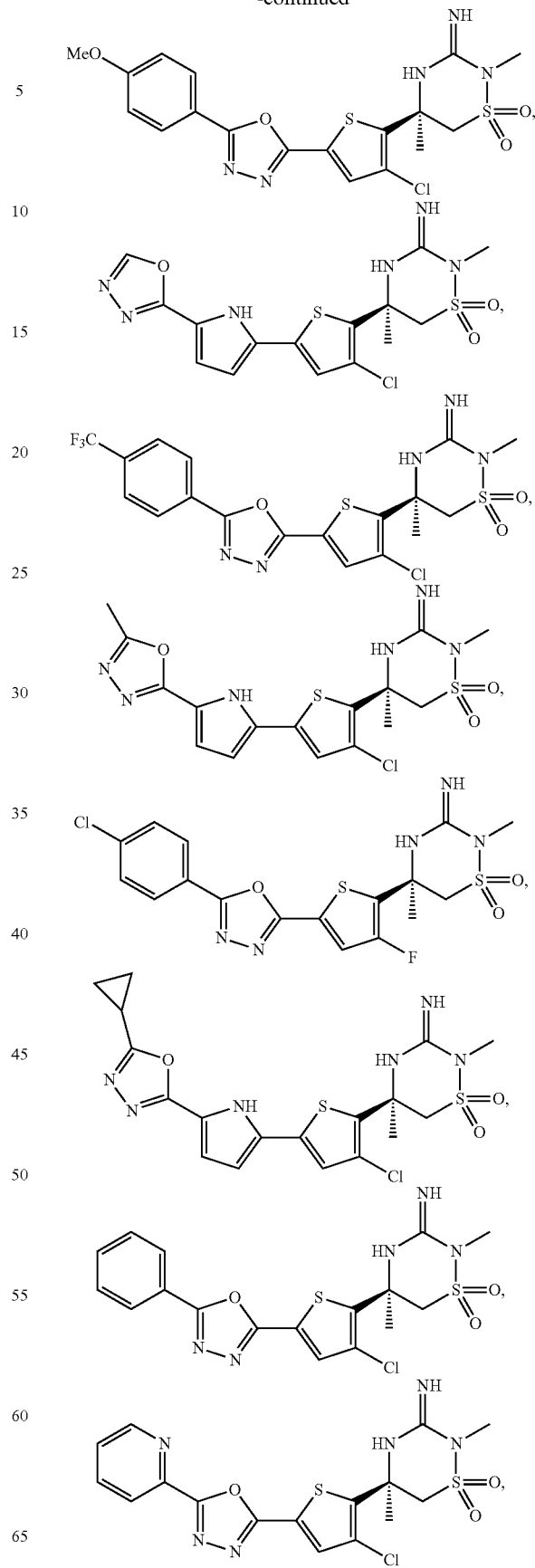

105
-continued
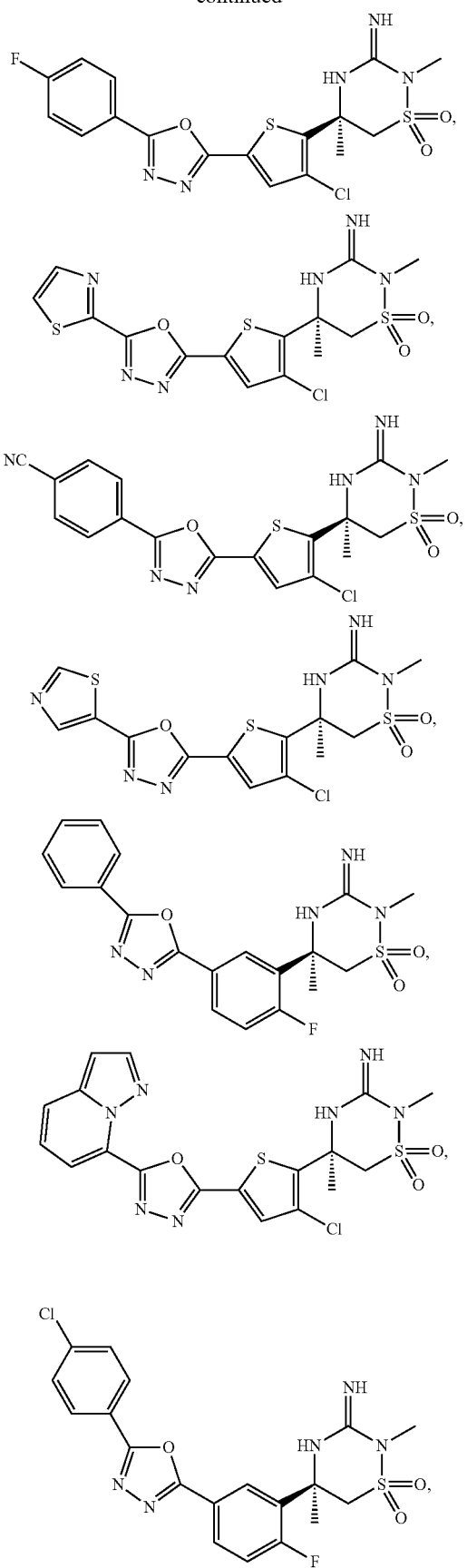
106
-continued
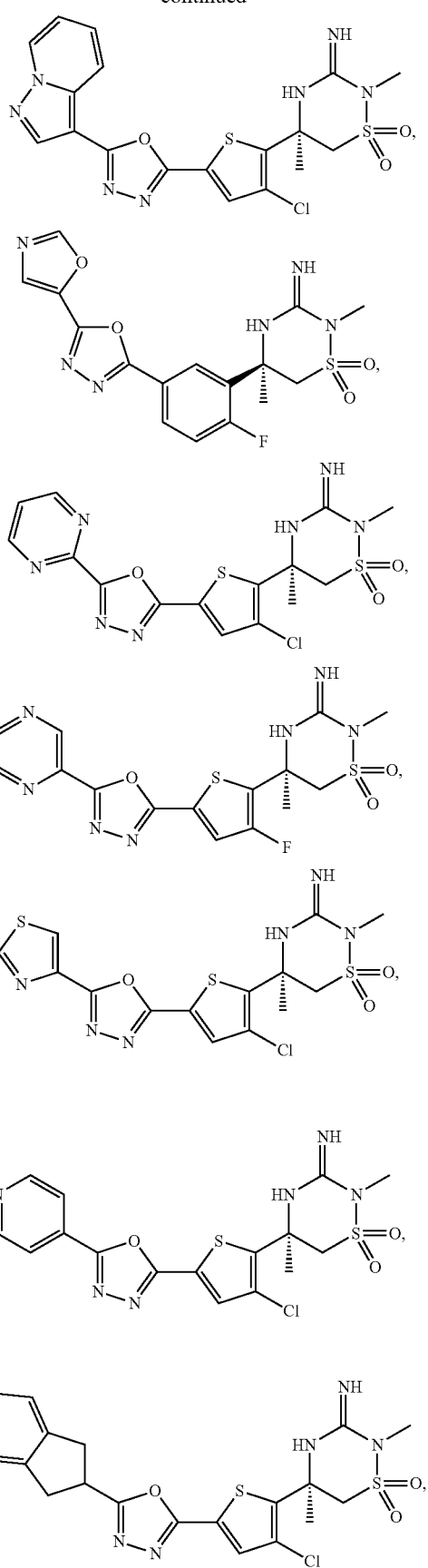

107
-continued
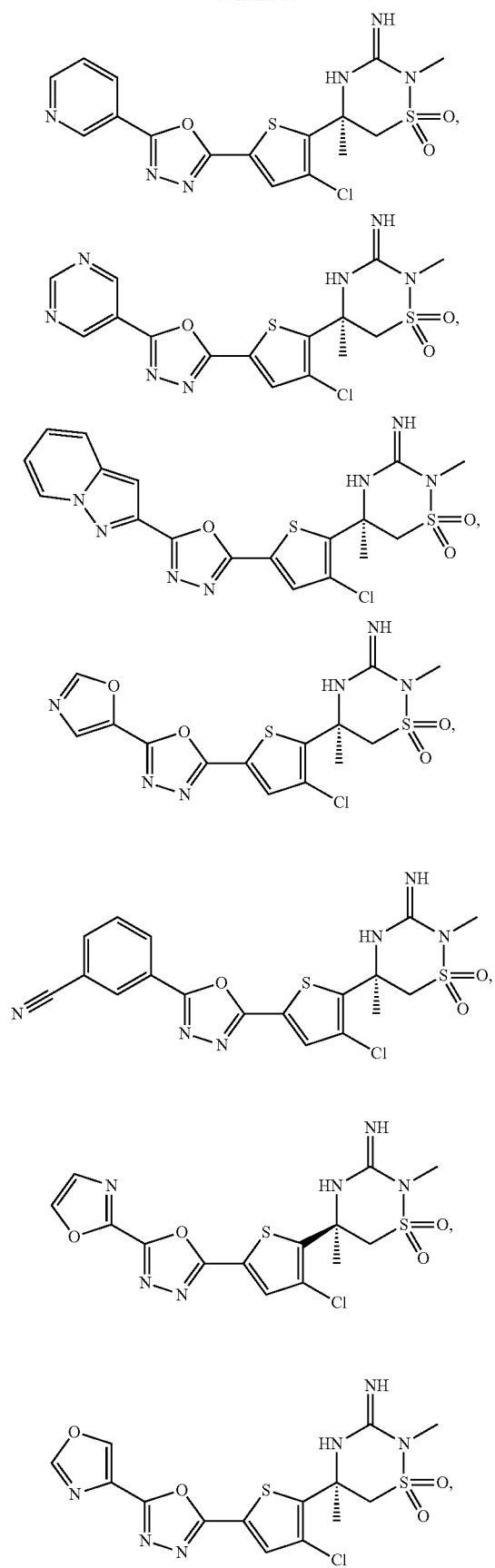
108
-continued
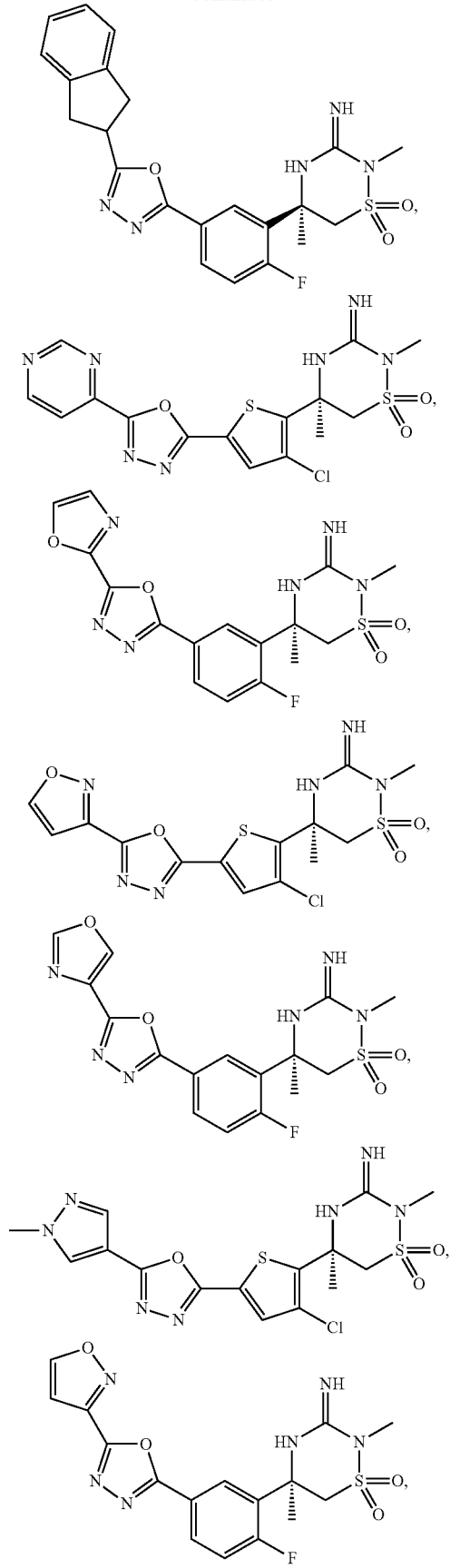

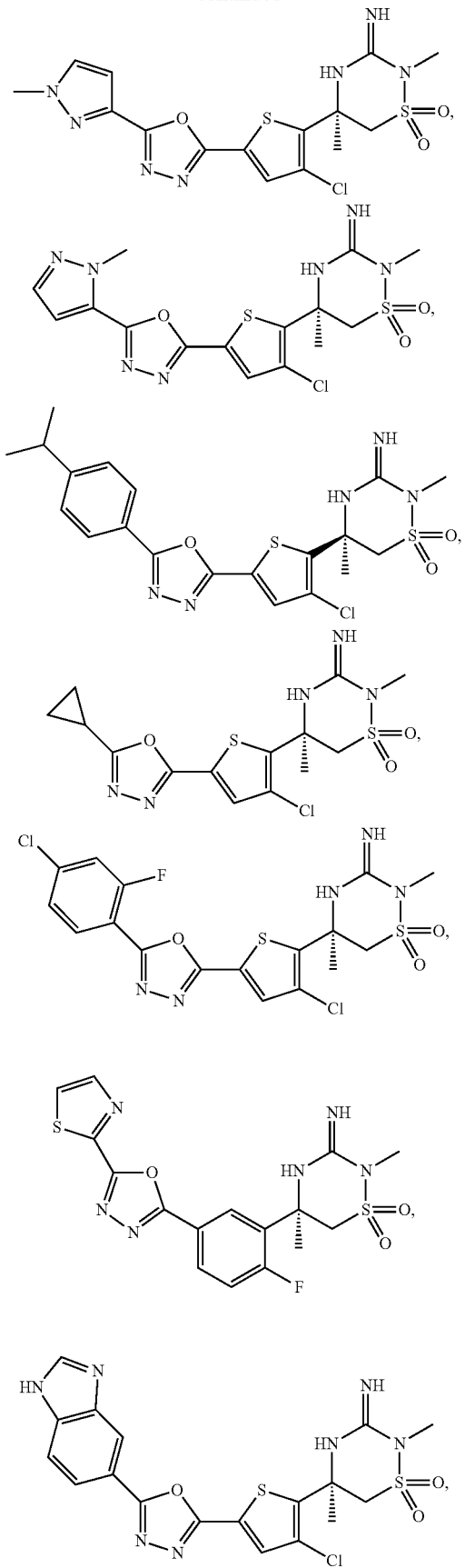
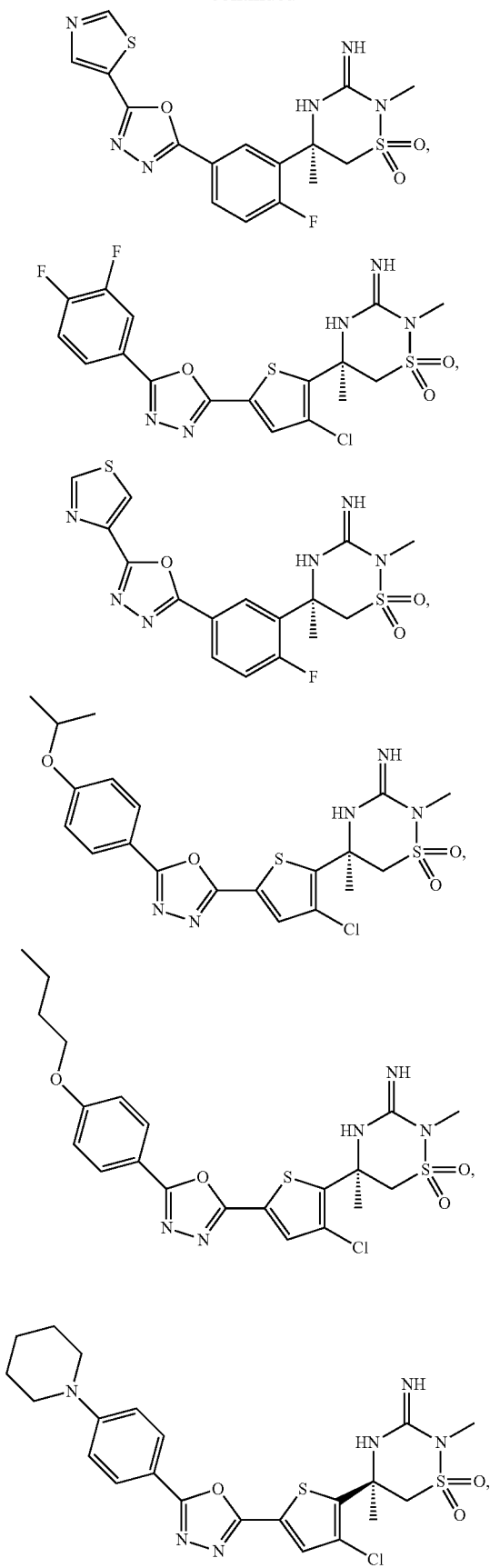

111
-continued
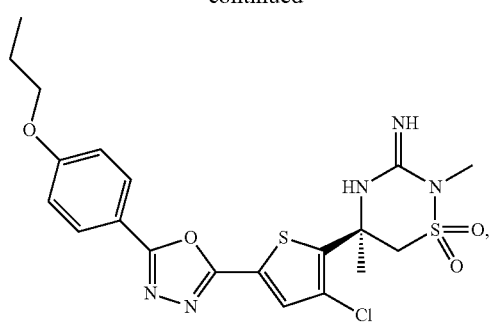
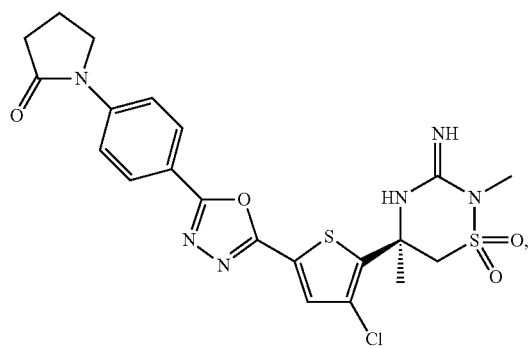
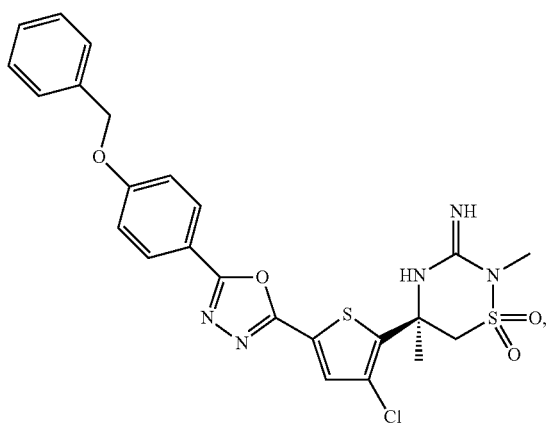
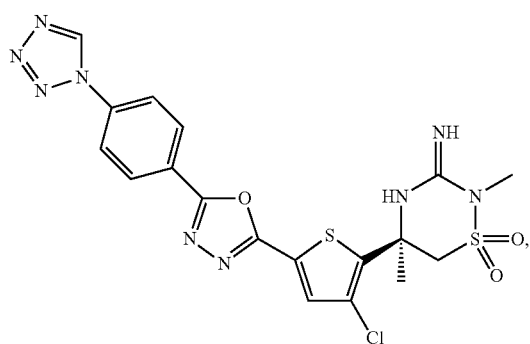
112
-continued
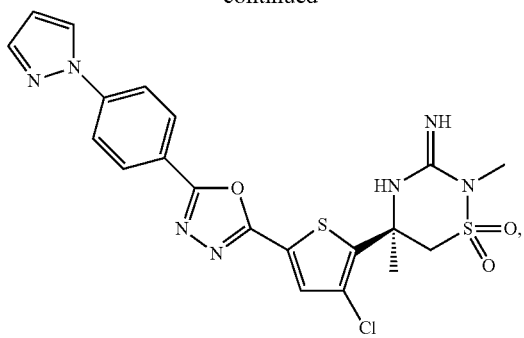
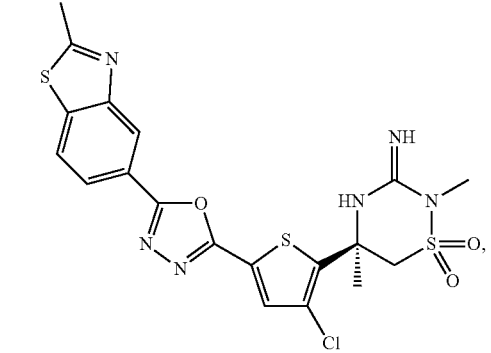
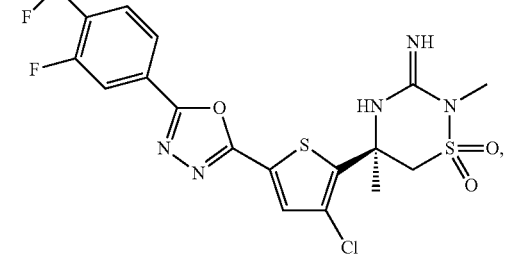

113
-continued
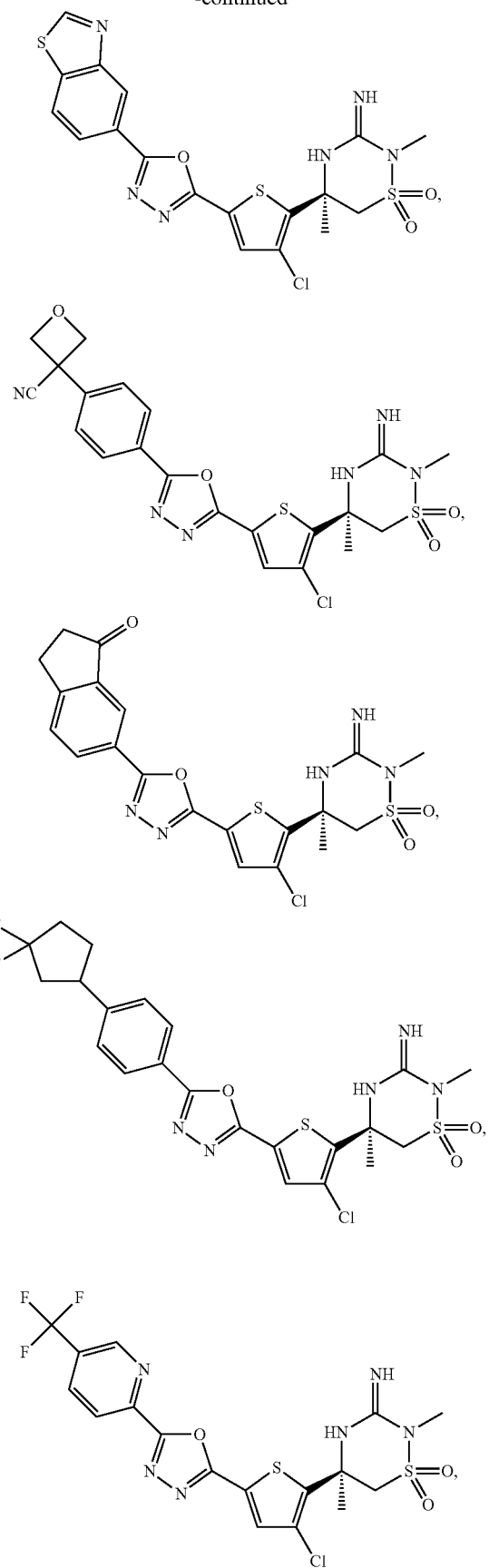
114
-continued
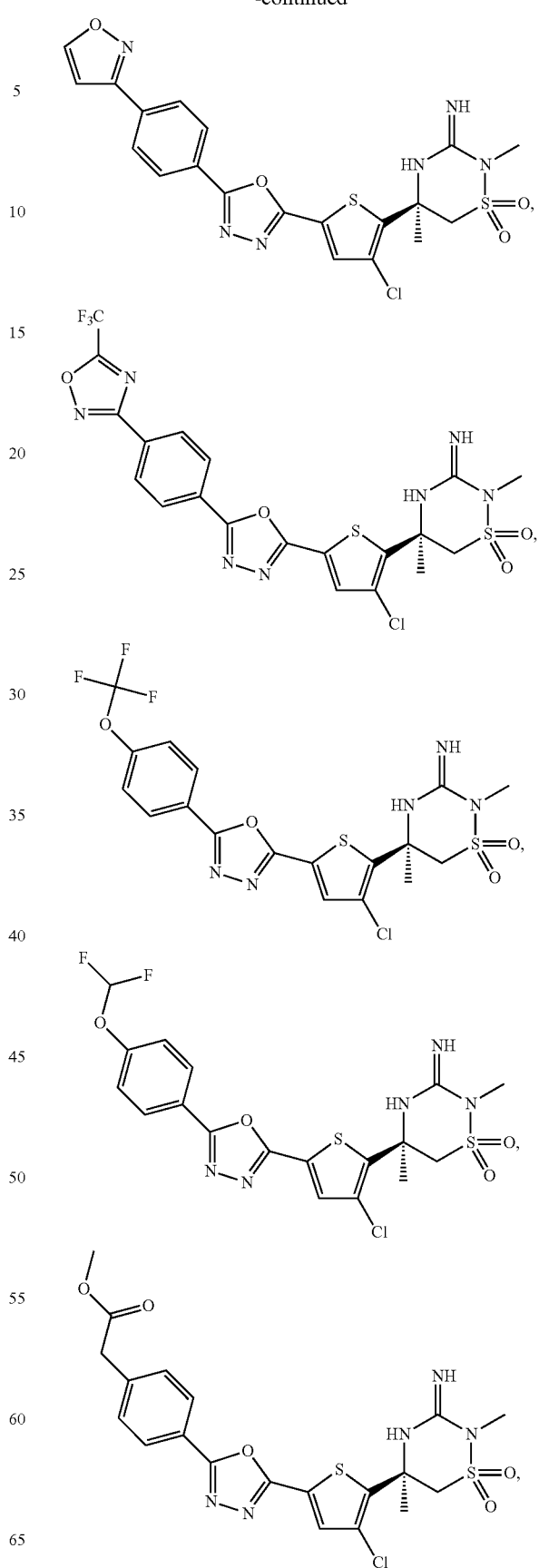

-continued

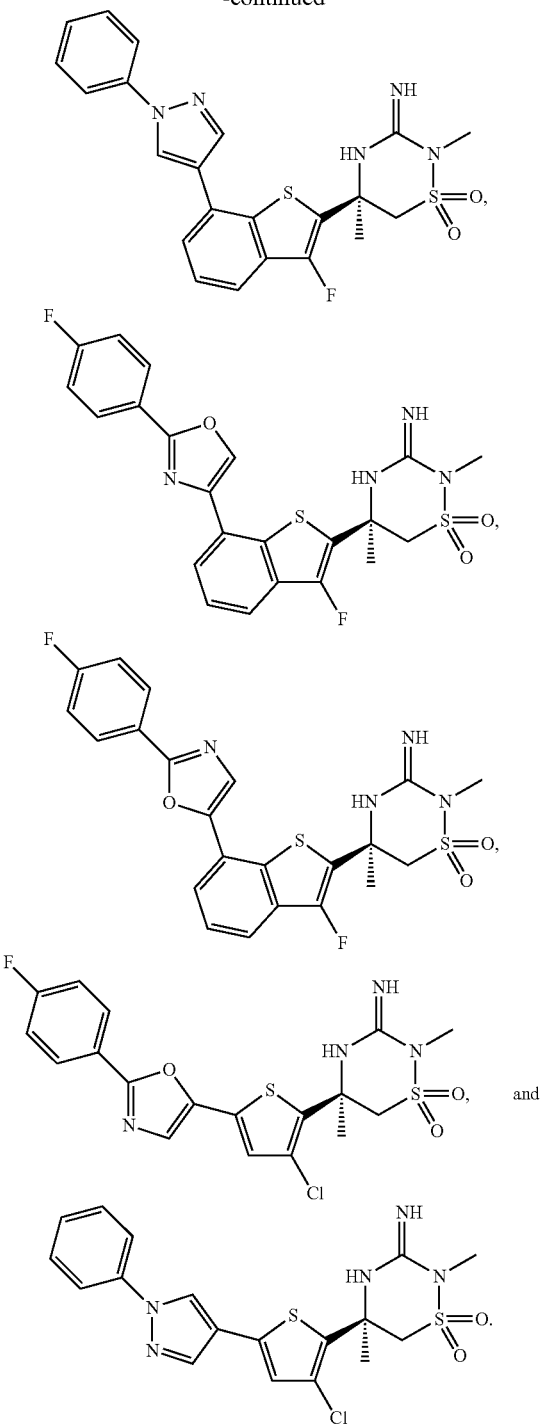

10. A pharmaceutical composition comprising a compound according to claim 1, or a tautomer thereof, or a stereoisomer of said compound or said tautomer, or a pharmaceutically acceptable salt thereof, and a pharmaceutically acceptable carrier or diluent.

11. A pharmaceutical composition of claim 10, wherein said at least one additional therapeutic agent is at least one agent selected from:

$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

12. A method of treating and/or delaying the onset of a disease or pathology, wherein said disease or pathology is selected from Alzheimer's disease, Down's syndrome, Parkinson's disease, memory loss, memory loss associated with Alzheimer's disease, memory loss associated with Parkinson's disease, attention deficit symptoms, attention deficit symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, diabetes-associated amyloidogenesis, hemodialysis complications (from $β_2$ microglobulins and complications arising therefrom in hemodialysis patients), scrapie, bovine spongiform encephalitis, traumatic brain injury ("TBI"), Creutzfeld-Jakob disease, and traumatic brain injury, said method comprising administering a compound according to claim 1, or a tautomer or stereoisomer thereof, or a pharmaceutically acceptable salt thereof, to a patient in need thereof in an amount effective to treat said disease or pathology.

13. A method of claim 12, wherein said Aβ pathology is Alzheimer's disease.

* * * * *